US011065320B2

(12) United States Patent
Hill et al.

(10) Patent No.: US 11,065,320 B2
(45) Date of Patent: Jul. 20, 2021

(54) PRIME TARGET

(71) Applicant: OXFORD UNIVERSITY INNOVATION LIMITED, Oxfordshire (GB)

(72) Inventors: Adrian V. S. Hill, Oxfordshire (GB); Anita Gola, Oxfordshire (GB); Adam Walters, Oxfordshire (GB); Alexandra Spencer, Oxfordshire (GB)

(73) Assignee: OXFORD UNIVERSITY INNOVATION LIMITED, Oxford (GB)

(*) Notice: Subject to any disclaimer, the term of this patent is extended or adjusted under 35 U.S.C. 154(b) by 0 days.

(21) Appl. No.: 16/093,095

(22) PCT Filed: Apr. 11, 2017

(86) PCT No.: PCT/GB2017/051009
§ 371 (c)(1),
(2) Date: Oct. 11, 2018

(87) PCT Pub. No.: WO2017/178809
PCT Pub. Date: Oct. 19, 2017

(65) Prior Publication Data
US 2019/0175714 A1  Jun. 13, 2019

(30) Foreign Application Priority Data

Apr. 12, 2016 (GB) ..................... 1606271
Apr. 29, 2016 (GB) ..................... 1607503
Apr. 29, 2016 (GB) ..................... 1607506

(51) Int. Cl.
| | |
|---|---|
| *C12N 7/02* | (2006.01) |
| *A61K 9/51* | (2006.01) |
| *A61K 9/14* | (2006.01) |
| *A61K 39/015* | (2006.01) |
| *A61K 39/29* | (2006.01) |
| *A61K 39/12* | (2006.01) |
| *C12N 7/00* | (2006.01) |
| *A61K 39/00* | (2006.01) |
| *A61K 39/235* | (2006.01) |
| *A61K 39/275* | (2006.01) |
| *A61K 39/245* | (2006.01) |
| *A61K 39/285* | (2006.01) |

(52) U.S. Cl.
CPC .......... *A61K 39/015* (2013.01); *A61K 39/12* (2013.01); *A61K 39/29* (2013.01); *C12N 7/00* (2013.01); *A61K 2039/5256* (2013.01); *A61K 2039/57* (2013.01); *A61K 2039/572* (2013.01); *C12N 2710/10343* (2013.01); *C12N 2710/24143* (2013.01); *Y02A 50/30* (2018.01)

(58) Field of Classification Search
CPC ........... A61K 2039/5256; A61K 39/12; A61K 2039/70; A61K 39/275; A61K 39/00; A61K 2300/00; A61K 31/7088; A61K 47/6937; A61K 48/00; A61K 9/5153; A61K 48/0041; A61K 49/225; A61K 9/51; C07K 14/445; C07K 14/70539; C07K 5/0819; C12N 15/86; C12N 2760/16134; C12N 2800/22; C12N 2710/161344; C12N 2710/10171
See application file for complete search history.

(56) References Cited

U.S. PATENT DOCUMENTS

| | | | | |
|---|---|---|---|---|
| 6,663,871 | B1 * | 12/2003 | McMichael | ........ A61K 38/1709 424/199.1 |
| 7,407,661 | B2 * | 8/2008 | McMichael | ........ A61K 38/1709 424/199.1 |
| 8,734,806 | B2 * | 5/2014 | Hill | ........ A61K 39/00 424/199.1 |
| 9,017,696 | B2 * | 4/2015 | Draper | ........ C07K 14/78 424/233.1 |
| 9,603,916 | B2 * | 3/2017 | Douglas | ........ A61K 39/015 |

FOREIGN PATENT DOCUMENTS

| | | |
|---|---|---|
| WO | 2003074543 A1 | 9/2003 |
| WO | 2004037189 A2 | 5/2004 |
| WO | 2005018665 A1 | 3/2005 |
| WO | 2012041669 A1 | 4/2012 |
| WO | 2015052543 A2 | 4/2015 |
| WO | 2015052543 A3 | 4/2015 |
| WO | 2016046113 A1 | 3/2016 |

OTHER PUBLICATIONS

Barnes et al. Sci. Transi. Med. Jan. 4, 2012. 4 (115).*
ReiTheraSir (Study of a New MVA Vaccine for Hepatitis C Virus, Clinicl Trials.gov. Identifire: NCT01296451, First posted on line Feb. 15, 2011, last updated Apr. 26, 2016).*
Choo, Yonsei Med J. Feb. 28, 2007; 48(1): 11-23.*
International Search Report issued in PCT/GB2017/051009, dated Aug. 28, 2017.
United Kingdom International Search Report issued in GB1607503.8, dated Feb. 9, 2017.
Agnandji, S.T., et al., "A phase 3 trial of RTS,S/AS01 malaria vaccine in African infants," The New England journal of medicine, 2012. 367(24): p. 2284-95.

(Continued)

*Primary Examiner* — Bao Q Li
(74) *Attorney, Agent, or Firm* — Medler Ferro Woodhouse & Mills

(57) ABSTRACT

The invention relates to a kit comprising at least a first composition and a second composition, each said first and second compositions comprising at least one epitope of a liver disease antigen, wherein said epitope is a CD8+T cell epitope, for use in induction of an immune response in the liver of a mammalian subject by administration of said first composition by intramuscular (i.m.), subcutaneous (s.c.), intradermal (i.d.) or aerosol route, and administration of said second composition by intravenous (i.v.) or subcutaneous (s.c.) route, characterised in that said first and second compositions are administered by different routes. The invention also relates to uses, methods and treatments.

32 Claims, 32 Drawing Sheets

(56) References Cited

OTHER PUBLICATIONS

Agnandji, S.T., et al., "First results of phase 3 trial of RTS,S/AS01 malaria vaccine in African children," The New England journal of medicine, 2011. 365(20): p. 1863-75.

Capone, S., et al., "Immune responses against a liver-stage malaria antigen induced by simian adenoviral vector AdCh63 and MVA prime-boost immunisation in non-human primates," Vaccine, 2010. 29(2): p. 256-65.

Cauley, L.S. and L. Lefrancois, "Guarding the perimeter: protection of the mucosa by tissue-resident memory T cells," Mucosal Immunol, 2013. 6(1): p. 14-23.

Clarke, S.R., et al., "Characterization of the ovalbumin-specific TCR transgenic line OT-I: MHC elements for positive and negative selection," Immunol Cell Biol, 2000. 78(2): p. 110-7.

Clyde, D.F., et al., "Immunization of man against sporozite-induced falciparum malaria," Am J Med Sci, 1973. 266(3): p. 169-77.

Cockburn, I.A., et al., "Dendritic cells and hepatocytes use distinct pathways to process protective antigen from plasmodium in vivo," PLoS pathogens, 2011. 7(3): p. e1001318.

Cockburn, I.A., et al., "Prolonged antigen presentation is required for optimal CD8+ T cell responses against malaria liver stage parasites," PLoS pathogens, 2010. 6(5): p. e1000877.

Crompton, P.D., et al., "Malaria immunity in man and mosquito: insights into unsolved mysteries of a deadly infectious disease," Annual review of immunology, 2014. 32: p. 157-87.

Crispe, I.N., et al., "Cellular and molecular mechanisms of liver tolerance," Immunological reviews, 2006. 213: p. 101-18.

Epstein, J.E., et al., "Live attenuated malaria vaccine designed to protect through hepatic CD8(+) T cell immunity," Science, 2011. 334(6055): p. 475-80.

Estcourt, M.J., et al., "Prime-boost immunization generates a high frequency, high-avidity CD8(+) cytotoxic T lymphocyte population," International immunology, 2002. 14(1): p. 31-7.

Ewer, K.J., et al., "Protective CD8+ T-cell immunity to human malaria induced by chimpanzee adenovirus-MVA immunisation," Nature communications, 2013. 4: p. 2836.

"Global. WHO declares emergency against AIDS, TB, malaria," AIDS policy & law, 2006. 21(9): p. 5.

Guebre-Xabier, M., R. Schwenk, and U. Krzych, "Memory phenotype CD8(+) T cells persist in livers of mice protected against malaria by immunization with attenuated Plasmodium berghei sporozoites," Eur J Immunol, 1999. 29(12): p. 3978-86.

Hill, A.V., et al., "Prime-boost vectored malaria vaccines: progress and prospects," Human vaccines, 2010. 6(1): p. 78-83.

Jung, S., et al., "In vivo depletion of CD11c+ dendritic cells abrogates priming of CD8+ T cells by exogenous cell-associated antigens," Immunity, 2002. 17(2): p. 211-20.

Kasturi, S.P., et al., "Programming the magnitude and persistence of antibody responses with innate immunity," Nature, 2011. 470(7335): p. 543-7.

Le Gall et al., "Portable flanking sequences modulate CTL epitope processing," J Clin Invest. 2007; 117:3563-75.

Li, S., et al., "Priming with recombinant influenza virus followed by administration of recombinant vaccinia virus induces CD8+ T-cell-mediated protective immunity against malaria," Proceedings of the National Academy of Sciences of the United States of America, 1993. 90(11): p. 5214-8.

Lim, K., et al., "Neutrophil trails guide influenza-specific CD8(+) T cells in the airways," Science, 2015. 349(6252): p. aaa4352.

Longley, R.J. et al., "Comparative assessment of vaccine vectors encoding ten malaria antigens identifies two protective liver-stage candidates," Sci Rep, 2015. 5: p. 11820.

Longley, R.J., et al., "Identification of Immunodominant Responses to the Plasmodium falciparum Antigens PfUIS3, PfLSA1 and PfLSAP2 in Multiple Strains of Mice," PLoS One, 2015. 10(12): p. e0144515.

Ma, C., et al., "Production, characterisation and immunogenicity of a plant-made Plasmodium antigen—the 19 kDa C-terminal fragement of Plasmodium yoelii merozoite surface protein 1.," Appl Microbiol Biot. 2012;94(1):151-161.

Marsh, K. and S. Kinyanjui, "Immune effector mechanisms in malaria," Parasite immunology, 2006. 28(1-2): p. 51-60.

McConkey, S.J., et al., "Enhanced T-cell immunogenicity of plasmid DNA vaccines boosted by recombinant modified vaccinia virus Ankara in humans," Nature Medicine, 2003. 9(6): p. 729-735.

McShane, H., et al., "Recombinant modified vaccinia virus Ankara expressing antigen 85A boosts BCG-primed and naturally acquired antimycobacterial immunity in humans," Nat Med, 2004. 10(11): p. 1240-4.

Mohammad, A.K. and J.J. Reineke, "Quantitative detection of PLGA nanoparticle degradation in tissues following intravenous administration," Molecular pharmaceutics, 2013. 10(6): p. 2183-9.

Mueller, S.N., et al., "Memory T cell subsets, migration patterns, and tissue residence," Annu Rev Immunol, 2013. 31: p. 137-61.

Murphy, S.C., et al., "A T-cell response to a liver-stage Plasmodium antigen is not boosted by repeated sporozoite immunizations," Proceedings of the National Academy of Sciences of the United States of America, 2013. 110(15): p. 6055-60.

Murray, C.J., et al., "Global, regional, and national incidence and mortality for HIV, tuberculosis, and malaria during 1990-2013: a systematic analysis for the Global Burden of Disease Study 2013," Lancet, 2014. 384(9947): p. 1005-70.

Neafsey, D.E., et al., "Genetic Diversity and Protective Efficacy of the RTS,S/AS01 Malaria Vaccine," The New England journal of medicine, 2015.

Ogwang, C., et al., "Prime-boost vaccination with chimpanzee adenovirus and modified vaccinia Ankara encoding TRAP provides partial protection against Plasmodium falciparum infection in Kenyan adults," Sci Transl Med, 2015. 7(286): p. 286re5.

Park, S.H., et al., "Phase 1b Trial of Biweekly Intravenous Pexa-Vec (JX-594), an Oncolytic and Immunotherapeutic Vaccinia Virus in Colorectal Cancer," Mol Ther, 2015. 23(9): p. 1532-40.

Pearson et al., "Induction of CD8+ T cell responses and protective efficacy following microneedle-mediated delivery of a live adenovirus-vectored malaria vaccine," Vaccine, 2015. 33: p. 3248-3255.

Plenbanski et al., "Protection from Plamodium berghei infection by priming and boosting T cells to a single class I-restricted epitope with recombinant carriers suitable for human use," Eur. J. Immonol., 1998. 28: p. 4345-4355.

Protzer, U., M.K. Maini, and P.A. Knolle, "Living in the liver: hepatic infections," Nat Rev Immunol, 2012. 12(3): p. 201-13.

Radtke, A.J., S.W. Tse, and F. Zavala, "From the draining lymph node to the liver: the induction and effector mechanisms of malaria-specific CD8+ T cells," Semin Immunopathol, 2015. 37(3): p. 211-20.

Rampling, T., et al., "A Monovalent Chimpanzee Adenovirus Ebola Vaccine—Preliminary Report," N Engl J Med, 2015.

Reyes-Sandoval, A., et al., "CD8+ T effector memory cells protect against liver-stage malaria," Journal of immunology, 2011. 187(3): p. 1347-57.

Reyes-Sandoval, A., et al., "Prime-boost immunization with adenoviral and modified vaccinia virus Ankara vectors enhances the durability and polyfunctionality of protective malaria CD8+ T-cell responses," Infection and immunity, 2010. 78(1): p. 145-53.

Reyes-Sandoval, A., et al., "Single-dose immunogenicity and protective efficacy of simian adenoviral vectors against Plasmodium berghei," Eur J Immunol, 2008. 38(3): p. 732-41.

Rollier, C.S., et al., "Viral vectors as vaccine platforms: deployment in sight," Curr Opin Immunol, 2011. 23(3): p. 377-82.

Romero, P., et al., "Cloned cytotoxic T cells recognize an epitope in the circumsporozoite protein and protect against malaria," Nature, 1989. 341(6240): p. 323-6.

Schenkel, J.M. and D. Masopust, "Tissue-resident memory T cells," Immunity, 2014. 41(6): p. 886-97.

Schenkel, J.M., et al., "T cell memory. Resident memory CD8 T cells trigger protective innate and adaptive immune responses," Science, 2014. 346(6205): p. 98-101.

Schmidt, N.W., et al., "Extreme CD8 T cell requirements for anti-malarial liver-stage immunity following immunization with radiation attenuated sporozoites," PLoS pathogens, 2010. 6(7): p. e1000998.

(56) References Cited

OTHER PUBLICATIONS

Schmidt, N.W., et al., "Memory CD8 T cell responses exceeding a large but definable threshold provide long-term immunity to malaria," Proceedings of the National Academy of Sciences of the United States of America, 2008. 105(37): p. 14017-22.

Schneider, J., et al., "Enhanced immunogenicity for CD8+ T cell induction and complete protective efficacy of malaria DNA vaccination by boosting with modified vaccinia virus Ankara," Nature, 1998 4(4): p. 397-402.

Schofield, L., et al., "Gamma interferon, CD8+ T cells and antibodies required for immunity to malaria sporozoites," Nature, 1987. 330(6149): p. 664-6.

Seder, R.A. and A.V. Hill, "Vaccines against intracellular infections requiring cellular immunity," Nature, 2000. 406(6797): p. 793-8.

Shin, H. and A. Iwasaki, "A vaccine strategy that protects against genital herpes by establishing local memory T cells," Nature, 2012. 491(7424): p. 463-7.

Small, E.J., et al., "A phase I trial of intravenous CG7870, a replication-selective, prostate-specific antigen-targeted oncolytic adenovirus, for the treatment of hormone-refractory, metastatic prostate cancer," Mol Ther, 2006. 14(1): p. 107-17.

Stary, G., et al., "A mucosal vaccine against Chlamydia trachomatis generates two waves of protective memory T cells," Science, 2015. 348(6241): p. aaa8205.

Tian, J.H., et al., "Definition of T cell epitopes within the 19 kDa carboxylterminal fragment of Plasmodium yoelii merozoite surface protein 1 (MSP1(19)) and their role in immunity to malaria,". Parasite Immunol. Jun. 1998;20(6):263-78.

Tse, S.W., et al., "The chemokine receptor CXCR6 is required for the maintenance of liver memory CD8(+) T cells specific for infectious pathogens," J Infect Dis, 2014. 210(9): p. 1508-16.

Weiss, W.R., et al., "CD8+ T cells (cytotoxic/suppressors) are required for protection in mice immunized with malaria sporozoites," Proceedings of the National Academy of Sciences of the United States of America, 1988. 85(2): p. 573-6.

Gola, et al., "Prime and target immunization protects against liver-stage malaria in mice", Sci, Transl, Med., 10, eaap9128(2018), Sep. 26, 2018, pp. 1-11.

Gola, A. et al., Prime and target immunization protects against liver-stage malaria in mice, Sci. Transl. Med., 10, eaap9128 (2018), pp. 1-11.

Gola, A. et al., Prime and target immunization protects against liver-stage malaria in mice, Sci. Transl. Med., 10, eaap9128 (2018), pp. 1-24, Supplementary Materials.

Zhang, L., et al., Effect of Vaccine Administration Modality on Immunogenicity and Efficacy, Expert Rev Vaccines. 2015; 14(11): 1509-1523.

\* cited by examiner

FIG. 1 continued
b
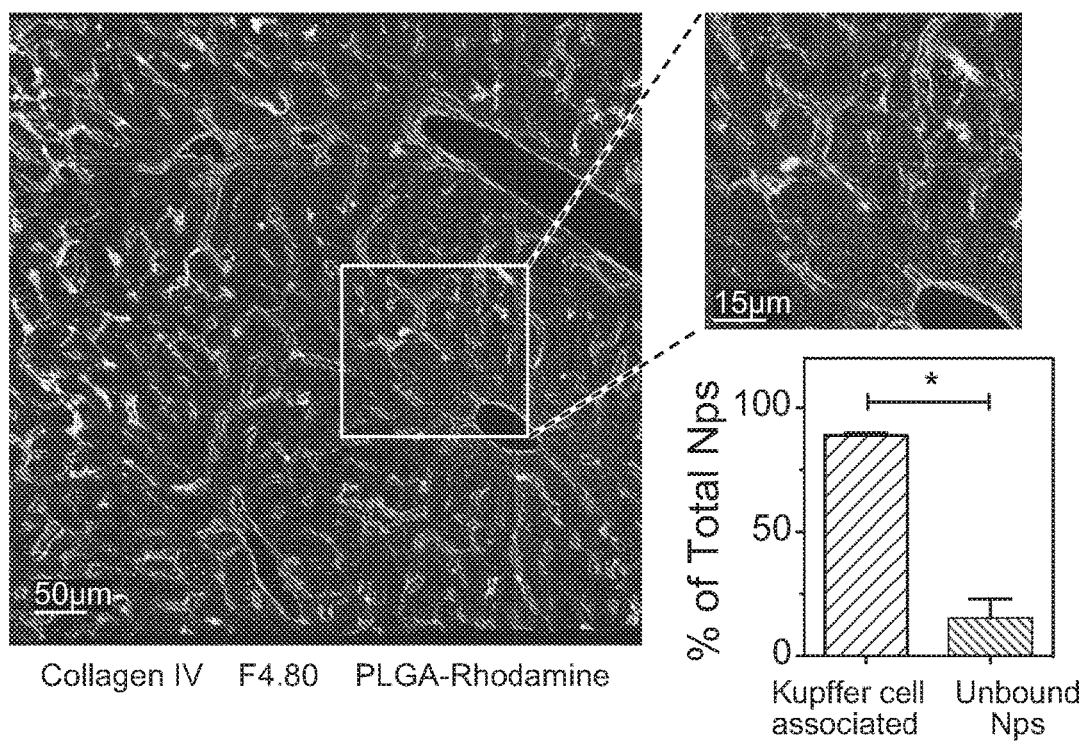
c
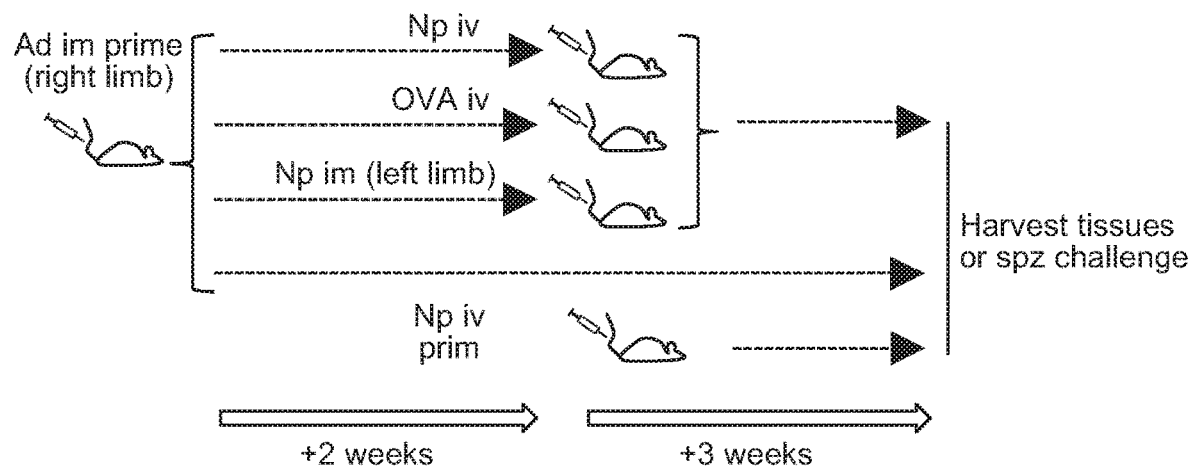

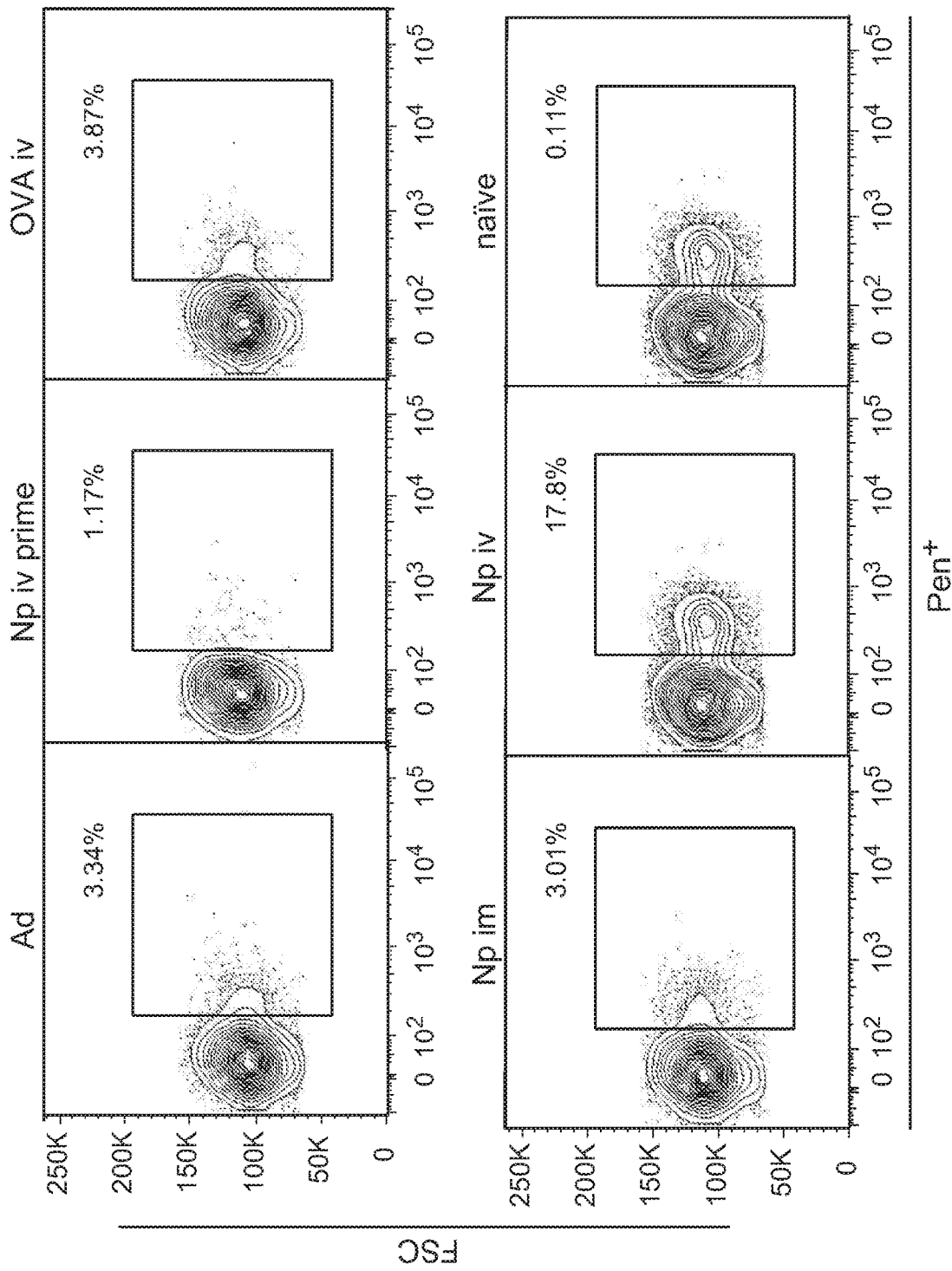
FIG. 2 continued B

FIG. 3
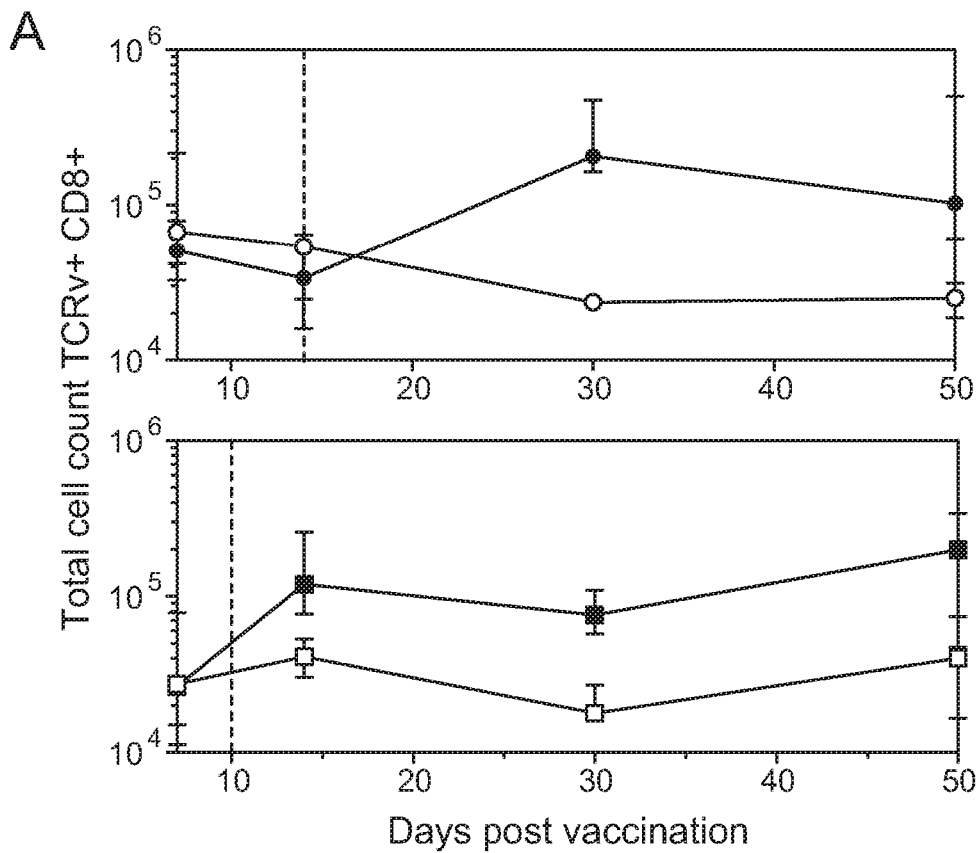
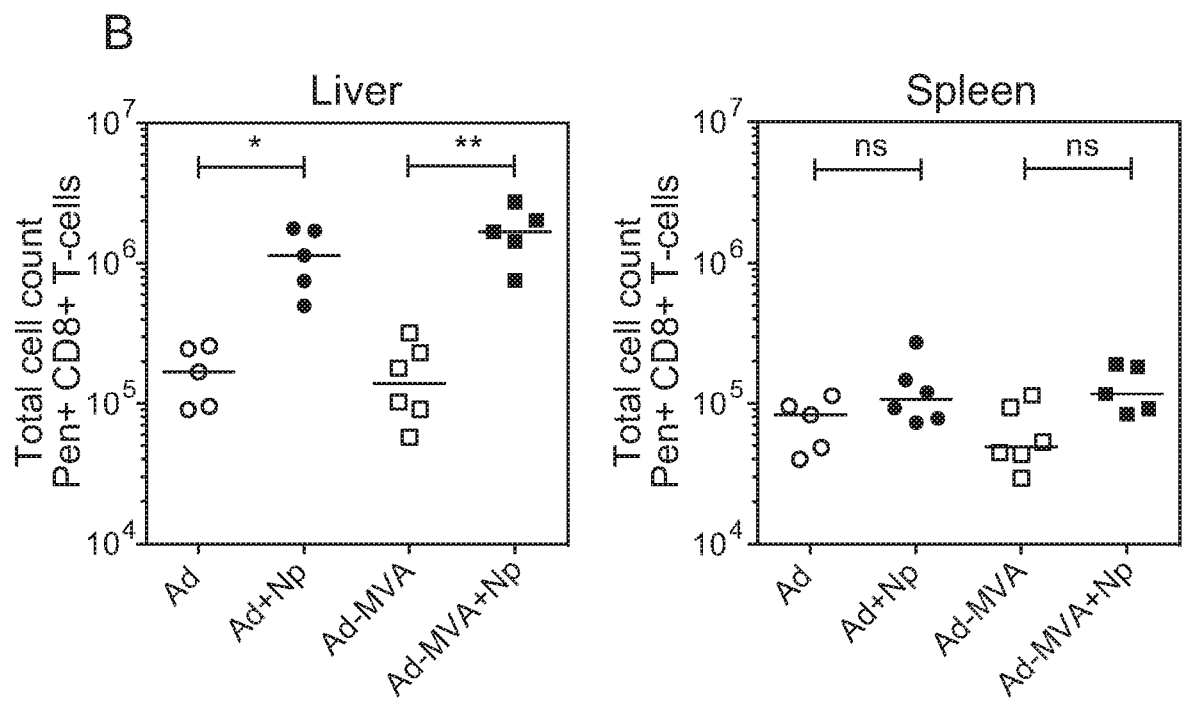

FIG. 4
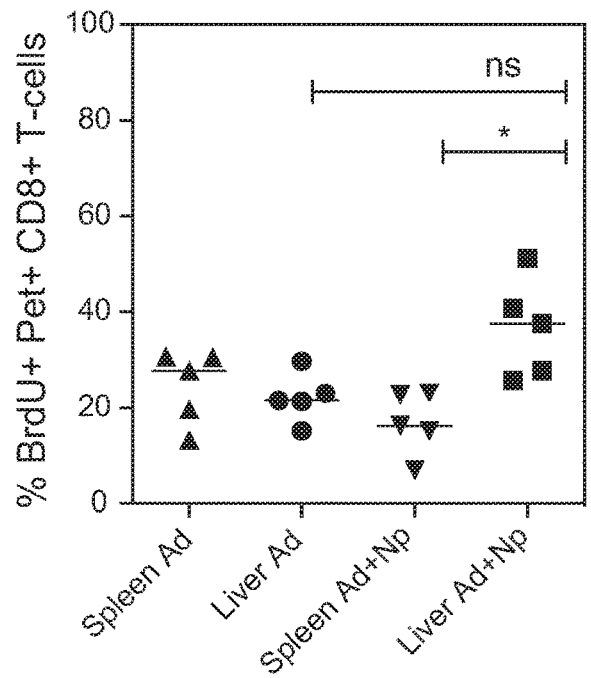
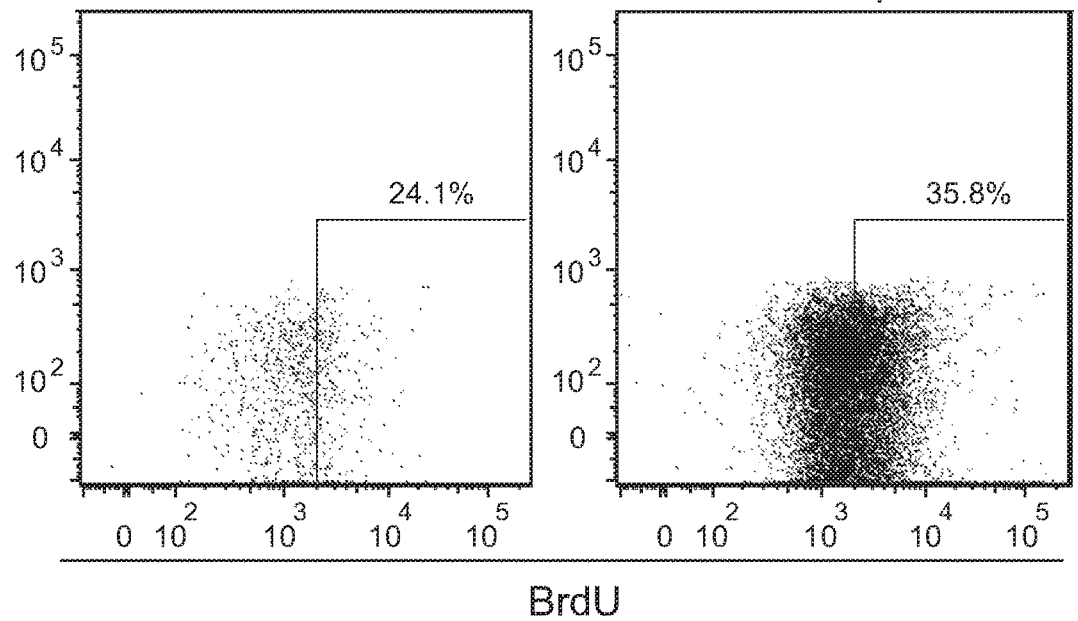
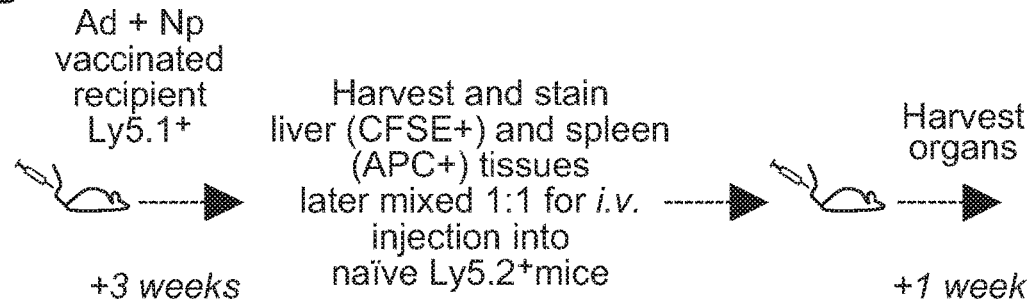

FIG. 4 continued
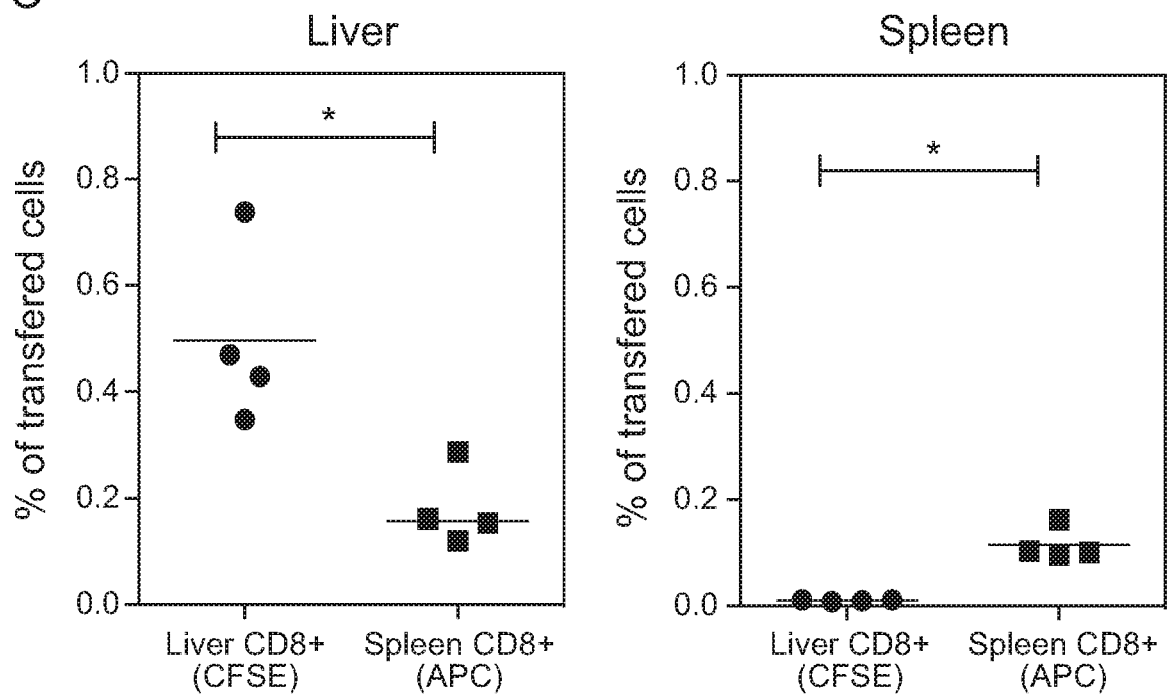
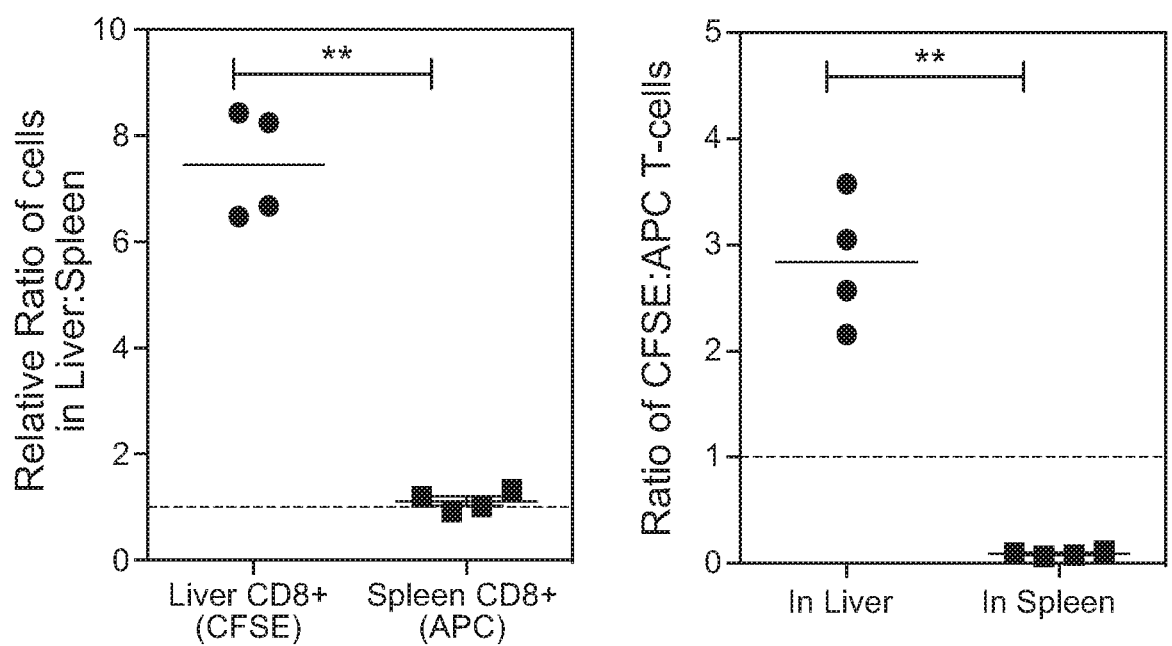

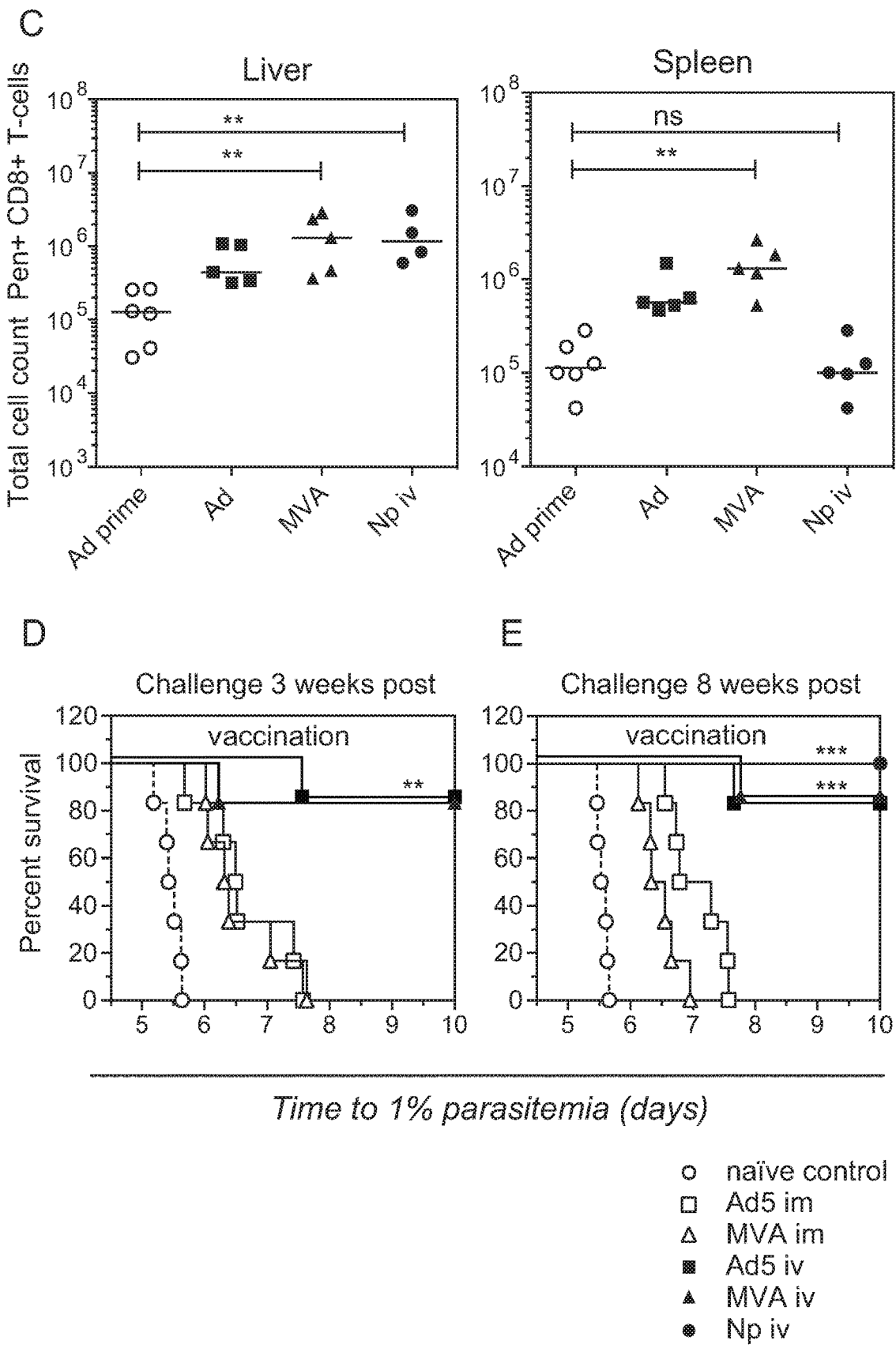

FIG. 14
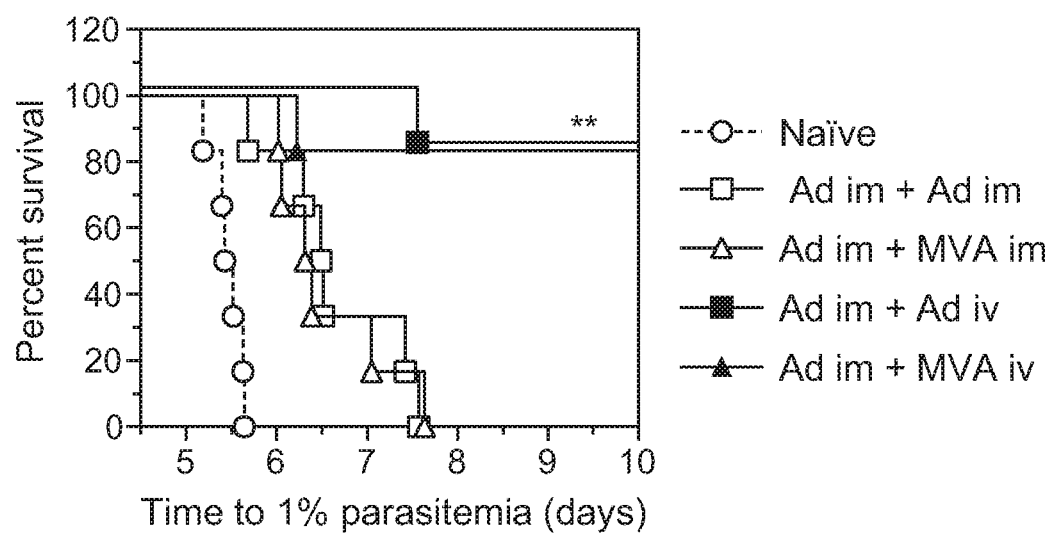
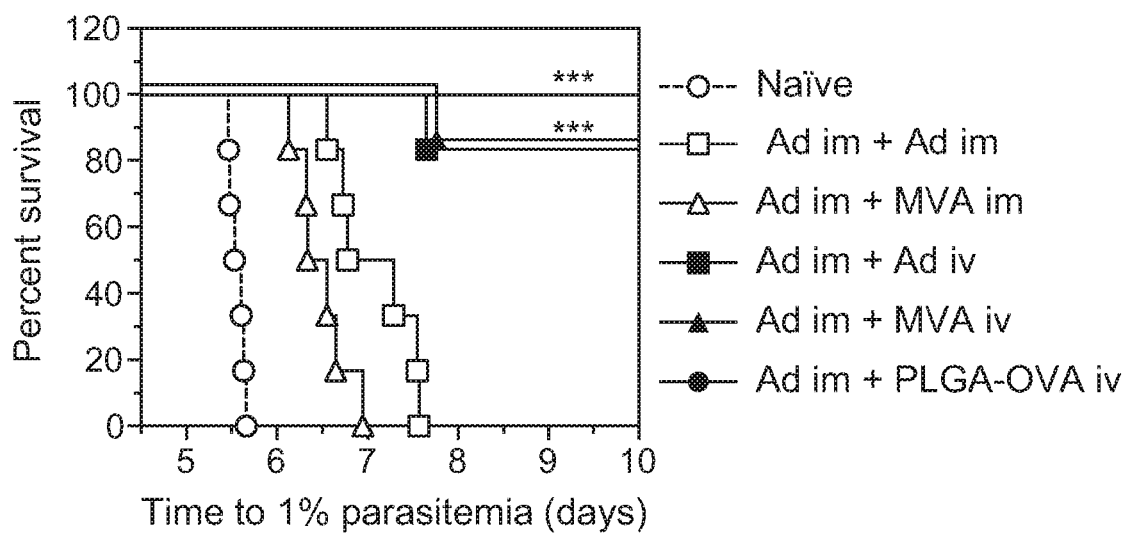
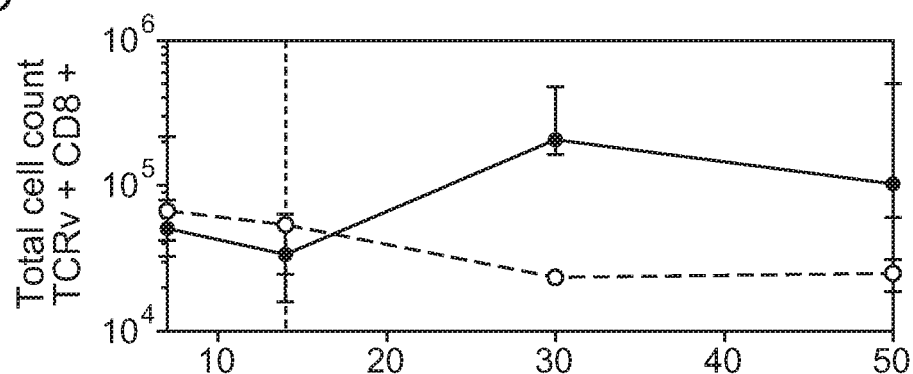

A — Total number of IFNg+ CD8 T-cells in Liver
B — % of IFNg+ CD8 T-cells in Liver FIG. 19 (Suppl Fig 1)
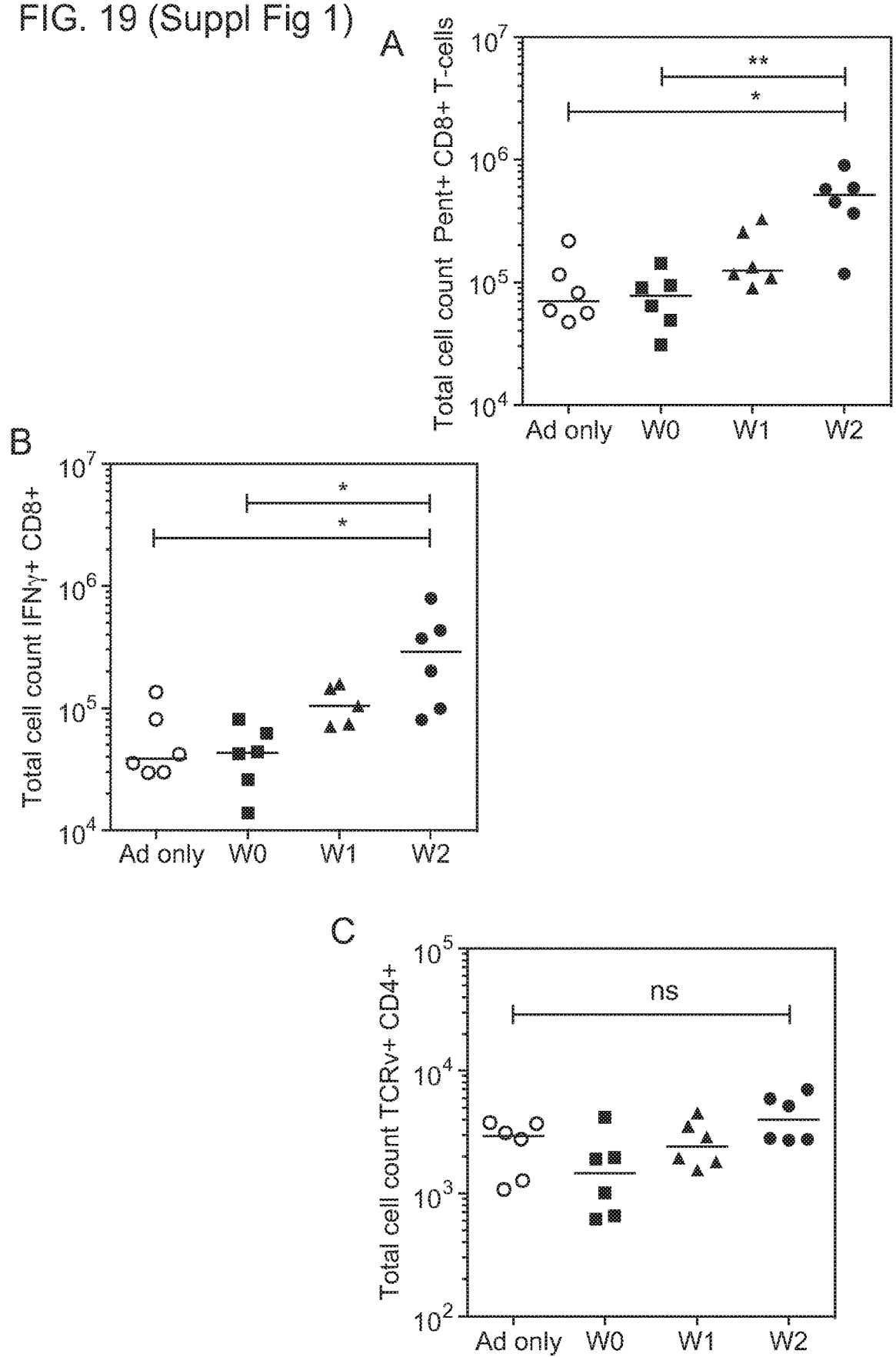

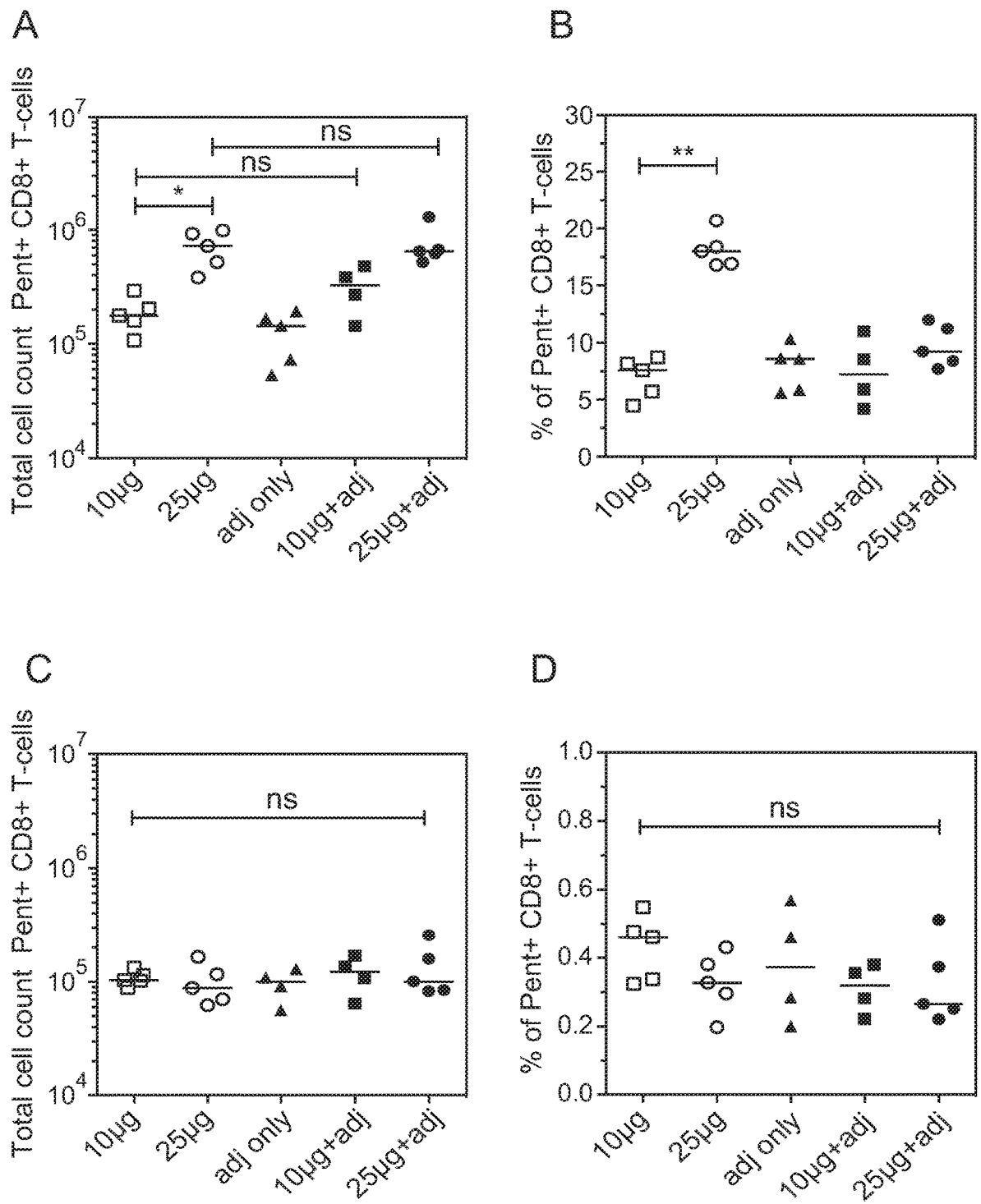
FIG. 20 (Suppl Fig 2)

FIG. 21 (Suppl Fig 3)
A
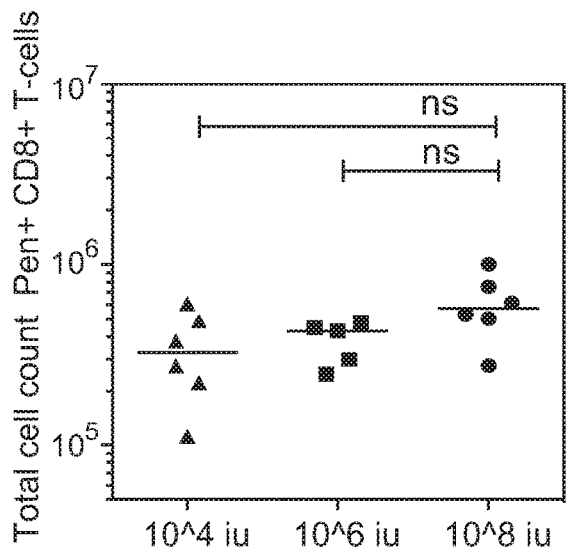
B
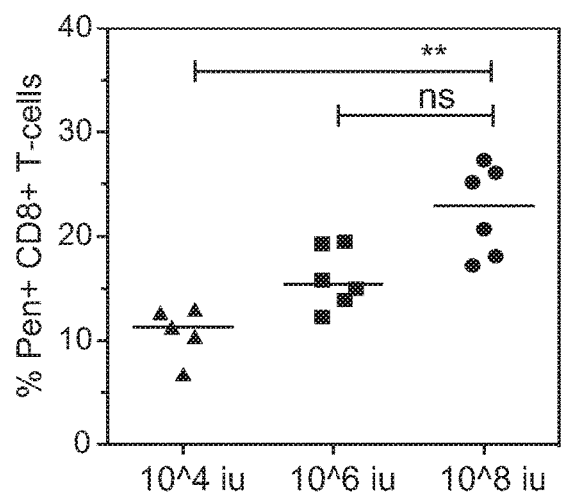
C
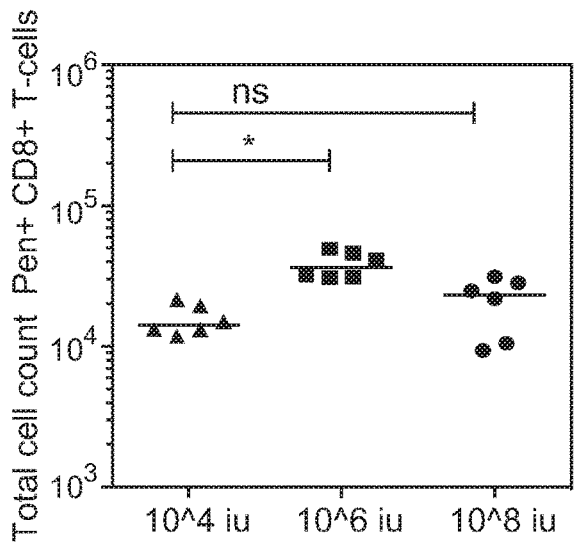
D
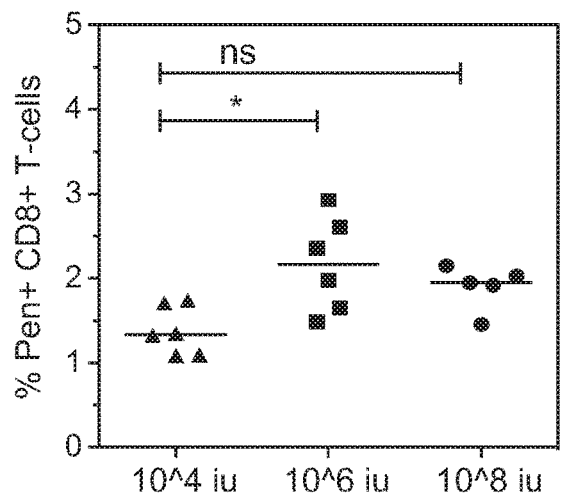

FIG. 22 (Suppl Fig 4)
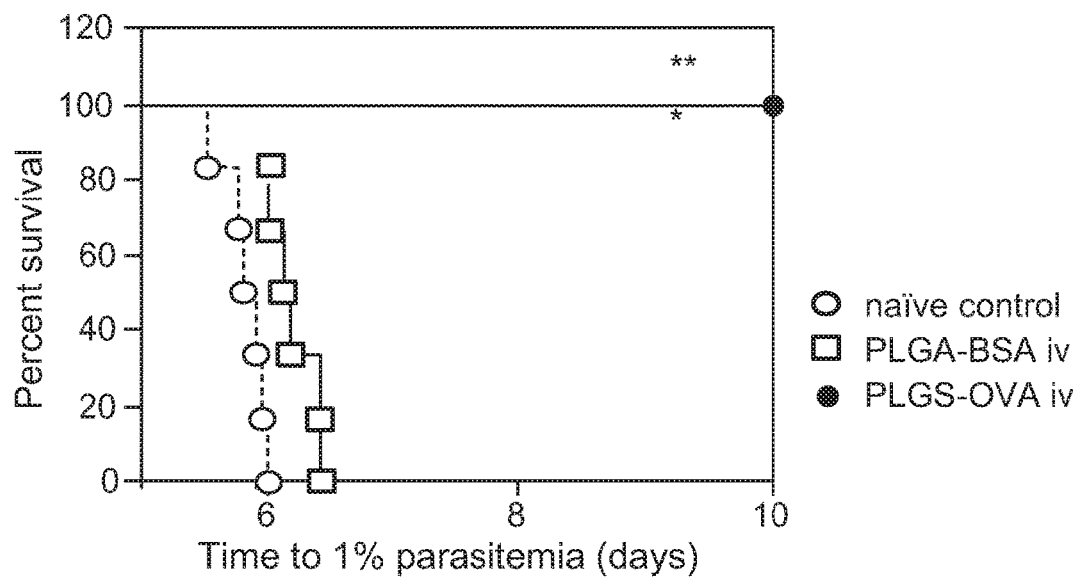
FIG. 23 (Suppl Fig 5)
A
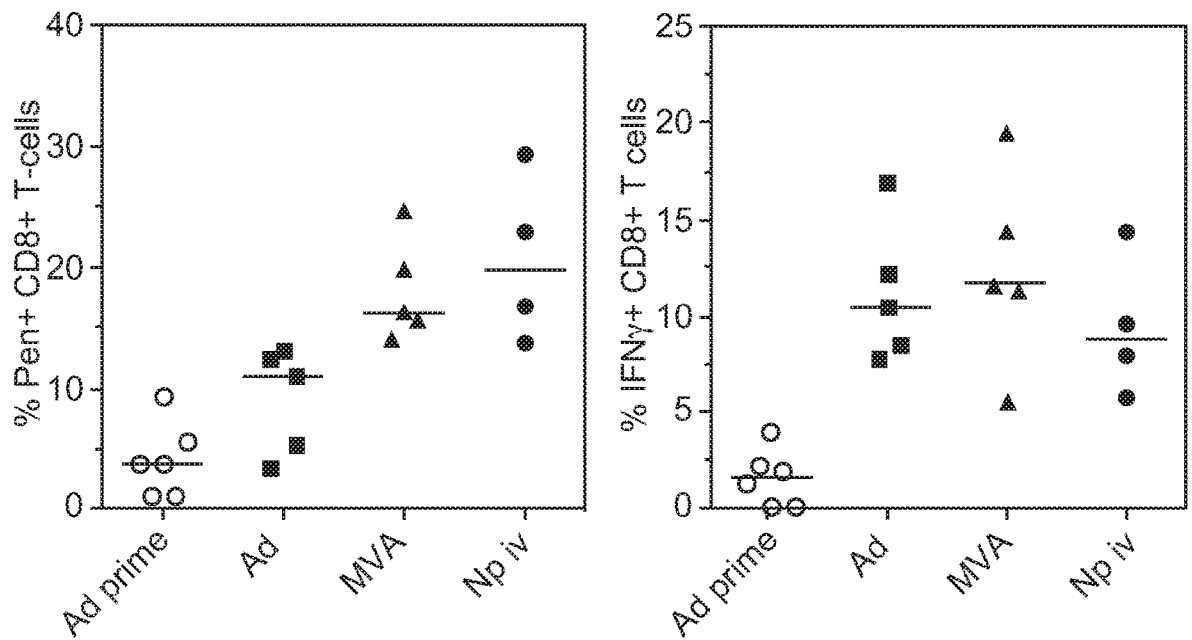

FIG. 23 (Suppl Fig 5) continued
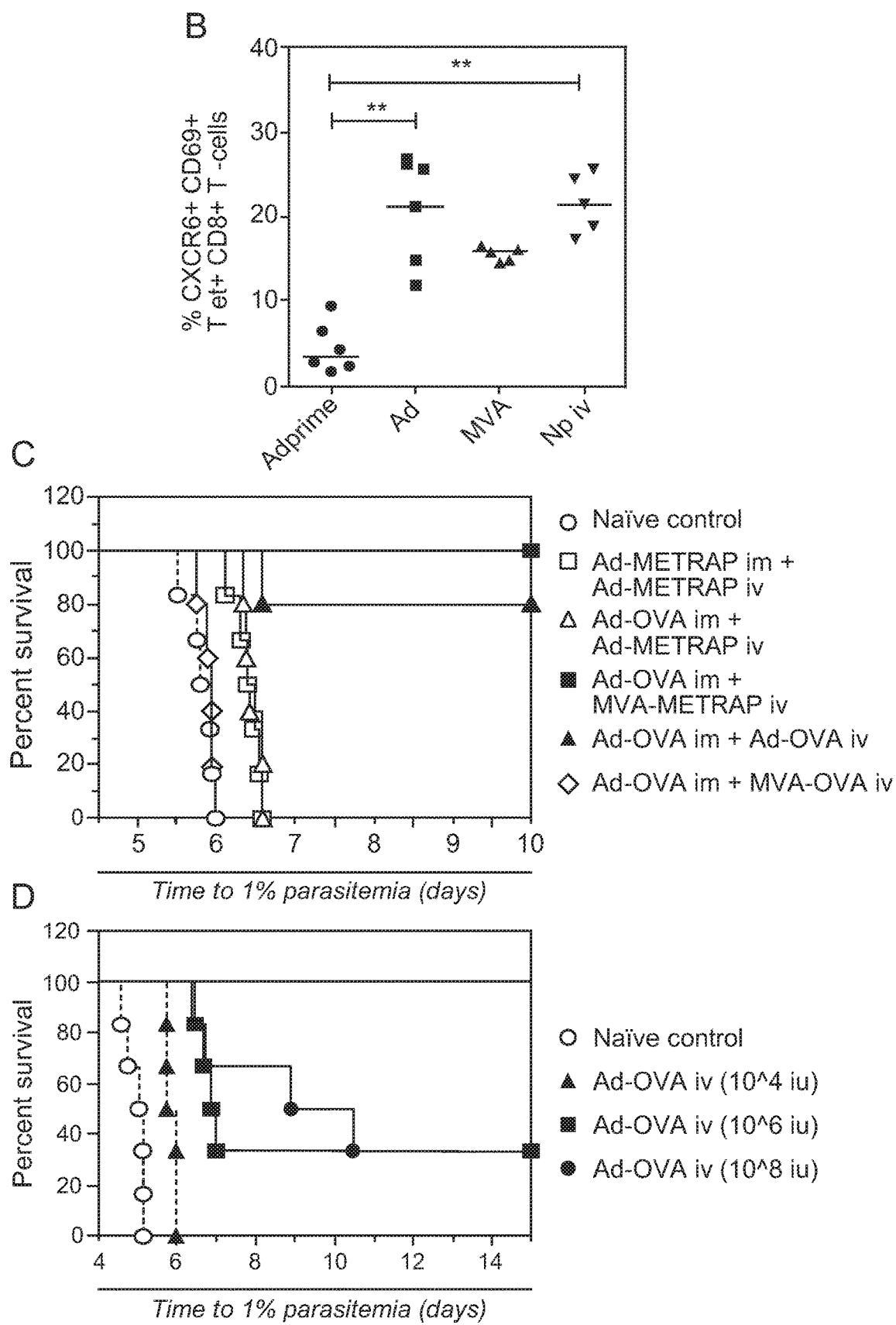

FIG. 24 (Suppl Fig 6)
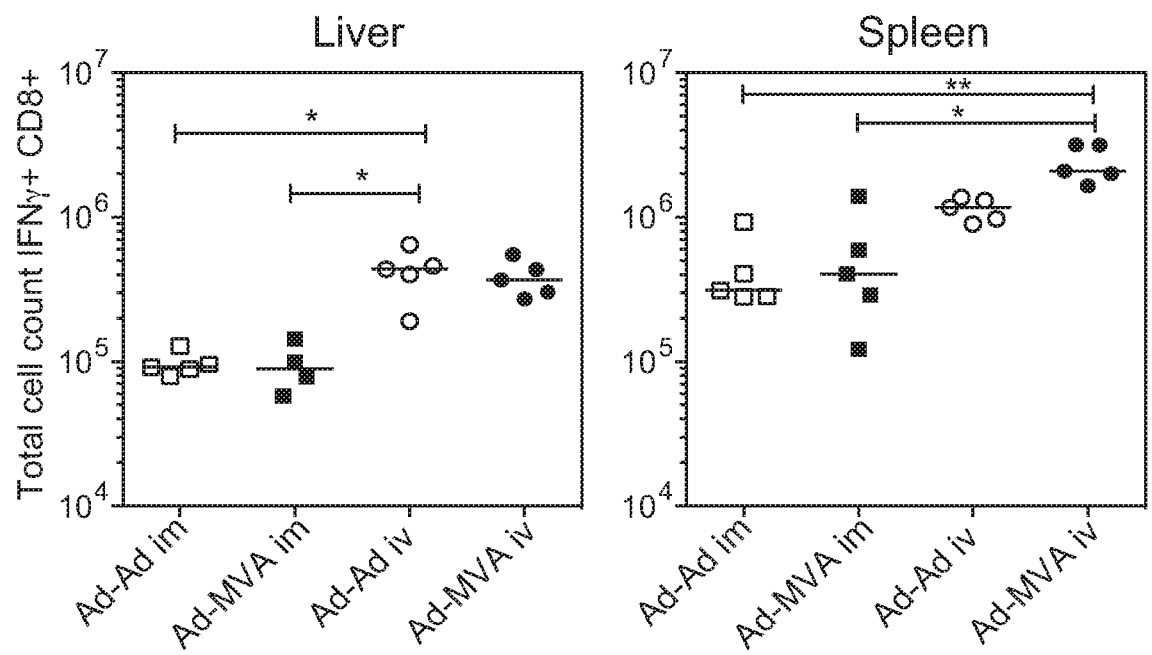
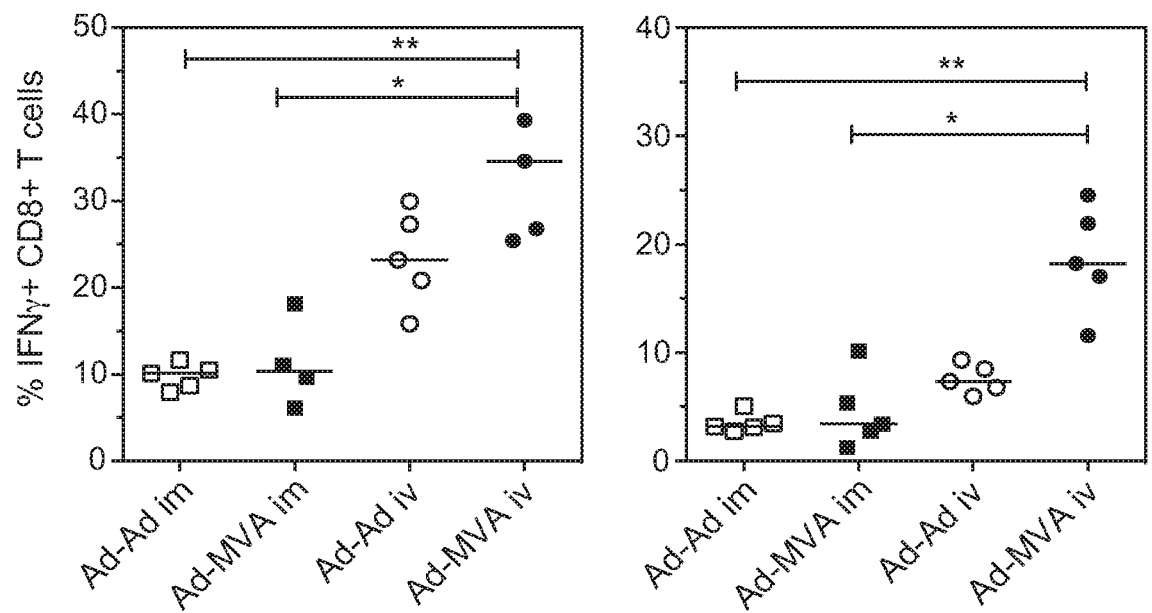

FIG. 25 (Suppl Fig 7)
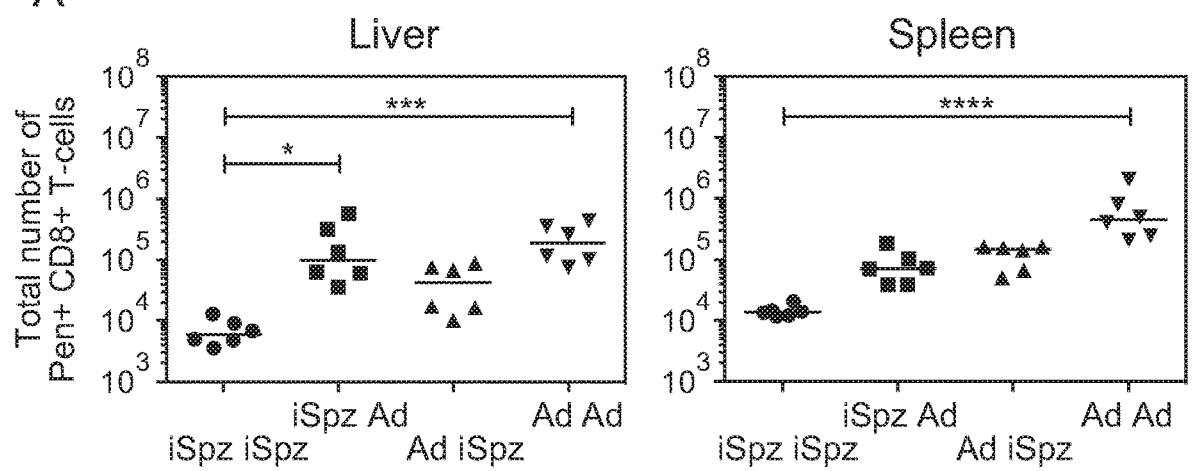
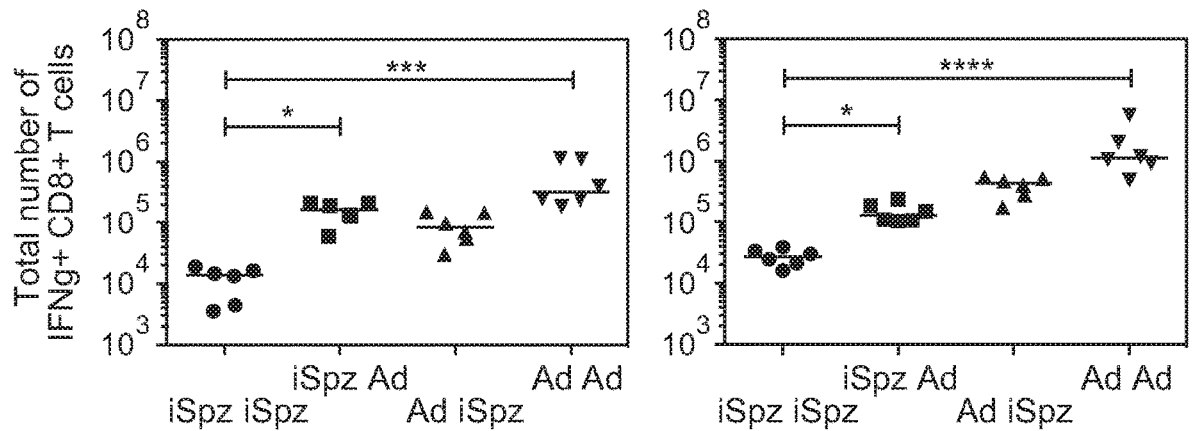

PRIME TARGET

RELATED APPLICATIONS

The present application is a national phase application, filed under 35 U.S.C. § 371, of PCT/GB2017/051009, filed Apr. 11, 2017, which claims priority benefit of GB 1606271.3, filed Apr. 12, 2016, GB 1607503.8, filed Apr. 29, 2016 and GB 1607506.1, filed Apr. 29, 2016, the disclosure of each of which is incorporated fully herein by reference.

FIELD OF THE INVENTION

The invention is in the field of targeted immune responses, in particular immune responses which are targeted to the liver.

BACKGROUND

The induction of antigen specific T-cells is believed to be important for protection against a number of intracellular pathogens, such as Human Immunodeficiency Virus (HIV), *Mycobacterium tuberculosis* (Mtb), *Plasmodium* species, *Leishmania* and other viral pathogens. In addition to infectious diseases, cellular adaptive immunity is also important for the clearance of tumours expressing tumour-associated antigens. It has therefore been the goal of many novel vaccine strategies to generate high numbers of memory $CD8^+$ T-cells aimed at killing infected cells.

Heterologous prime-boost vaccination with virally vectored vaccines has been shown to be one of the most effective strategies at generating high numbers of circulating T lymphocytes. A vaccination regimen composed of an intramuscular (i.m.) Adenovirus (Ad) prime followed by Modified Vaccinia Ankara (MVA) i.m. boost is able to markedly increase the total number of antigen-specific (Ag-specific) T-cells in circulation as well as their affinity, allowing them to recognize target cells expressing very low levels of antigen (Estcourt, M. J., et al., Prime-boost immunization generates a high frequency, high-avidity CD8(+) cytotoxic T lymphocyte population. International immunology, 2002. 14(1): p. 31-7). This strategy has been successful in generating only a partial level of protective immunity both in pre-clinical and human clinical trials for a variety of diseases.

Malaria, caused by *Plasmodium* species, is one of the most important infectious diseases world-wide, associated with high morbidity and mortality especially in sub-Saharan African children under the age of five. With growing anti-malarial drug and insecticide resistance, an effective vaccination regimen with high efficacy is urgently needed. A variety of different subunit vaccine strategies have been investigated, aimed at different stages of the *Plasmodium* life cycle, with the greatest success observed to date with sporozoite and liver-stage malaria candidates. Specifically RTS,S/AS01, a protein in adjuvant formulation inducing antibodies against the circumsporozoite (CS) protein, completed Phase III field trials with partial efficacy but has yet to achieve WHO pre-qualification.

An alternative approach to induce protection against the pre-erythrocytic stage of malaria has been to generate cellular immunity directed against infected hepatocytes.

The ability of interferon-$\gamma^+$ (IFN$\gamma$) $CD8^+$ T-cells to protect against liver stage malaria in mice has been demonstrated. To this end, substantial effort has been invested in optimizing a viral vector, heterologous prime-boost strategy able to generate high frequencies of antigen (Ag) specific $CD8^+$ T-cells. The most promising regime in both pre-clinical and clinical studies comprises an Adenovirus (Ad) viral vector prime, which is subsequently boosted with Modified Vaccinia Ankara (MVA) expressing the same antigen. This strategy has been employed clinically for a number of diseases in addition to malaria, such as Ebola, *M. tuberculosis*, HIV and influenza. Vaccination with a heterologous prime-boost Ad and MVA expressing TRAP can induce high numbers of circulating malaria specific $CD8^+$ T-cells with some degree of clinical efficacy in both malaria naïve and pre-exposed individuals. But to achieve greater levels of efficacy, it is most likely that higher numbers of circulating $CD8^+$ T cells will be required, as is the case in mice.

Despite the substantial progress that has been made over the last 20 years, vaccines aimed at inducing cell-mediated immunity against malaria may have been hindered by a number of challenging spatio-temporal factors pertaining both to parasite biology and liver microanatomy. Thus, a highly effective vaccine against malaria is still urgently needed, with leading vaccination strategies targeting primarily the pre-erythrocytic, sporozoite and liver stages of the *Plasmodium* life cycle. Cytotoxic antigen specific CD8+ T-cells producing high levels of interferon-$\gamma$ are known to be protective, with heterologous prime-boost viral vector immunization being a particularly effective method of induction. Thus, it has been a major research goal to develop a high efficacy malaria vaccine, particularly through the induction of protective CD8+ T cell immunity against the liver-stage of *P. falciparum* infection. Viral vectors have been developed, based on chimpanzee adenovirus (ChAd) and MVA, that have been used safely in over a thousand vaccinees for malaria, induce very high numbers of circulating T cells, and provide partial efficacy in phase II clinical trials in the UK and Africa. However, this vaccination approach, which induces exceptionally high numbers of circulating CD8+ T cells that are required for and correlate with efficacy, still only provides partial protection against sporozoite challenge in mice and humans (20-30% sterile efficacy against heterologous strains in controlled human malaria infections). This is a problem in the art.

There have been some prior attempts to localize T-cell responses, especially to mucosal surfaces, and many attempts to induce mucosal immunity by immunizing at mucosal sites. However, this approach has met with limited success.

It has been a research challenge for many years to induce a cellular immune response in the liver. This is an exceptionally challenging effect to produce.

Prior art attempts to provide protection for certain types of liver disease have successfully produced high levels of response in the blood. For example, the inventors' own work in immunising subjects to achieve high immune responses have led the field. However, despite these "best in class" immunisation results, still only approximately 20 to 25% protection is seen for diseases such as Malaria. Thus, prior art approaches have demanded very high circulating T-cell responses in order to achieve meaningful protection. This is a problem in the art.

Viruses, which have been used as viral vectors, include, but are not limited to, Ad, MVA, Vaccinia, other poxviruses, Adenovirus-Associated Viruses, Flaviviruses, Herpes viruses, and Alpha viruses. However, there is a growing body of evidence suggesting that the generation of high numbers of circulating T-cells may still not be sufficient to protect if the responses are not spatially linked to the site or portal of infection.

Importantly, a new subset of memory lymphocytes, called Tissue-Resident T-lymphocytes ($T_{RM}$) has been recently described. $T_{RM}$ comprise a non-recirculating memory T-cell population remaining positioned in non-lymphatic tissues such as the mucosal tissues, skin and internal organs such as the brain, kidney, pancreas and liver. Although a highly heterogeneous population, varying between different organs, in many cases when $T_{RM}$ are present at the site of re-infection they are able to accelerate protection against secondary pathogen exposure, serving in part as early tissue sentinels. However, a reliable means of robust induction of such tissue resident memory T cells by vaccination has not been known, which is a problem in the art.

The present invention seeks to overcome problem(s) associated with the art.

SUMMARY OF THE INVENTION

The inventors studied T-cells in various physical locations around the body. For example, T-cells were studied by staining in lymph nodes and other discrete locations.

The inventors were interested in studying and improving immunisation regimes. Conventionally, intramuscular and other administration routes were employed. However, suddenly when the inventors experimented with intravenous (I.V.) and later subcutaneous (s.c.) administration they surprisingly achieved remarkable results. In particular, by providing an I.V. second ("target") immunisation, remarkably effective results were achieved including 100% protection from malarial disease.

The liver is especially difficult to induce and/or maintain immune responses in, since it is known to be an immune tolerant organ. Therefore, it is even more surprising that the inventors have achieved their robust results in generating an immune response targeted to the liver.

It is a surprise that the methods of the invention result in generation of T-cells localised to a particular area such as the liver. It is further surprising that those T-cells remain in that location such as the liver and exert their effects there.

Thus in one aspect the invention provides a kit comprising at least a first composition and a second composition, each said first and second compositions comprising at least one epitope of a liver disease antigen, wherein said epitope is a CD8+ T cell epitope, for use in induction of an immune response in the liver of a mammalian subject by administration of said first composition by intramuscular (i.m.), subcutaneous (s.c.), intradermal (i.d.), oral or aerosol route, and administration of said second composition by intravenous (i.v.), subcutaneous (s.c.) or oral route, characterised in that said first and second compositions are administered by different routes.

In one aspect, the invention relates to a method of inducing an immune response in the liver of a mammalian subject, said method comprising administering a first composition and a second composition to said subject, each said first and second compositions comprising at least one epitope of a liver disease antigen, wherein said epitope is a CD8+ T cell epitope,
wherein administration of said first composition is by intramuscular (i.m.), subcutaneous (s.c.), intradermal (i.d.), oral or aerosol route, and administration of said second composition is by intravenous (i.v.), subcutaneous (s.c.) or oral route, characterised in that said first and second compositions are administered by different routes.

In one aspect, the invention relates to use of a kit as described above in the treatment or prevention of liver disease.

In one aspect, the invention relates to a kit as described above, a method as described above, or a use as described above, wherein said second composition is administered about 2 weeks after administration of said first composition.

Suitably said second composition is administered intravenously or subcutaneously, preferably intravenously.

Suitably said first composition is administered intramuscularly.

Suitably said first composition is administered intramuscularly and said second composition is administered intravenously.

Suitably said first composition comprises a particulate or particle-bound epitope, or a viral vector encoding said epitope, said viral vector being selected from the group consisting of: adenoviral vector or poxviral vector.

Suitably said second composition comprises a particulate or particle-bound epitope, or a viral vector encoding said epitope, said viral vector being selected from the group consisting of: adenoviral vector or poxviral vector.

Suitably said first composition comprises an adenoviral vector encoding said epitope, and said second composition comprises a poxvirus vector encoding said epitope.

Suitably said first composition comprises a simian or human adenoviral vector encoding said epitope, and said second composition comprises a Modified Virus Ankara (MVA) poxvirus vector encoding said epitope.

Most suitably said simian or human adenoviral vector comprises an Ad5 adenoviral vector.

Suitably the immune response is a CD8+ cytotoxic T cell (CTL) response.

Suitably said at least one epitope of said first and second compositions is from the same liver disease antigen.

Suitably the at least one epitope in said first and second compositions are the same.

Suitably said first and second compositions are different.

Suitably said first and second compositions are the same.

When the first and second compositions are the same suitably the second composition is administered before anti-vector immunity takes place in the subject. Of course the skilled worker will appreciate that different routes of administration might require compositions having different formulations (e.g. due to dose/volume) but may use compositions having the same formulation for different routes of administration if appropriate.

Suitably the antigen is selected from the group consisting of: a malarial antigen, a *P. falciparum* antigen, a *Plasmodium vivax* antigen, a *P. knowlesi* antigen, a *P. berghei* antigen, a Hepatitis virus antigen, a Hepatitis A virus antigen, a Hepatitis B virus antigen, a Hepatitis C virus antigen, and a Hepatitis E virus antigen.

Suitably the malarial parasite is *P. falciparum, P. vivax*, or *P. knowlesi*.

In one aspect, the invention relates to a device for administration of a composition as described above, said device comprising at least one dose of said composition(s).

In one aspect, the invention relates to a kit comprising a first container and a second container, each said container containing a composition comprising at least one epitope of a liver disease antigen, wherein said epitope is a CD8+ T cell epitope, for inducing an immune response in a subject, wherein said first container and said second container are used to administer said composition to said subject by different routes.

In one aspect, the invention relates to use of a kit as described above in induction of an immune response in a subject, wherein the compositions of said kit are administered to said subject.

In one aspect, the invention relates to a method of making a kit as described above, the method comprising selecting at least one epitope of a liver disease antigen, mixing said epitopes together with a pharmaceutically acceptable carrier, and formulating a first composition suitable for administration by intramuscular (i.m.), subcutaneous (s.c.), intradermal (i.d.), oral or aerosol route, preferably intramuscular (i.m.) route, and formulating a second composition suitable for administration by intravenous (i.v.), subcutaneous (s.c.) or oral route, preferably intravenous (i.v.) or subcutaneous (s.c.), route, most preferably intravenous (i.v.) route, characterised in that said first and second compositions are formulated for administration by different routes.

In one aspect, the invention relates to a method of treatment of liver disease, said method comprising administering said method comprising administering a first composition and a second composition as defined above to said subject, each said first and second compositions comprising at least one epitope of a liver disease antigen, wherein said epitope is a CD8+ T cell epitope,
wherein administration of said first composition is by intramuscular (i.m.), subcutaneous (s.c.), intradermal (i.d.), oral or aerosol route, and administration of said second composition is by intravenous (i.v.), subcutaneous (s.c) or oral route, characterised in that said first and second compositions are administered by different routes.

In one aspect, the invention relates to a kit as described above for treatment of liver disease.

In one aspect, the invention relates to use of a kit as described above in the treatment of liver disease.

In some embodiments the invention may be used in treatment of a patient. By this is meant a patient actually having liver disease rather than prophylaxis by inducing a protective immune response before the patient is ill. For example one application of the invention may be in treating patients with liver disease caused by hepatitis B and/or hepatitis C. Another application may be treatment in a situation or condition/disease where CD8 T-cells are unable to enter affected site or are in a state "exhaustion" at this site. Treatment according to the invention would allow for functionally activated CD8 T-cells to be target to the correct site (e.g. tumour or chronic infection).

Suitably said container comprises a syringe. Suitably said container is a syringe.

FURTHER SUMMARY

In one aspect, the invention relates to a kit comprising at least a first composition and a second composition, each said first and second compositions comprising at least one epitope of a liver disease antigen, wherein said epitope is a CD8+ T cell epitope, for use in induction of an immune response in the liver of a mammalian subject by administration of said first composition by intramuscular (i.m.), subcutaneous (s.c.), intradermal (i.d.), oral or aerosol route, and administration of said second composition by intravenous (i.v.), subcutaneous (s.c.), intraperitoneal (i.p.) or oral route,
characterised in that said first and second compositions are administered by different routes.

In one aspect, the invention relates to a method of inducing an immune response in the liver of a mammalian subject, said method comprising administering a first composition and a second composition to said subject, each said first and second compositions comprising at least one epitope of a liver disease antigen, wherein said epitope is a CD8+ T cell epitope,
wherein administration of said first composition is by intramuscular (i.m.), subcutaneous (s.c.), intradermal (i.d.), oral or aerosol route, and administration of said second composition is by intravenous (i.v.), subcutaneous (s.c.), intraperitoneal (i.p.) or oral route,
characterised in that said first and second compositions are administered by different routes.

In one aspect, the invention relates to a kit, method, or use as described above wherein said liver disease antigen is from, or is derived from, an infectious pathogen that causes liver disease in humans, livestock or companion animals.

In other words we describe a kit method, or use as described above where the said epitope is a CD8+ T cell epitope from an liver-disease antigen derived from an infectious pathogen that causes liver disease in humans, livestock or companion animals.

The invention aims to use the novel immunisation approach to prevent or treat infectious diseases that affect the liver in humans, livestock and companion animals. These are all target populations or species to benefit currently from other types of immunisation. A liver disease antigen to be targeted by the invention need not cause disease in the liver, but must be expressed in the liver at some stage of infection and therefore potentially targetable by immunisation. This includes malaria infections as well as other infections, such as those caused by hepatitis and some other viruses. This is in contrast to Schneider 1998 which used only mouse parasite antigens which do not cause disease in humans.

In one aspect, the invention relates to a kit, method, or use as described above wherein said epitope is a CD8+ T cell epitope restricted by a human HLA class I molecule from a liver tumour antigen of humans or a liver cancer neoantigen epitope.

In other words we describe a kit method, or use as described above where the said epitope is a CD8+ T cell epitope restricted by a hum an HLA class I molecule from a liver tumour antigen of humans or a liver cancer neoantigen epitope.

It will be understood that an immunisation approach such as that described herein which can lead to effective CD8+ T cell immunity in the liver will be useful for preventing or treating diseases of the liver, not just caused by infectious pathogens but also by turn ours and cancers. Therefore the invention includes the use of the new immunisation approach to target antigens and epitopes expressed in the liver by turn ours, cancers and malignancies. The targeted epitope may be from any described cancer antigen, including viral antigens relevant to cancer caused by viruses in the liver, such as hepatitis B surface antigen and/or core antigen, and classical cancer antigen(s) such as the MAGE, 5T4, and NY-ESO antigens and many others, but also neoantigens which are now well described to be expressed in a wide range of tumours and malignancies and which may be particularly suited as target antigens of CD8+ T cells because of reduced tolerance to these compared to other cancer antigens. As with all protective CD8+ T cell epitopes in humans the relevant peptide will suitably be one presented by a human HLA class I molecule to a CD8+ T cell.

Thus the invention may be applied to tumour epitope(s) and/or infectious pathogen epitope(s).

In one aspect, the invention relates to a kit, method, or use as described above wherein said epitope is flanked on each side by at least seven amino acids of its native flanking sequence.

In other words we describe a kit method, or use as described above where the said epitope is a CD8+ T cell epitope flanked on each side by at least seven amino acids of its native flanking sequence.

We describe an improved approach for inducing effective CD8+ T cell responses in the liver that may protect against diseases such as malaria. This protection will often depend on CD8+ T cells. Suitably protection may involve recognition of minimal CD8+ T cell epitopes, of typically 8-10 amino acids in length, bound in the groove of MHC class I molecules (in humans HLA class I molecules). Thus suitably the CD8+ T cell epitopes is 8-10 amino acids in length. Thus suitably the CD8+ T cell epitope is bound in the groove of MHC class I molecule. Thus suitably the CD8+ T cell epitope is bound in the groove of HLA class I molecule. There is now considerable evidence that the flanking sequences of these minimal epitopes impacts on their processing intracellularly (e.g. Le Gall et al. Portable flanking sequences modulate CTL epitope processing *J Clin Invest*. 2007; 117:3563-75) so that altered flanking sequences may reduce or prevent presentation of such epitopes to T cells. This problem may be avoided by using natural flanking sequences found in the native antigen so as to allow correct processing. Native flanking sequences to each side of the epitope of seven amino acids or more are generally sufficient to allow adequate processing. Native sequences may be found by inspection of suitable publically available database (e.g. GenBank). Therefore, suitably epitope(s) are provided (or encoded) with the native flanking sequences of such length in the compositions of the invention.

This approach contrasts with Plebanski 1998 which discloses *P. falciparum* CD8 T cell epitopes but only as an epitope string with no individual epitope as long as 22 amino acids (8+7+7).

In one aspect, the invention relates to a kit, method, or use as described above wherein said first composition does not comprise plasmid DNA.

In other words we describe a kit method, or use as described above where the first composition is not a plasmid DNA composition such as a plasmid DNA vaccine.

A variety of compositions to deliver the epitope(s) may be used in the invention. These vary in ease of construction, manufacture and their ability to generate CD8+ T cell responses in humans. Plasmid DNA compositions such as vaccine compositions were discovered in the 1990s and initially thought to be useful as a simple means of inducing potent CD8+ T cell responses. However, a number of clinical trials of DNA compositions such as vaccine compositions have failed to induce such potent T cell responses. Therefore, suitably plasmid DNA compositions are not used in the invention such as in the first composition of the invention. Suitably vectors such as adenoviral vectors, especially simian adenoviral vectors are used in the compositions of the invention such as the first composition of the invention, which have the advantage of being more potent.

This is in contrast to Schneider 1998 which used plasmid DNA as the priming immunisation.

In one aspect, the invention relates to a kit, method, or use as described above wherein said second composition comprises a Modified Virus Ankara (MVA) poxvirus vector encoding said epitope and wherein said second composition comprises at least $2 \times 10^6$ plaque forming units of said vector.

In other words we describe a kit method, or use as described above where the dose of recombinant MVA used as the second composition is at least $2 \times 10^6$ plaque forming units.

Both MVA and adenoviral vectors are disclosed herein to be suitable second administration or "targeting" viral vectors. However, in bioluminescent imaging studies, stronger signals reflecting the levels of expression of the transgene in the liver were identified with the use of recombinant adenoviruses than recombinant MVA. This in part reflects the low dose level of MVA used, $1 \times 10^6$ pfu rather than the much higher dose of adenoviral vectors. Therefore, suitably, a higher dose of MVA should be used, $2 \times 10^6$ pfu or more, so as to enhance expression levels of the relevant antigen in the liver.

This contrasts with both Schneider 1998 and Plebanski 1998 who used $1 \times 10^6$ pfu of MVA and no more than that.

Schneider 1998 (Nature Medicine vol 4 pages 397-402) is confined to i.m. prime with plasmid DNA. There is no teaching nor motivation in Schneider et al 1998 to vary the priming composition. In contrast the present invention is focussed on viral vectors as the priming composition. In additions the invention teaches that adenoviral vectors are optimal. In addition the invention teaches that i.v. delivery (administration) of the 'targeting' or boosting composition is optimal. The inventors believe that no prior art has tried an i.v. targeting approach. The inventors provide data showing that results go from 0% to 100% protection using the approach taught herein. Moreover, in Schneider et al 1998 giving MVA intravenously did not improve. Giving MVA i.m. and i.v. was never done in the art. By contrast, the inventors show that optimal approaches such as using adenoviral vectors produce homing of circulating CD8+ T cells to the liver. The inventors also show that using this viral vector approach produces a higher level of circulating CD8+ T cells than prior art approaches using DNA which produce much lower levels of circulating T cells. The inventors believe that there has been no motivation in the art to use viral vectors such as MVA intravenously, and no evidence in the art of any benefit to giving viral vectors intravenously. In a real-life practical sense, this invention has been 15 years in the making and this new approach has not been used in the art in this very long time since the nearest known prior art approach. The inventors believe that no prior art has tried i.v. to target. FIG. 3 page 401 of Schneider et al 1998 is no motivation to give MVA iv boost because FIG. 3 and Table 4 of Schneider et al both show that intradermal is very similar to intravenous in terms of immunogenicity and efficacy and intradermal is hugely simpler to use and deploy. Therefore the reader would have been motivated to use intradermal not intravenous. Moreover, FIG. 2 page 400 of Schneider et al 1998 shows that DNA/MVA is best, so there would be no motivation to move to viral vectors for both the prime and boost because that is worse than DNA-MVA (1st bar of FIG. 2 vs 4th bar of FIG. 2 of Schneider et al 1998). In addition the inventors are aware of lots of human data showing that DNA-MVA is not good enough in humans, because efficacy is well under 15%. This is evidenced in the art, for example McConkey et al 2003 (Nature Medicine vol 9 page 729) discloses that with DNA-MVA the peak immune response following DNA-MVA is 162 SFC/million PBMCs and leads to only a slight delay in parasitaemia following malaria challenge; Ewer et al 2013 (Nature Communications DOI 10.1038/ncomms3836) discloses that ChAd63-MVA induces a peak immune response of 2646 SFC/million PBMCs, induces 21% sterile efficacy and significant delay in parasitaemia following malaria challenge. Thus, there is a need in the art for something better, which need is addressed by the present invention.

ADDITIONAL SUMMARY

In one aspect, the invention relates to a kit comprising at least a first composition and a second composition, each said first and second compositions comprising at least one epitope of a liver disease antigen, wherein said epitope
is a CD8+ T cell epitope, wherein said first and second compositions each comprise a viral vector encoding said epitope, said viral vector being selected from the group consisting of: adenoviral vector, adeno-associated viral vector or poxviral vector, for use in induction of an immune response in the liver of a mammalian subject by administration of said first composition by intramuscular (i.m.), subcutaneous (s.c.), intradermal (i.d.) or aerosol route, and administration of said second
composition by intravenous (i.v.) or subcutaneous (s.c.) route, characterised in that said first and second compositions are administered by different routes.
In one aspect, the invention relates to a method of inducing an immune response in the liver of a mammalian subject, said method comprising administering a first composition and a second composition to said subject, each said first and second compositions comprising at least one epitope of a liver disease antigen, wherein said epitope is a CD8+ T cell epitope, wherein said first and second compositions each comprise a viral vector encoding said epitope, said viral vector being selected from the group consisting of: adenoviral vector, adeno-associated viral vector or poxviral vector, wherein administration of said first composition is by intramuscular (i.m.), subcutaneous (s.c.), intradermal (i.d.) or aerosol route, and administration of said second composition is by intravenous (i.v.) or subcutaneous (s.c.) route, characterised in that said first and second compositions are administered by different routes.
In one aspect, the invention relates to use of a kit as described above in the treatment or prevention of liver disease.
Suitably said second composition is administered about 2 weeks after administration of said first composition.
Suitably said second composition is administered intravenously or subcutaneously, preferably intravenously.
Suitably said first composition is administered intramuscularly.
Suitably said first composition is administered intramuscularly and said second composition is administered intravenously.
Suitably said first composition comprises a particulate or particle-bound epitope, or a viral vector encoding said epitope, said viral vector being selected from the group consisting of: adenoviral vector or poxviral vector.
Suitably said second composition comprises a particulate or particle-bound epitope, or a viral vector encoding said epitope, said viral vector being selected from the group consisting of: adenoviral vector or poxviral vector.
Suitably said first composition comprises an adenoviral vector encoding said epitope, and said second composition comprises a poxvirus vector encoding said epitope.

Suitably said first composition comprises a simian or human adenoviral vector encoding said epitope, and said second composition comprises a Modified Virus Ankara (MVA) poxvirus vector encoding said epitope.
Suitably the viral vector of said first and second compositions is the same. This is a surprising benefit of the invention since it would not have been regarded as practical to use the same vector in both a prime and a subsequent boost/target administration before the present invention.
Suitably the immune response is a CD8+ cytotoxic T cell (CTL) response.
Suitably said at least one epitope of said first and second compositions is from the same liver disease antigen.
Suitably the least one epitope in said first and second compositions are the same.
Suitably said first and second compositions are different.
Suitably said first and second compositions are the same.
Suitably said liver disease antigen is from, or is derived from, an infectious pathogen that causes liver disease in humans, livestock or companion animals.
Suitably a 'companion animal' means one or more animals selected from the group consisting of: dogs, cats, horses, birds, rabbits, and fish.
Suitably a 'livestock animal' means one or more animals selected from the group consisting of: goats, sheep, cattle, pigs, camels, rabbits, fish, mules, asses, buffalo, chickens, turkeys, ducks, geese, and guinea fowl.
Suitably a mouse is not a companion animal. Suitably reference to 'companion animal' specifically excludes mice. Suitably a mouse is not a livestock animal. Suitably reference to 'livestock animal' specifically excludes mice.
Suitably said epitope is a CD8+ T cell epitope restricted by a human HLA class I molecule from a liver tumour antigen of humans or a liver cancer neoantigen epitope.
Suitably said epitope is flanked on each side by at least seven amino acids of its native flanking sequence.
Suitably said first composition does not comprise plasmid DNA.
Suitably said second composition comprises a Modified Virus Ankara (MVA) poxvirus vector encoding said epitope and wherein said second composition comprises at least $2 \times 10^6$ plaque forming units of said vector.
Suitably the antigen is selected from the group consisting of: a malarial antigen, a *P. falciparum* antigen, a *Plasmodium vivax* antigen, a *P. knowlesi* antigen, and a *P. berghei* antigen.
Suitably the antigen is selected from the group consisting of: a Hepatitis virus antigen, a Hepatitis A virus antigen, a Hepatitis B virus antigen, a Hepatitis C virus antigen, and a Hepatitis E virus antigen.
In one aspect, the invention relates to a device for administration of a composition as described above, said device comprising at least one dose of said composition(s).
In one aspect, the invention relates to a kit comprising a first container and a second container, each said container containing a composition comprising at least one epitope of a liver disease antigen,
wherein said first and second compositions each comprise a viral vector encoding said epitope, said viral vector being selected from the group consisting of: adenoviral vector, adeno-associated viral vector or poxviral vector, wherein said epitope is a CD8+ T cell epitope, for inducing an immune response in a subject, wherein said first container and said second container are used to administer said composition to said subject by different routes.

In one aspect, the invention relates to use of a kit as described above in induction of an immune response in a subject, wherein the compositions of said kit are administered to said subject.

In one aspect, the invention relates to a method of making a kit as described above, the method comprising selecting at least one epitope of a liver disease antigen, mixing said epitope(s) together with a pharmaceutically acceptable carrier, and formulating a first composition suitable for administration by intramuscular (i.m.), subcutaneous (s.c.), intradermal (i.d.) or aerosol route, preferably intramuscular (i.m.) route, and formulating a second composition suitable for administration by intravenous (i.v.) or subcutaneous (s.c.) route, preferably intravenous (i.v.) or subcutaneous (s.c.), route, most preferably intravenous (i.v.) route, wherein said first and second compositions each comprise a viral vector encoding said epitope, said viral vector being selected from the group consisting of: adenoviral vector, adeno-associated viral vector or poxviral vector, characterised in that said first and second compositions are formulated for administration by different routes.

In one aspect, the invention relates to a method of treatment of liver disease, said method comprising administering a first composition and a second composition as defined above to said subject, each said first and second compositions comprising at least one epitope of a liver disease antigen, wherein said epitope is a CD8+ T cell epitope, wherein administration of said first composition is by intramuscular (i.m.), subcutaneous (s.c.), intradermal (i.d.) or aerosol route, and administration of said second composition is by intravenous (i.v.) or subcutaneous (s.c.) route, characterised in that said first and second compositions are administered by different routes.

Suitably the kit as described above is for treatment of liver disease.

Suitably the use of a kit as described above is use in the treatment of liver disease.

DETAILED DESCRIPTION OF THE INVENTION

We disclose a new "prime-target" immunisation approach that leads to very high vaccine efficacy via heterologous administration routes, for example by changing the administration route of the second immunisation from intramuscular to intravenous.

A novel vaccine strategy aimed at priming CD8+ T-cells in the periphery e.g. at a highly immunogenic site (such as the muscle) and subsequently targeting them to hepatic tissue with protein loaded poly(lactic-co-glycolic acid) nanoparticles or recombinant viral vectors administered by specific routes was developed. Durable Ag-specific CD8+ T-cells were generated in the liver, with a ten-fold increase over the conventional heterologous viral vector regime which uses intramuscular administration for both priming and booster immunisations. Importantly, in a *P. berghei* sporozoite challenge model of liver stage malaria, this strategy was found to result in unprecedented sterile protection with a variety of clinically relevant antigens and mice strains, greatly improving current approaches. This prime and target immunization strategy for malaria immunisation may provide a general approach for prevention or immunotherapy of diseases caused by pathogens that infect the liver.

Regarding liver diseases such as Hepatitis B or Hepatitis C, prophylactic protection is typically achieved in the prior art using approaches to induce antibodies against viral proteins. However, in order to treat a subject T-cells are needed. In particular, T-cells are needed in the site of disease i.e. the liver. It is an advantage of the invention that a T-cell response is targeted to the liver.

Compositions or vaccines used to induce an antibody response to Hepatitis B or Hepatitis C antigens typically involve the viral protein being complexed with adjuvant and administered to a patient, typically by injection, in order to induce an antibody response. In contrast, the present invention is focused on the induction of cytotoxic T-lymphocytes (CTLs or $CD8^+$ T-cells) localised in a specific tissue such as the liver in order to actually recognise and clear intracellular pathogens. Antibody responses were also successfully generated with the present immunization regime; by harnessing both a cellular and humoral immune response the current invention greatly improves current immunisation regimens (e.g. vaccine regimens).

Suitably the antigen is a liver disease antigen. Suitably the antigen is a liver stage antigen. Suitably the liver disease is a disease caused by a pathogen of the liver. A pathogen of the liver includes a pathogen having a liver stage such as the malaria parasite. Therefore the antigen is suitably an antigen borne by the pathogen of the liver. Suitably the liver disease may include disorders such as liver cancer. Clearly, liver cancer does not necessarily have an underlying pathogen in the sense of an infectious agent or invasive organism underlying the disease. When discussing liver diseases such as liver cancer, the "pathogen" or disease causing agent refers to one or more of the cancer cells (tumour cells) themselves, but it could also or alternatively be a viral or pathogen antigen that contributed to the liver disease or cancer. Therefore in these embodiments the antigen is suitably an antigen borne by the cancer cells (tumour cells) in the liver. Suitably "liver cancer" means a solid cancer or tumour located in the liver. This may be a secondary tumour which has metastasised to and/or invaded the liver. Alternatively, "liver cancer" may refer to a solid cancer or tumour located in the liver which comprises primary liver cancer cells. Most suitably, liver cancer means primary cancer arising from liver cells.

In a broad aspect, the invention relates to any priming agent encoding a CD8 T cell epitope and an intravenous boost with an adenovector: thus in a broad aspect, the invention relates to a kit comprising at least a first composition and a second composition, each said first and second compositions comprising at least one epitope of a liver disease antigen, wherein said epitope is a CD8+ T cell epitope, wherein said second composition comprises an adenoviral vector, for use in induction of an immune response in the liver of a mammalian subject by administration of said first composition by intramuscular (i.m.), subcutaneous (s.c.), intradermal (i.d.) or aerosol route, and administration of said second composition by intravenous (i.v.) or subcutaneous (s.c.) route, preferably by intravenous (i.v.) route, characterised in that said first and second compositions are administered by different routes.

Malaria

A widely studied malarial parasite for mouse is *Plasmodium berghei*. The most important malarial parasite for humans is *Plasmodium falciparum*. The human pathogens (*P. falciparum, P. vivax, P. knowlesi*) do not infect mice. Therefore, mouse models of malarial disease conventionally employ the mouse parasite *P. berghei*. Alternatively, mouse models of malarial disease involve a transgenic *P. berghei*, for example a *P. berghei* expressing *P. falciparum* TRAP (PfTRAP) antigen or similarly, *P. berghei* expressing *P. vivax* TRAP (PvTRAP).

Antigens

The inventors have presented data (see examples below) using a range of antigens, including various antigens from the human malarial parasite *P. falciparum*. Ovalbumin has been used as an exemplary antigen. Similarly, *P. berghei* expressing ovalbumin has been used in a mouse model of disease in order to demonstrate advantageous effects of the invention.

Suitably the reference sequences of the antigens of interest are as defined in the following table:

Suitably where the antigen name is used, this means the corresponding amino acid or nucleic acid sequence from the above table. Suitably for amino acid sequences, the canonical sequence is preferred. Suitably for nucleic acid sequences, the most recent (e.g. highest numbered) nucleic acid sequence is preferred.

It will be understood that the invention may equally make use of fragment(s) such as epitopes or segments, variant(s) or mutant(s) of these antigens. Suitably any such fragment(s), variant(s) or mutant(s) have at least 80% sequence identity to the reference sequences along the whole length of said fragment(s), variant(s) or mutant(s), suitably 90%, suitably 95%, suitably 98% sequence identity along the whole length of said fragment(s), variant(s) or mutant(s).

Sequence identity may be calculated using any suitable technique known in the art. For example, a suitable computer program for carrying out such an alignment is the GCG

| Antigen | Protein Accession Number (e.g. UniProtKB) or amino acid sequence | Exemplary Epitope(s) | Gene name | coding sequence Accession Number (e.g. RefSeq Release 73) |
|---|---|---|---|---|
| *P. falciparum* TRAP antigen | Q76NM2 (UniProtKB) | | TRAP | PF3D7_1335900 (from PlamoDB Gene ID) |
| Hepatitis B antigen(s) | HBsAg_HBVA3 (UniProt) | 1. VLQAGFFLL<br>2. LLDYQGMLP<br>3. SIVSPFIPLL | HBsAg | X02763.1 (EMBL) |
| Hepatitis C antigen(s) | M58335 | 1. KLSGLGINAV<br>2. ATDALMTGY | NS3-nnut (NS3-5B region of genotype 1B) | KM044036.1 |
| Liver Cancer antigen(s) | P02771 | GVALQTMKQ | a-fetoprotein (AFP) | AK314817 (EmBL) |
| *P. falciparum* Liver stage antigen 1 (LSA1) | Can be found at: PF3D7_1036400 (from PlamoDB Gene ID) | 1. EKEKFIKSLFHIFDG<br>2. DKSLYDEHIKKYKND<br>3. KKEHGDVLAEDLYGR | Liver stage antigen 1 | PF3D7_1036400 (from PlamoDB Gene ID) |
| *P. falciparum* Liver stage associated protein 2 (LSAP2) | Can be found at: PF3D7_0202100 (from PlamoDB Gene ID) | 1. HKLPFKIKMKKWWK<br>2. KDFYMLFLSNKKEKI<br>3. KFNKMKSSL<br>4. SKFMKLSISLLLLAL | Liver stage associated protein 2 (LSAP2) | PF3D7_0202100 (from PlamoDB Gene ID) |

The sequences are hereby incorporated herein by reference.

The skilled worker only has to identify the correct gene/protein being used as antigen. The guidance provided is not intended to restrict the invention rigidly to the specific single exemplary sequences provided. Gene sequences (and therefore protein sequences) are known to vary between individuals and/or between strains or isolates of the pathogen(s) e.g. due to allelic variance or mutations between individuals. The information provided is to assist the operator in working the invention by using a suitable protein/gene. Ultimately the gene product (suitably protein) is actually used or encoded. Therefore minor or minimal allelic or mutational differences between individuals are not important, what is important is that the correct antigen/epitope is used or encoded in the compositions of the invention.

Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Suitably default settings are used for any gap penalties or other such values required for the calculation.

Suitably the epitope is a protein epitope.

Suitably the antigen is a protein antigen.

Suitably the antigen is selected from the group consisting of: a malarial antigen, a Hepatitis B virus antigen and a Hepatitis C virus antigen or a cytomegalovirus antigen or a hepatitis E virus antigen or a hepatitis A virus antigen or an Epstein-Barr virus antigen.

More suitably the antigen is selected from the group consisting of: a malarial antigen, a Hepatitis B virus antigen and a Hepatitis C virus antigen.

Suitably the antigen/epitope is not HGXPRT. Suitably HGXPRT is excluded.

Suitably the antigen/epitope is not IL-12. Suitably IL-12 is excluded.

Database Release

Sequences deposited in databases can change over time. Suitably the current version of sequence database(s) are relied upon. Alternatively, the release in force at the date of filing is relied upon.

As the skilled person knows, the accession numbers may be version/dated accession numbers. The citeable accession numbers for the current database entry are the same as above, but omitting the decimal point and any subsequent digits.

GenBank is the NIH genetic sequence database, an annotated collection of all publicly available DNA sequences (National Center for Biotechnology Information, U.S. National Library of Medicine 8600 Rockville Pike, Bethesda Md., 20894 USA; Nucleic Acids Research, 2013 January; 41(D1):D36-42) and accession numbers provided relate to this unless otherwise apparent. Suitably the GenBank database release referred to is 15 Dec. 2015, NCBI-GenBank Release 211.0.

UniProt (Universal Protein Resource) is a comprehensive catalogue of information on proteins ('UniProt: a hub for protein information' Nucleic Acids Res. 43: D204-D212 (2015).). For the avoidance of doubt, UniProt Release 2015_11 is relied upon.

In more detail, the UniProt consortium European Bioinformatics Institute (EBI), SIB Swiss Institute of Bioinformatics and Protein Information Resource (PIR)'s UniProt Knowledgebase (UniProtKB) Release 2015_12, (9 Dec. 2015) is relied upon. PlasmoDB (http://PlasmoDB.org) is the official database of the *Plasmodium falciparum* genome sequencing consortium. This resource incorporates the recently completed *P. falciparum* genome sequence and annotation, as well as draft sequence and annotation emerging from other *Plasmodium* sequencing projects. See Nucleic Acids Res. 2003 Jan. 1; 31(1): 212-215; and PlasmoDB: a functional genomic database for malaria parasites. Nucleic Acids Res. 2008 Oct. 31. Aurrecoechea C, et al. PlasmoDB is sometimes referred to as "PlamoDB" herein. Suitably PlasmoDB release 28 of 31 Mar. 2016 is relied upon.

Hepatitis

There are five known human Hepatitis viruses: Hepatitis A, B, C, D, and E. Hepatitis A and Hepatitis E are less serious diseases with low mortality rates. However, either of these Hepatitis viruses can be more serious in vulnerable patients, such as immunocompromised patients or pregnant women. Thus, suitably the antigen may be a Hepatitis A antigen or a Hepatitis E antigen.

Hepatitis D typically only infects patients as a co-virus (co-infection) together with Hepatitis B. Thus, in one embodiment, the antigen may be a Hepatitis D antigen.

Hepatitis B and Hepatitis C are serious diseases in humans. These are especially dangerous if they develop into chronic infections, when sclerosis of the liver and/or liver cancer may develop. Thus, most suitably the antigen of the invention is a Hepatitis B antigen or a Hepatitis C antigen. In one embodiment, compositions are provided which comprise both an epitope from a Hepatitis B antigen and an epitope from a Hepatitis C antigen. This has the advantage of providing a single composition (or single set of compositions) for use in immunising against both Hepatitis B and Hepatitis C viruses in a single set of administrations.

Hepatitis B is a widespread problem in human health. For example, it is estimated that as many as 10% of the East Asian population have Hepatitis B. Hepatitis B is a human virus with the genome of approximately 3.5 Kb. Sequence of an exemplary Hepatitis B viral genome is as in accession number AB775201.1 (GenBank, DNA circular genome).

Hepatitis C is another cause of liver disease in humans. Hepatitis C is also a widespread virus, with a genome of approximately 9.6-12.3 Kb. Sequence of an exemplary Hepatitis C viral genome is as in accession number D11168.1 (GenBank, RNA linear genome).

Liver Antigens

Identification of liver stage antigens in pathogens of the liver is a well understood process in the prior art. For example, liver stage antigens can be determined via bioinformatics predictions, or RNA analysis of parasitized liver cells, or detailed literature searches together with in vitro testing for possible antigen presentation. Alternatively, MHC class I-peptide complexes from infected cells (for example, hepatocytes infected with spz) can be purified and, using mass-spectronomy analysis, relevant antigens with immunodominant epitopes can be determined. Leading candidates can be cloned into viral vectors and immunogenicity, as well as ability to sterile protect challenged mice, determined.

Suitably the epitope is a CD8 T-cell epitope. CD8 T-cell epitopes may differ in amino acid sequence between individual human beings in the population due to ordinary genetic variation. Suitably the epitope is an HLA-A2 epitope. This has the advantage that HLA-A2 is the most common human MHC type. Therefore, an epitope recognised in the context of HLA-A2 may cover as much as 50% of a typical human population.

Administration Regimes

It is a key feature of the present invention that the first and the second or subsequent immunisations are by different routes. Suitably the first and the second or further immunisations are by different routes. Suitably the first and the second or further immunisations are by heterologous routes.

Suitably the first administration comprises an adenoviral vector.

Suitably the second administration comprises an adenoviral vector or a poxviral vector such MVA, most suitably a poxviral vector.

Suitably the first administration is intramuscular.

Suitably the second or further administration is subcutaneous.

Most suitably the second or further administration is intravenous.

It should be noted that nowhere in the prior art are different routes of administration for compositions of the same antigen or epitope taught. There may be one possible exception, in addressing mucosal surfaces, when occasionally aerosol or intranasal applications may be used for boosts following a conventional prime such as an intramuscular prime. In any case, the invention does not embrace any regime where the second or further administration is by aerosol or intranasal application. Suitably the second or further administration is not aerosol. Suitably the second or further administration is not intranasal.

It is a key feature of the invention that heterologous routes of administration are used for the first and the second or further administrations.

In one embodiment more than one dose of the first administration may be given (an additional first administration) provided that it is followed by a second or further administration by a heterologous route which is either IV or SC. This is discussed herein (see "prime-boost-target").

Doses

Unless otherwise apparent, doses are for adult humans; doses may be varied by the skilled operator as necessary using the guidance herein. Dosing is suitably determined by a physician.

Suitably approximately 1 microgram to 100 micrograms of antigen is administered for protein or peptide based antigen, but as much as 5 mg may be given if required.

Suitably when viral vectors are used, approximately a viral vector dose per administration of $10^6$ to $10^{12}$ viral particles of an adenoviral vector is given, more typically $10^8$ to 1011 viral particles of the adenoviral vector. When an MVA vector is used $10^6$ to 109 plaque forming units (pfu) per administration of the MVA vector is used, more typically 107 to $10^8$ pfu viral particles are used per administration.

The dosage may vary according to the route of administration. In this regard, approximate doses per administration are shown in the following table.

| Route of administration to adult human | Micrograms epitope per Kilogram bodyweight | Viral Vector Particles per Kilogram body weight |
|---|---|---|
| Intramuscular (I.M.) | 50 micrograms | $5 \times 10^{10}$ vp/volunteer (approx. $7 \times 10^8$/kg) |
| Subcutaneous (S.C.) | 50 micrograms | $5 \times 10^{10}$ vp/volunteer (approx. $7 \times 10^8$/kg) |
| Intradermal (I.D.) | 50 micrograms | $5 \times 10^{10}$ vp/volunteer (approx. $7 \times 10^8$/kg) |
| Oral | 50 micrograms | $5 \times 10^{12}$ vp/volunteer (approx. $7 \times 10^{10}$/kg) |
| Intravenous (I.V.) | 50 micrograms | $5 \times 10^8$ vp/volunteer (approx. $7 \times 10^6$/kg) to $5 \times 10^{10}$ vp/volunteer (approx. $7 \times 10^8$/kg) |

Timing

Suitably the first and the second or further administrations are not given simultaneously.

Suitably the first and the second or further administrations are given separately. Suitably the first and the second or further administrations are given sequentially.

Suitably the second or further administration is given at a time to coincide with the peak of the previous immune response.

The second or further administration may be given in a period from one day to several years after the first or previous administration, suitably about 2 weeks after the first or previous administration.

Suitable times for the second or further administration are: 1 day, 1 week, 10 days, 2 weeks, 3 weeks, or three years after the first or previous administration, with 2 weeks being most suitable.

Suitably any further administration is given about 2 days to 12 weeks after the previous (e.g. most recent preceding) administration, most suitably 2 weeks after the previous (e.g. most recent preceding) administration.

More suitably the second or further administration is given about 2 weeks after the first or previous administration, most suitably 2 weeks after the first or previous administration.

More suitably the second administration is given about 2 weeks after the first administration, most suitably 2 weeks after the first administration.

Vectors

It has been observed that adenovirus administered to a subject can have a tropism for the liver. However, the present inventors disclosed for the first time that high level cell mediated immunity (CMI) responses can be generated and localise in the liver. This effect is advantageously achieved by the compositions and administration regimes disclosed herein.

Suitably the adenoviral vector is a human or simian adenovirus based vector, most suitably a human adenovirus based vector. Suitably the adenoviral vector is Ad5, ChAdOx1, ChAd3 or ChAd63; more suitably the adenoviral vector is Ad5 or ChAdOx1; most suitably the adenoviral vector is Ad5. These and other vectors are well known in the art and have been widely published, including with relevant sequence deposits. In case any further guidance is needed, for example Ad5 vector may be used with reference to GenBank accession number AC_000008.

In one embodiment, the adenoviral vector is not ChAd63. Such vectors are described in the art, for example:

ChAd63 GenBank: CS479279.1 (e.g. see WO2006-133911) or GenBank: JB344651.1 (e.g. see EP257-0423)

ChAd3 GenBank: JB344647.1 (e.g. see EP2570423)

ChAdOx1 is described in Dicks M D J, Spencer A J, Edwards N J, Wadell G, Bojang K, et al. (2012) A Novel Chimpanzee Adenovirus Vector with Low Human Seroprevalence: Improved Systems for Vector Derivation and Comparative Immunogenicity. PLoS ONE 7(7): e40385, and in WO2012/172277. In addition, a clone of ChAdOx1 containing GFP is deposited with the ECACC: a sample of *E. coli* strain SW10029 (a derivative of DH10B) containing bacterial artificial chromosomes (BACs) containing the cloned genome of AdChOX1 (pBACe3.6 AdChOx1 (E4 modified) TIPeGFP, cell line name "AdChOx1 (E4 modified) TIPeGFP") was deposited by Isis Innovation Limited on 24 May 2012 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 12052403. Isis Innovation Limited is the former name of the proprietor/applicant of this patent/application.

Adenoviral vectors are known in the art. In particular, adenoviral vectors have been used in anti-tumour approaches. However, anti-tumour approaches have specifically sought to avoid any immune response in the liver. For example, one prior art approach involving adenoviral vectors is known as oncolytic viral therapy. This approach involves trying to get virus into a tumour in order to lyse the cells of that tumour. These approaches have tended to use Vaccinia virus, Herpes virus, and sometimes adenovirus based approaches. Whilst an immune response can be generated against viruses administered in this manner, that response is directed at the virus itself. In contrast, the present invention relates to using viral vectors to deliver an antigen against which the response is raised. In the prior art approach, it is extremely undesirable to have immune responses directed against the viruses, since those immune responses might well eliminate those viruses before they have carried out their therapeutic effects such as helping to lyse tumour cells. Therefore, the use of viral vectors in the present invention is different in approach to the use of viral vectors in prior art applications such as oncolytic viral therapy.

Suitably the poxviral vector is an avipox vector, an orthopox vector, a NYVAC vector, or an MVA vector. Most suitably the poxviral vector is Modified Vaccinia Ankara (MVA). These and other vectors are well known in the art and have been widely published, including with relevant sequence deposits. In case any further guidance is needed, we refer to GenBank accession number: AY603355.1.

For example, an especially preferred MVA vector for use in the invention is as described in this accession number, Acambis 3000 strain with the exception of a 6 bp insertion in the non-essential gene F7L (Cottingham et al., (2008, PLosOne)).

Prior art approaches to gene therapy have even involved direct administration of the viruses to the hepatic artery, often in enormous doses (such as 1000× the doses taught in the present invention). In these approaches, the viruses are typically used to deliver genes such as genes considered to be "missing" from the cells which are being targeted, for example to deliver ornithine transcarboxylase. Once again, it is an aim of such gene therapy approaches to avoid possible immune response generated by the use of these viral vectors. Indeed, there are examples of clinical trials where subjects have unfortunately suffered fatal side effects which may have been due to immune responses caused by the gene therapy vectors administered.

As should be apparent from the above, the approach taken by the present inventors is wholly incompatible with prior art uses of adenovirus based vectors in oncolytic viral therapy/gene therapy applications. In prior art approaches, immune responses are actively unwanted and therefore these prior art approaches would never involve the administration of a first dose to "prime" the immune response as is taught by the current invention.

It is known in the prior art to purify sporozoites and then administer them intravenously (I.V.). For example, Sanaria's approach has been to purify sporozoites and then administer them I.V. to a subject. This approach has involved administration of the same composition (the sporozoites) many times, for example five times to the same subject. Moreover, very large doses of the purified sporozoites are administered, which is in contrast to the advantageously low levels of antigen administered by the present invention. Most importantly, there is no teaching or hint of any heterologous administration route in Sanaria's approach. Therefore, there are crucial differences between Sanaria's approach and the present invention, which include the use of viral vectors, and also include the use of a heterologous administration route for the first and the second or further administration.

Suitably the viral vector is selected from the group consisting of: adenoviral vector, adeno-associated viral vector and poxviral vector. More suitably the viral vector is selected from the group consisting of: adenoviral vector and poxviral vector. Most suitably the viral vector is an adenoviral vector.

Comparative Data

It should be noted that the heterologous administration route is of vital importance to the present invention. Although the I.V. route is preferred for the second or further administration, the invention does not embrace a multiple application of administrations only via the I.V. route. Indeed, the use of booster I.V. administration is not known to be a useful route to induce an immune response. Many researchers would consistently strive to avoid this route. The I.V. route is known not to be the best for inducing an immune response. Indeed, the inventors present their own data showing that giving a first and a second I.V. administration using the viral vectors detailed herein does not lead to the beneficial effect of the invention. The beneficial effect of the invention is achieved using heterologous routes of administration. In stark contrast, using a heterologous administration regime according to the invention, for example a first administration intramuscularly (I.M.) and then a second or further administration intravenously (I.V.) produces surprisingly excellent results as demonstrated in the examples and data which form part of this patent application.

Furthermore, the use of the SC route for a booster immunisation following an intramuscular priming immunisation is not known to be useful in the field. Although subcutaneous (S.C.) is a well recognised immunisation route the use of this as a particularly good route for targeting the liver with cellular immunity is novel.

Suitably the first administration according to the invention is not given via an I.V. route. Suitably the first administration is given by a route other than I.V. Suitably the first administration is given by a parenteral route other than I.V. Suitably I.V. administration is not used for the first administration.

A pair of administrations comprising a first I.V. administration and a second I.V. administration does not form part of the invention, since that does not present heterologous routes of administration (since in this scenario both administrations would be I.V.). It is a key part of the invention that the administration routes are heterologous (i.e. different).

It is a key advantage which is delivered by the invention that using a second or further administration which is via the I.V. or S.C. route, most suitably the I.V. route, produces a liver response.

It is a key advantage which is delivered by the invention that using a second or further administration by a different route to the first administration, suitably which second or further administration is via the I.V. or S.C. route, most suitably the I.V. route, produces high level protection (sterile efficacy).

Suitably the viral vector is an adeno based viral vector or a pox based viral vector.

Suitably the adeno based vector is selected from the group consisting of hAd5, ChAd63, ChAd3 and ChAdOx1, more suitably from the group consisting of hAd5 and ChAdOx1, most suitably the adeno virus based vector comprises ChAdOx1. Suitably the pox virus based vector comprises modified virus Ankara (MVA).

It may be possible to use adeno associated virus (AAV) derived vectors in the present invention. One possible advantage which might be achieved by the use of AAV based vectors is that they can be administered orally and may be targeted to the liver.

In order to choose correct AAV serotype(s), these should be chosen as those having the highest affinity for hepatocytes. Testing their affinity for hepatocytes is so routine and standard that any person skilled in the art would be able to do it with no further help or instructions. In the event that further guidance is required, we refer to the book chapter "AAV-mediated liver-directed gene therapy" (Methods Mol Biol. 2011; 807:141-57) which describes AAV8 and AAV9 with higher affinity for hepatocytes so would be best for liver-gene induction. Thus suitably the AAV vector is an AAV8 or AAV9 vector. These vectors are known in the art for example AAV8 is GenBank: HV550988.1 (e.g. see EP2345731). The view in the art is that AAV is not very immunogenic and is used in the field of gene transfer where it is considered an advantage that it is not very immunogenic; see for example a review of immune response to Adenovirus and Aden-associated viruses, which states how responses to Adeno virus are strong AAV characteristically induce weak (if anything) responses to the transgene (Gene Ther. 2003 June; 10(11):955-63). Therefore it is surprising that the inventors teach that AAV vectors are useful in the invention.

Diseases

Suitably the invention is used to target any disease in a subject which is a liver disease. Suitably, the disease or disorder has a liver stage. Suitably the disease or disorder is selected from the group consisting of Malaria, Hepatitis B and Hepatitis C.

Suitably the disease is chronic HBV infection.

Suitably the subject is a mammal, most suitably a primate, most suitably a human.

Suitably the first administration is by the I.M., S.C., I.D., oral or aerosol route; more suitably via the I.M., SC, ID or aerosol route; more suitably via the I.M., S.C. or I.D. route, most suitably via the I.M. route.

Suitably the second or further administration is via the I.V., S.C. or oral route, more suitably via the I.V. or S.C. route; most suitably via the I.V. route.

Suitably the first and second administrations are via different routes. In more detail, suitably the first administration is via a first route and the second administration is via a second route, wherein the first route and the second route are different.

Suitably the antigen(s) and/or epitope(s) administered in the first and second administrations are the same.

Suitably the vector or vectors used for the first administration and the second administration may be the same or may be different; suitably the vectors are different. Thus, suitably a first administration comprises a first vector and a second administration comprises a second vector wherein the first vector and the second vector are different.

When administration is oral, the vector is suitably not adenovirus based nor pox virus based. By way of explanation, adenovirus and pox virus are not known to be optimally effective for oral administration. Suitably when administration is oral, the vector is suitably an adeno-associated virus (AAV) based vector.

When the vector is in the form of a particulate vector such as PLGA or other nanoparticle, the protein or viral vector may be coated onto said particulates or may be embedded within said particulates, or both. Alternatively, the viral vector may be encapsulated so as to facilitate delivery to the liver, such as PLGA-adenovirus constructs.

Suitably the vector is not a VSVG based vector.

The first vector and the second vector may be the same. Suitably the first vector and the second vector are different.

In one particularly preferred embodiment, a first administration (priming) is provided using adenoviral vector intramuscularly; an additional first administration (boosting) is provided using a pox virus based vector such as MVA intramuscularly; a second or further heterologous administration (targeting) is provided using an adenovirus based vector administered intravenously. This three-pronged approach may be termed "prime-boost-target". Suitably the gap between the first and additional first administrations is several weeks; suitably the gap between the additional first and the second or further administrations is about one day to three months, suitably about two weeks, most suitably two weeks.

Immune Response in the Liver

Suitably the immune response is a cell mediated immune response (CMI).

Suitably the immune response is a T-cell mediated response, suitably a CD8+ T-cell mediated response.

Suitably the immune response is in the liver, suitably generated in or targeted to the liver, most suitably targeted to the liver.

Suitably the immune response is protective.

The phrase "protective immune response" as used herein means that the composition is capable of generating a protective response in a host organism, such as a human or a non-human mammal, to whom it is administered according to the invention. Suitably a protective immune response protects against subsequent infection or disease caused by the liver pathogen such as *Plasmodium falciparum* or Hepatitis virus or other liver pathogen(s) mentioned herein. The protective immune response may eliminate or reduce the level of infection by reducing replication of (e.g.) *Plasmodium falciparum* or Hepatitis virus, or by affecting the mode of action of (e.g.) *Plasmodium falciparum* or Hepatitis virus to reduce disease.

It is important to the invention that the immune response is in the liver. This is typically tested by taking a sample of the liver, separating the cells in that sample, isolating the lymphocytes, and determining the number of lymphocytes specific for the antigen/epitope which was administered. Numbers of lymphocytes specific for the antigen/epitope in the range $10^6$ total antigen/epitope specific T cells is considered to show that the response has been generated (in the context of mouse liver immunology), more suitably in the range 15-20% for all hepatic CD8 T-cells (in the context of mouse liver immunology). Alternative methods of detection can be via histological quantification.

When considering a human subject, suitably a liver biopsy may be taken for this purpose.

Suitably the lymphocyte is a T-cell.

Suitably the T-cell is a $CD8^+$ T-cell.

Suitably the T-cell is a $T_{RM}$.

Without wishing to be bound by theory, the inventors' insights included the observation that tissue resident T-cells ($T_{RM}$) appeared to be mediating these surprising and advantageous effects. $T_{RM}$ are a recognised class of T-cells which are tissue resident i.e. they are localised and remain within certain loci such as organs e.g. the liver.

The markers expressed by $T_{RM}$ are agreed worldwide. $T_{RM}$ comprise a non-recirculating population of cells resident in a multiple peripheral tissues such as the skin, lung, mucosal surfaces, kidneys and liver [49, 50]. A $T_{RM}$ in the context of liver residency is regarded as an antigen-specific T-cell expressing the following markers: CXCR6, CD69, $CD127^{lo}$, $CD62L^-$, $IFNg^+$. These are typically assessed by immunological staining of the cell surface with appropriate antibodies to specifically detect the presence or absence of the markers. Additional markers that can also be considered in the context of liver residency are the downregulation of the following two transcription markers: $Eomes^{lo}$ KLF210.

The "gold standard" test for achieving protection from Malaria is by having human subjects be bitten by mosquitoes and testing the efficacy of the immunisations under challenge from the malarial pathogen. This type of study is carried out in this field with informed consent and treatment of any individuals becoming infected during the testing.

The data presented in this patent application include a large amount of data obtained from the mouse model. It is important to note that there is a large amount of diversity amongst the data presented. For example, several different antigens have been tested in mice using the approach of the invention, including both antigens such as ovalbumin as well as antigens from the disease causing pathogens of interest. In addition, antigens from different diseases (including Malaria and Hepatitis such Hepatitis B) have been tested, providing a further level of diversity to the data in this document. Therefore it is submitted that a person skilled in the art understands from these detailed and robust data that the invention can be worked in humans.

Suitably a course of administrations is given to a subject. Suitably the course comprises a first administration and a second administration. The first administration is sometimes referred to as "prime". The second administration is sometimes referred to as "target". Of course, it may be possible that the subject receiving the administrations has previously encountered one or more of the antigens being administered to them as described herein. For the purposes of this disclosure, it does not matter if the subject has any or no pre-existing immunity or reaction against the antigens administered to them with the first ("prime") administration. The subject may be naïve with respect to the antigens in the composition, or may have a pre-existing exposure and/or response to those antigens. What is important is that the first and second administrations in the course administered to a subject as described herein are given by different routes of administration. This difference is very important to the targeting benefits delivered by the invention.

Compositions

Suitably the composition is a pharmaceutical composition.

Suitably the composition is an antigenic composition.

Suitably the composition is an immunogenic composition.

Suitably the composition is a vaccine composition.

Suitably the composition is formulated for administration to mammals, suitably to primates, suitably to humans.

Suitably the composition is formulated taking into account its route of administration.

Suitably the composition is formulated to be suitable for the route of administration specified. Suitably the composition is formulated to be suitable for the route of administration selected by the operator or physician.

Adjuvants

According to another aspect of the invention, there is provided a composition such as a pharmaceutical composition comprising the immunogenic composition or vaccine according to the invention herein and a pharmaceutically acceptable carrier.

The pharmaceutically acceptable carrier may comprise saline, water, or buffer. The pharmaceutically acceptable carrier may comprise one or more compatible solid or liquid diluents or encapsulating substances which are suitable for administration to the body of a mammal, such as a human. The pharmaceutically acceptable carrier may be a liquid, solution, suspension, gel, ointment, lotion, powder, or combinations thereof. The pharmaceutically acceptable carrier may be a pharmaceutically acceptable aqueous carrier.

The composition (such as pharmaceutical composition, immunogenic composition or vaccine) may further comprise an adjuvant. The adjuvant may comprise an oil emulsion. The adjuvant may be selected from any of the group comprising PEI; Alum; AS01 or AS02 (GlaxoSmithKline); inorganic compounds, such as aluminum hydroxide, aluminum phosphate, calcium phosphate hydroxide, or beryllium; mineral oil, such as paraffin oil; emulsions, such as MF59; bacterial products, such as killed bacteria *Bordetella pertussis*, or *Mycobacterium bovis*; toxoids; non-bacterial organics, such as squalene or thimerosal; the saponin adjuvant matrix M (Isconova/Novavax) or other ISCOM adjuvants; detergents, such as Quil A; cytokines, such as IL-1, IL-2, or IL-12; Freund's complete adjuvant; and Freund's incomplete adjuvant; toll-like receptor agonists such as CpG or mono-phosphoryl lipid A, or other adjuvants reported to enhance induced immune responses, or combinations thereof. The composition may also comprise stabilising agent(s) including thermostabilising agent(s) known in the field, such as the sugar trehalose.

Further Applications

In a broad aspect, the invention relates to the generation of tissue localized protective immunity using a multi-route vaccination strategy.

Also broadly disclosed is a novel method for inducing high levels of circulating T-cells and subsequently targeting them to a relevant tissue such as the liver. The strategy proposed is comprised of an initial prime (first) vaccination at a site known to induce high levels of circulating Ag-specific CD8+ T-cells, which may be, but is not limited to intramuscular, subcutaneous or intradermal immunisation. The initial dose is followed by a second or further administration to target the chosen site by providing vaccine antigen at that site where the resident population is desired. This will likely include, but is not limited to, a site where initial priming is sub-optimal or cellular T-cell location is crucial. Examples of this include, but are not limited to, mucosal surfaces of the lung, gut, reproductive tract and skin, as well as solid tumors, internal organs, such as the spleen and the liver, and lymphatic system. This approach could be used both for prophylactic and therapeutic vaccination for a variety of infectious and non-infectious diseases such as, but not limited to those caused by *Plasmodium* species, Hepatitis B and C, CMV, EBV, Influenza, herpes simplex virus, human papilloma virus, *chlamydia*, gonococcus, *Mycobacterium tuberculosis*, and malignant cancers and tumours such as prostate, lung, colorectal, renal and skin cancers. This strategy will hereby be referred to as "prime-target" immunisation.

Also broadly disclosed is a novel approach using a an initial priming immunization at a non-mucosal site to successfully expand circulating T-cell responses and then subsequently targeting these T cells to the tissue of interest by means of a further intravenous or mucosal immunization. Prior attempts to target the female genital tract have been performed using mucosal specific chemokines to localize Ag-specific T-cells or attenuated pathogens in so-called 'prime-pull' immunisation. But in that approach cytokines and/or chemokines were applied locally to the mucosa to attract T cells. In contrast we use a booster dose of vaccine to target the T cells to a tissue of interest such as the liver or a mucosal surface.

Thus we describe a novel heterologous route vaccine strategy aimed at generating high numbers of circulating Ag-specific T-cells and subsequently targeting these T cells to a tissue of interest. This prime-target approach has been shown to be highly effective in the context of liver-stage malaria, similar results could also be obtained for other infectious and non-infectious pathologies in a wide array of tissues where T-cell priming is sub-optimal and/or a high frequency of T-cells at a specific location is needed. This novel regimen is relevant both in the context of prophylaxis and treatment.

In a broad aspect, the invention relates to a method of immunization against liver-stage malaria infection or liver-stage microbial pathogens or liver cancer comprising of an intramuscular vaccination followed by an intravenous or subcutaneous vaccination, suitably intravenous vaccination.

Also disclosed is a pharmaceutical product comprising a dispensing device adapted to deliver a composition as defined herein. Also disclosed is a combination of such a device with a composition as defined herein. Suitably a kit comprising two such devices, suitably in combination with two such compositions, is disclosed.

A method of eliciting a protective immune response in a subject, wherein two compositions as described herein are administered to said subject by two different routes.

A method of inducing an immune response in a subject, wherein two compositions as described herein are administered to said subject by two different routes.

A method of inducing $T_{RM}$ in a subject, wherein two compositions as described herein are administered to said subject by two different routes.

A method of inducing an immune response in the liver of a mammalian subject, said method comprising administering a first composition and an additional first composition and a second composition to said subject, each said first and additional first and second compositions comprising at least one epitope of a liver disease antigen,
wherein said epitope is a CD8+ T cell epitope,
wherein administration of said first and additional first compositions is by intramuscular (i.m.), subcutaneous (s.c.), intradermal (i.d.), oral or aerosol route, and administration of said second composition is by intravenous (i.v.), subcutaneous (s.c.) or oral route,
characterised in that said first and second compositions are administered by different routes.

The invention also relates to a kit comprising a first composition and an additional first composition and a second composition as defined above.

Suitably the time between administration of said first composition and said additional first composition is 1 to 12 weeks, suitably three weeks.

Suitably the time between administration of said additional first composition and said second composition is the time of the peak of the first composition response, suitably two weeks.

Suitably said first composition comprises an adenoviral vector encoding said epitope.

Suitably said additional first composition comprises a MVA vector encoding said epitope.

Suitably said second composition comprises an adenoviral vector encoding said epitope.

Suitably said first composition is administered by intramuscular route (i.m.).

Suitably said additional first composition is administered by intramuscular route (i.m.).

Suitably said second composition is administered by intravenous route (i.v.) or subcutaneous (s.c) route, suitably by intravenous route (i.v.).

The invention finds application in induction of short term protection (efficacy), for example for travelers or military personnel.

The invention finds application in providing more durable protection, for example for immunisation of residents of malaria-endemic regions Also disclosed is that the priming vaccine can be any vaccine capable of inducing a circulating T cell response and may be administered by an intramuscular or intradermal or subcutaneous or oral route but not by an intravenous route. The secondary vaccination is administered intravenously or subcutaneously, suitably intravenously, for targeting the liver, but can also be given orally or in any fashion resulting in hepatic liver accumulation of Ag. Secondary vaccination can use a viral vector expressing the same antigen (e.g. a recombinant Adenovirus or recombinant MVA) or a particulate carrier (for ex: PLGA-protein NPs). The vaccination regimen can be given simultaneously or separated in time (for example: at a two-week interval). Particulate formulation is not limited to PLGA-OVA, but can also include different polymers, formulations, adjuvants, and protein encapsulation methods. Priming site of immunization is at a highly immunogenic site such as, but not limited to, intra muscular, sub-cut or id. The priming vaccine and secondary vaccination are administered by different routes.

A method of immunization against infectious liver diseases such as, but not limited to: malaria, hepatitis B and C, CMV (cytomegalovirus), and EBV (Epstein-Barr virus); A viral vector construct expressing a relevant immunogenic antigen or a particulate is administered in a similar fashion as described above; A method of immunization against respiratory tract infectious diseases such as influenza, RSV (respiratory syncytial virus) rhinovirus, *M. tuberculosis, pneumococcus, staphylococcus*. A viral vector construct expressing an immunogenic antigen is administered at a highly immunogenic site (such as intramuscularly). Secondary targeting of Ag-specific T-cells is performed via viral vector or particulate administration via intranasal or aerosol administration. Similar applications of prime-target immunisation can be envisioned to be relevant in the context of skin, gastro-intestinal and genito-urinary tract diseases, as well as lymphatic organs and spleen using viral vectors. Prime-target immunization strategy could also be employed both as a therapeutic and prophylactic strategy against solid tumours, utilizing tumour-associated antigens expressed in viral vectors or encapsulated in particulates; Comprising of a priming vaccination at a highly immunogenic site (e.g. i.m.) and subsequently targeting immune responses to the tumour mass via an intra-tumoural administration or administration to the tissue of interest. An example, but not limited to, Adenovirus expressing prostate associated antigens could be administered i.m. followed by a subsequent vaccination of an oncolytic or non-oncolytic viral vector expressing the same tumour-associated antigen in a solid prostate tumour mass.

We show that prime and target immunization enhances liver-resident memory CD8+ T-cells and protection against liver-stage malaria.

It is important that the epitopes in the second composition (second administration/targeting administration) are the same as in the first composition (first administration), so that the T cells induced/expanded by the first administration are targeted by the second administration. In principle, all of the epitopes of the first composition should be present in the second composition. In other words the second composition should comprise all of the epitopes of the first composition. However in one embodiment it may be desirable to have one epitope (e.g. TRAP) in the first formulation and in the second formulation the same epitope as well as additional ones (e.g. TRAP-LSA1). In this embodiment the second composition comprises all of the epitopes of the first composition and also comprises at least one further epitope. Thus in one embodiment the invention relates to a kit, method, or use according to any preceding claim wherein at least one epitope in said first and second compositions is different, wherein said at least one different epitope is an additional epitope comprised by said second composition.

Further Advantages

It is an advantage of the invention that it is possible to use the same vector in the first and second or further compositions. The inventors believe that the view in the art is that the same vector cannot be used in short timescales such as those taught herein.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which:

FIG. 4 shows characterization of liver Ag-specific CD8$^+$ T-cells (A) Top: C57BL/6 mice (n=5) were primed with HAdV5-OVA ($1\times10^8$ iu) i.m. (Ad) and then received or did not receive PLGA-OVA Np i.v. two weeks post prime (Ad+Np). Three weeks post last vaccination, BrdU was subsequently injected i.p. 24 hrs and 6 hrs before livers and spleen tissues were harvested. Ag-specific CD8$^+$ T-cells were enumerated using Pen$^+$ staining, and BrdU$^+$ cells were determined by flow-cytometry. The results are expressed as % of total Pen$^+$ CD8$^+$ T-cells. Median value is shown. Data was analyzed with a Two-Way ANOVA and corrected for multiple comparisons using a Bonferroni's post-hoc test. $p<0.05$ (*); not statistically significant (ns). (B) Experimental schematic: Ly5.1$^+$ mice were primed with HAdV5-OVA ($1\times10^8$ iu) i.m. and then received PLGA-OVA Np i.v. two weeks post prime (Ad+Np). Spleen and liver tissues were subsequently harvested three weeks later, CD8$^+$ T-cells were negatively selected, and were stained with APC or CFSE respectively. Frequency of Pen$^+$ cells was determined by flow-cytometry and cells were re-transferred to a naïve Ly5.2 host in a 1:1 ratio. Recipient liver and spleens were then harvested one week post adoptive transfer. (C) Frequency of CFSE$^+$ or APC$^+$ Pen$^+$ CD8$^+$ T-cells of total lymphocytes in either liver or spleen of recipient mice. Median values are shown. Data was analyzed with a Mann-Whitney and corrected for multiple comparisons using a Dunn's post-hoc test. $p<0.05$ (*). (D) Liver:Spleen ratio of the frequency of CFSE or APC cells, or CFSE:APC ratio in respective organs is shown. Median values are shown. Data was analyzed with a Mann-Whitney test and corrected for multiple comparisons using a Dunn's post-hoc test. p<0.005 (**).

FIG. 19 (Supplementary FIG. 1) shows optimisation of immunisation regime timings for targeting Np dose. C57BL/6 mice (n=6) were primed with HAdV5-OVA (1×108 iu) i.m. and then received PLGA-OVA Np i.v. either on the day of prime (W0), one week post prime (W1) or two weeks post prime (W2), or they did not receive particles (Ad only). Three weeks after receiving the final immunisation livers were harvested and Ag-specific CD8+ T-cells were enumerated using Pen+ staining and intracellular IFNγ staining following ex vivo stimulation with SIINFEKL peptide. The results are expressed as total number of cells (A, B). Antigen specific CD4+ T cells in the liver were also stained for using an antibody raised against the OVA peptide specific variable chain of the TCR vα2/β5 shown as total number (C). Line shown represents the median of each group, analysis was performed using a One-Way ANOVA corrected for multiple comparisons using a Dunn's post-hoc test. p<0.05 (*); p<0.005 (**); not significant (ns).

FIG. 20 (Supplementary FIG. 2) shows T-cell recruitment to the liver is dependent on PLGA-OVA dose administered. C57BL/6 mice (n=4-5) were primed with HAdV5-OVA (1×108 iu) i.m. and two weeks later subsequently given either 10 μg (10 μg) or 25 μg (25 μg) PLGA-OVA Np i.v. either with or without adjuvant containing Np (adj). Livers (A,B) and spleens (C,D) were harvested after three weeks. Antigen specific CD8+ T-cells were assessed using SIINFEKL specific Pen+ and results are expressed as total numbers of CD8+ T-cells per organ (A,C) or as a percentage of total CD8+ T-cells (B,D). For each group, median are shown with a line. Data was analysed using a One-Way ANOVA and corrected for multiple comparisons using a Dunn's post-hoc test. p<0.005 (**); p<0.05 (*); not significant (ns).

FIG. 21 (Supplementary FIG. 3) shows T-cell recruitment to the liver is dependent on HAdV5 dose administered. C57BL/6 mice (n=6) were primed with HAdV5-OVA i.m. with different doses: 1×104 iu, 1×10$^6$ iu, and 1×10$^8$ iu. Two weeks later, PLGA-OVA Np i.v. (25 μg) were administered to all groups. Livers (A,B) and spleens (C,D) were harvested after three weeks. Antigen specific CD8+ T-cells were assessed using SIINFEKL specific Pen+ and results are expressed as total numbers of CD8+ T-cells per organ (A,C) or as a percentage of total CD8+ T-cells (B,D). For each group, median are shown with a line. Data was analysed using a One-Way ANOVA and corrected for multiple comparisons using a Dunn's post-hoc test. p<0.005 (**); p<0.05 (*); not significant (ns).

FIG. 22 (Supplementary FIG. 4) shows a prime and target approach protects mice in a transgenic *P. berghei* challenge model only using a relevant antigen. C57BL/6 mice (n=6) were primed with HAdV5-OVA (1×10$^8$ iu) i.m., after two weeks mice received i.v. PLGA-OVA (•) or PLGA-BSA (□) (25 μg protein). An additional unvaccinated group served as an infection control (○). Three weeks later all mice were challenged with 1000 transgenic *P. berghei* spz expressing OVA under the Hep17 promoter. Parasitemia was assessed using thin blood smear and time to 1% parasitemia calculated by linear regression. Survival curve analysis was performed using log rank Mantel-Cox test. p<0.001 (***).

FIG. 23 (Supplementary FIG. 5) shows a prime and target approach using viral vectors as targeting agents. (A-B) C57BL/6 mice (n=5-6) were primed with Ad5-OVA (1×10$^8$ iu) i.m. as previously described. Two weeks later mice received either Ad5-OVA i.v. (1×10$^9$ iu; Ad), MVA-OVA i.v. (1×10$^6$ pfu; MVA), or PLGA-OVA i.v. (1×10$^9$ iu; Np iv). Three weeks later, liver and spleen tissues were harvested for cytometry analysis and frequency of Pen$^+$ CD8$^+$ T-cells, IFNγ$^+$ CD8$^+$, and (B) CXCR6$^+$ CD69$^+$ Pen+CD8 T-cells was determined. Median values shown. Data was analyzed with a One-Way ANOVA and corrected for multiple comparisons using a Dunn's post-hoc test. p<0.05 (**). (C)

C57BL/6 mice (n=6) were primed with Ad5-OVA (1×10⁸ iu) im, after two weeks mice received Ad5-OVA (■) or MVA-OVA (▲) i.v. As control, mice received Ad-METRAP (AdHu5) (□) or MVA-METRAP (▼) or were primed and later received an iv vaccination with Ad-METRAP (AdHu5) ( ). An additional unvaccinated group served as an infection control (○). Three weeks later all mice were challenged with 1000 transgenic *P. berghei* spz expressing OVA under the Hep17 promoter. Parasitemia was assessed using thin blood smear and time to 1% parasitemia calculated by linear regression. Survival curve analysis was performed using log rank Mantel-Cox test. p<0.001 (***). (D) Similarly, C57BL/6 mice (n=6) were primed with Ad5-OVA (1×10⁸ iu) i.m., after two weeks mice received Ad5-OVA at different doses: 1×10⁴ iu (▲), 1×10⁶ iu (1), or 1×10⁸ iu (*). Three weeks later all mice were challenged with 1000 transgenic *P. berghei* spz expressing OVA under the Hep17 promoter, and parasitemia assessed as above.

FIG. 24 (Supplementary FIG. 6) shows a prime and target approach using viral vectors generates high numbers of HBsAg CD8⁺ T-cells in the liver. Balb/c mice (n=5) were primed with Ad5-HBsAg (1×10⁸ iu) im, or with 10,000 irradiated spz (iSpz) administered via i.v. route. Ater two weeks mice received Ad5-HBsAg i.m. or i.v. or alternatively MVA-HBsAg i.m. or i.v. Three weeks later, liver and spleen tissues were harvested for flow cytometry analysis and total IFNγ⁺ CD8⁺ T-cell count or frequency of IFNγ⁺ CD8⁺ T-cells was determined following ex-vivo IPQSLD-SWWTSL peptide stimulation. Median values shown. Data was analyzed with a One-Way ANOVA and corrected for multiple comparisons using a Dunn's post-hoc test. p<0.005 (**); p<0.05 (*).

FIG. 25 (Supplementary FIG. 7) shows a prime and target approach using viral vectors generates more Ag-specific CD8⁺ T-cells in both liver and spleen than irradiated sporozoites. C57BL/6 mice (n=6) were primed with Ad5-OVA (1×10⁸ iu) im, or with 10,000 irradiated spz (iSpz) administered via i.v. route. After two weeks mice received Ad5-OVA i.v. (iSpz Ad or Ad Ad). Alternatively, mice received 10,000 irradiated spz (iSpz) as a second dose (iSpz iSpz or Ad iSpz). Three weeks later, liver and spleen tissues were harvested for flow cytometry analysis and total cell count of Pen⁺ CD8⁺ T-cells and IFNg+ production following ex-vivo SIINFEKL stimulation was determined. Median values shown. Data was analyzed with a One-Way ANOVA and corrected for multiple comparisons using a Dunn's post-hoc test. p<0.0001 (**); p<0.001 (*); p<0.05 (*)

Figure 26:
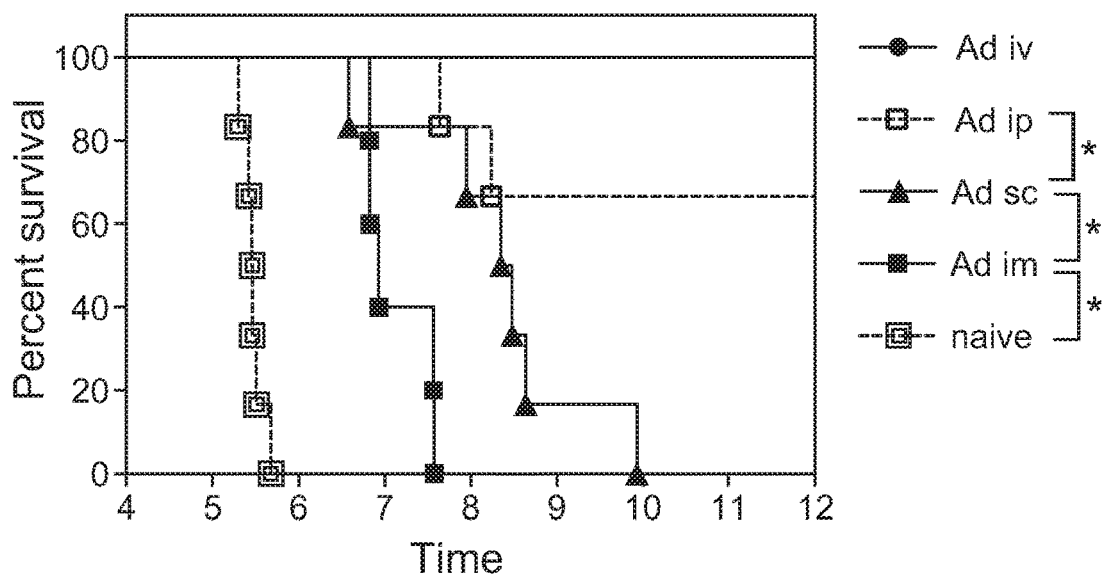

FIG. 26 shows a graph.

Figure 27:
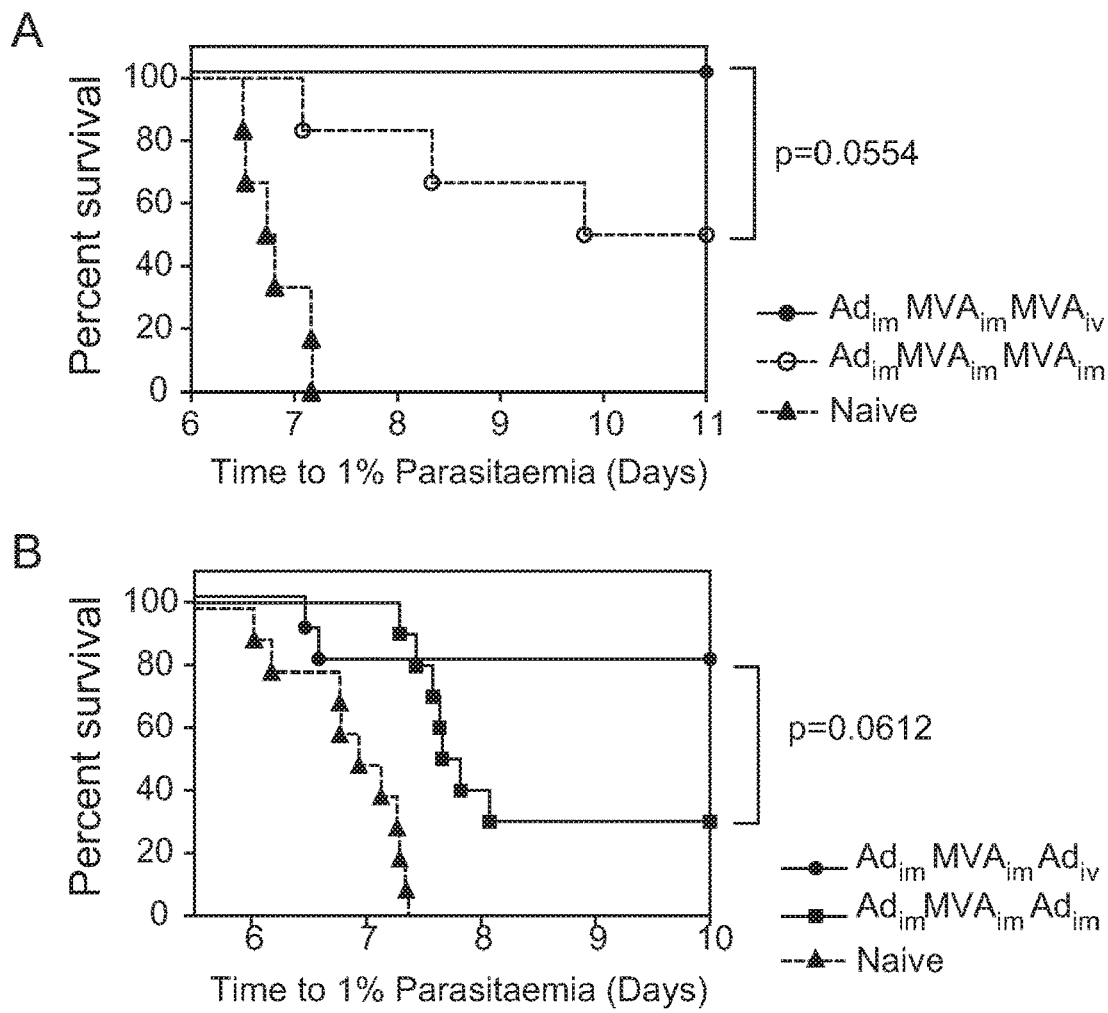

FIG. 27 shows prime-target data with Oxford ChAd vector ChAdOx1 and our clinical antigen LS2.

EXAMPLES

Although illustrative embodiments of the invention have been disclosed in detail herein, with reference to the accompanying drawings, it is understood that the invention is not limited to the precise embodiments and that various changes and modifications can be effected therein by one skilled in the art without departing from the scope of the invention as defined by the appended claims and their equivalents.

Example 1

In studies of T cell distribution in vaccinated mice the inventors found that levels of a relatively newly described population of CD8+ resident memory T cells, present in the livers of immunised mice, correlate very well with protection against sporozoite challenge. A threshold level of CD8+ T cells could be defined that correlates with complete protection. Such high numbers of resident memory T cells in the liver could be induced by a specific vaccination approach that utilises an intravenous dose of a viral vector (or antigen-loaded PLGA nanoparticles). This vaccination regime involves an initial dose of an adenovirus administered by the standard intramuscular route followed by an intravenous booster dose. Intravenous booster doses of either the recombinant adenovirus or recombinant MVA vector were shown to lead to prolonged antigen expression in the liver, suggesting that hepatic malaria antigen expression was needed to home or "target" antigen-specific circulating CD8+ T cells to the liver. This "prime-target" immunisation regime was initially demonstrated to induce 80% sterile protection with vectors encoding ovalbumin followed by challenge with transgenic *P. berghei* sporozoites expressing ovalbumin.

The optimal time point for intravenous boosting was at 2 weeks, with high level protection lasting for months.

Thus the invention relates to a readily manufactured subunit vaccine that could provide two dose high level efficacy in humans.

ME-TRAP ChAd and MVA vectors have already been tested extensively in clinical trials in the UK and Africa—but never with a heterologous second or further administration (such as an intravenous booster dose) as in the present invention.

We expect this approach to be safe because much higher doses of recombinant adenoviruses and vaccinia vectors have been tested safely intravenously in humans for therapeutic applications.

The invention offers the exceptional prospect of the first malaria vaccine with high level efficacy in humans.

The safety, immunogenicity and efficacy of this prime-target vaccination approach against malaria is to be assessed using available ChAd and MVA malarial liver-stage vectors, such as ChAdOx1, in a phase IIa sporozoite challenge trial design, of which we have considerable experience. A toxicology study in mice is to be carried out initially, followed by initial phase I safety testing of intravenous doses of the ChAd and MVA vectors (see below, Groups 1 & 2). This is to be followed by different vaccination regimes testing the use of an intravenous or subcutaneous (most suitably intravenous) booster of ChAd or MVA after intramuscular ChAd priming (groups 3 & 4); or an intravenous or subcutaneous (most suitably intravenous) ChAd dose after a full heterologous ChAd-MVA regime (group 5) or no priming dose (group 6).

This trial allows a rapid clinical assessment of this very exciting approach to malaria vaccination in humans.

Importantly, the same prime-target approach is applicable to other vaccination targets such as hepatitis B and hepatitis C immunisation.

| Clinical Trial Groups | | | |
|---|---|---|---|
| vector | dose | route | |
| Group 1a (single dose) | | | |
| a. ChAd | $5 \times 10^8$ vp | i.v. | n = 3 |
| b. ChAd | $5 \times 10^9$ vp | i.v. | n = 3 |
| c. ChAd | $5 \times 10^{10}$ vp | i.v. | n = 3 |
| Group 1b (single dose) | | | |
| a. ChAd | $5 \times 10^8$ vp | s.c. | n = 3 |
| b. ChAd | $5 \times 10^{10}$ vp | s.c. | n = 3 |
| c. ChAd | $2 \times 10^{11}$ vp | s.c. | n = 3 |
| Group 2 (single dose) | | | |
| a. MVA | $2 \times 10^6$ pfu | i.v. | n = 3 |
| b. MVA | $2 \times 10^7$ pfu | i.v. | n = 3 |
| c. MVA | $2 \times 10^8$ pfu | i.v. | n = 3 |
| Group 3 | | | |
| ChAd at 2 weeks | ChAd iv at 6 weeks | CHMI at week 10 | n = 8 |
| Group 4 | | | |
| ChAd at 2 weeks | MVA iv at 6 weeks | CHMI at week 10 | n = 8 |
| Group 5 | | | |
| ChAd at week 0 | MVA at week 4 | ChAd iv at week 6 CHMI at week 10 | n = 8 |
| Group 6 | | | |
| ChAd iv at 6 weeks | CHMI at week 10 | | n = 8 |

ChAd: ChAd ME-TRAP.
MVA: MVA ME-TRAP
ChAd dose in Groups 3-6: $5 \times 10^{10}$ vp;
MVA dose in Group 6: $2 \times 10^8$ pfu.
CHMI: controlled human malaria infection (with 5 infectious mosquito bites)

Synopsis of a Clinical Trial:
Grouping is
DNA(im)-MVA(iv)
AdHu5(im)-MVA(iv)
MVA(im)-MVA(iv)
non-prime-MVA(iv)
All tested for efficacy against malaria challenge.
Group 1: 50 ug DNA-TIP intramuscular Week 0, 10^6 pfu MVA-TIP administered iv at week 2, 1000 P. berghei sporozoites challenge at week 5
Group 2: 10^8 iu AdHu5-TIP intramuscular at week 0, 10^6 pfu MVA-TIP administered iv at week 2, 1000 P. berghei sporozoites challenge at week 5
Group 3: 10^6 pfu MVA-TIP intramuscular week 0, 10^6 pfu MVA-TIP administered iv at week 2, 1000 P. berghei sporozoites challenge at week 5
Group 4: 10^6 pfu MVA-TIP administered iv at week 2, 1000 P. berghei sporozoites challenge at week 5
Group 5: 1000 P. berghei sporozoites challenge at week 5 (Infection control)
BALB/c mice will be administered with 50 ug of DNA-TIP, 10^8 iu AdHu5-TIP or 10^6 pfu MVA-TIP all administered intramuscularly, whilst one group will not receive a prime vaccination. 2 weeks later all mice will receive a targeting vaccination with 10^6 pfu MVA-TIP administered intravenously and this will be followed by a challenge with 1000 P. berghei sporozoites 3 weeks later with all mice monitored for the development of blood-stage malaria. A group of unvaccinated mice will serve as an malaria infection control. TIP is an epitope string containing the immunodominant peptide from Plasmodium berghei circumsporozoite protein, termed Pb9. Prior to challenge the immune response to the Pb9 epitope will be measured in the blood of mice by intracellular cytokine staining after ex vivo stimulation of cells with the Pb9 peptide.

Example 2: Liver-Stage Malaria Model

To illustrate the prime-target approach, a P. berghei liver-stage malaria model was used. In this model, protection was known to require high levels of CD8$^+$ T-lymphocytes in the liver to kill infected hepatocytes (Reyes-Sandoval, A., et al., *CD8+ T effector memory cells protect against liver-stage malaria.* Journal of immunology, 2011. 187(3): p. 1347-57).

The prime-target approach was demonstrated using a murine model of malaria. P. berghei, a common animal model for the liver stages of a P. falciparum infection, has a highly unique life-cycle with an initial pre-erythrocytic phase. Importantly, liver stage malaria is asymptomatic, of brief duration (only two days in the context of P. berghei), and limited in Ag presentation due to Ag sequestration from the parasite, the establishment of a parasitophorous vacuole membrane (PV), and the small number of infected hepatocytes.

Probably due to the large size of the liver as an organ and lack of significant danger signals, there is a requirement for unusually high numbers of patrolling effector CD8$^+$ T-cells needed to recognize and kill (either directly or indirectly) infected hepatocytes at the time of sporozoite (spz) infection. In the context of liver stage malaria, protective liver resident memory CD8$^+$ T-cells have been described as expressing CXCR6, CD69, and CD103 (Tse, S. W., et al., *Unique transcriptional profile of liver-resident memory CD8+ T cells induced by im m unization with malaria sporozoites*. Genes and immunity, 2013. 14 (5): p. 302-9). Lastly, it is worth to note that aside from this unusually high requirement of circulating CD8$^+$ T-cells, liver stage malaria is further complicated by the fact that CD8$^+$ T-cell priming in the hepatic environment has been known to be suboptimal, often generating dysfunctional or exhausted immune responses. For these reasons, protection against liver stage malaria using traditional vaccination strategies is especially challenging. However, very high levels of CD8$^+$ T-cells in the liver have been shown to be protective, thus making *P. berghei* a suitable candidate for a prime-target approach to vaccination.

The strategy described here is composed of two parts: a first (priming) dose consisting of an Ad vector given i.m., known to generate high numbers of circulating T cells, followed by the second (targeting) dose, given intravenously (i.v.) to target CD8$^+$ T-cells to the liver. Targeting to the liver was achieved using either poly(lactic-co-glycolic acid) (PLGA)-protein loaded nanoparticles (NPs) or using viral vectors expressing the antigen of interest. By generating long-lived antigen specific CD8$^+$ T-cells resident in the liver, this new vaccination approach provides a substantial advance in clinically relevant malaria vaccine development, greatly improving efficacy over current heterologous viral vector prime-boost vaccine strategies.

Lastly, this approach is not limited to malaria could be applied to a wide variety of infectious and non-infectious diseases including therapeutic applications. To this end, the system was assessed and validated using Hepatitis B surface antigen (HBsAg) as an antigen. Hepatitis B is a chronic infection of the liver caused by Hepatitis B virus, complications of which include liver cirrhosis and liver cancer. In this study, the prime-target approach was able to induce a level of antigen specific T-cells in the liver, which was comparable to those observed in the previous *P. berghei* model.

Together, these experiments show that other antigens (either from an infectious pathogen or tumor associated) could be utilized as well as targeting to other sites, broadening the spectrum of diseases to which a prime-target strategy could be applied. In summary, this extends the heterologous prime-boost immunization strategy to include the concept of localization of T cell immune responses to the tissue of interest.

Vector and Nanoparticle Design:

For this patent, the model antigen OVA was used expressed in Human Adenovirus 5 (HAd5) vectors. Furthermore, Chimp Adenovirus ChAdOx1 expressing the following malaria antigens: PfLSA1 and PfLSAP2 has been used in addition to a HAd5 expressing the Hepatitis B Surface antigen (HBsAg). Unless otherwise stated, all antigens are expressed with a leader tPA sequence under a long CMV promoter, and inserted at the E1 locus of an E1/E3 deleted construct (making the viruses non-replication competent). Doses for vaccination were based on infectious units (iu).

Modified Vaccinia Ankara (MVA) viral vectors expressing similar antigens were also used. In short, MVA expressing the model antigen OVA and tdTomato were used, as well as MVA vectors expressing ME-TRAP, PfLSA1, PfTRAP and HBsAg. Poly(lactic-co-glycolic acid) (PLGA)-protein NPs were made using an oil-in-water-in-oil double emulsion. In brief, protein, specifically OVA, was suspended in water it was then emulsified with PLGA (Resomer, RG 502 H) in dichloromethane using sonication. This primary emulsion was then added to a larger volume of 1% PVA and sonicated to obtain nano droplets. The particles were precipitated by rapid removal of solvent under reduced pressure. Particle size was determined to be 300-400 nm using dynamic light scattering. Protein loading efficiency was determined to be 20-30% of starting protein.

Immunogenicity and Vaccinations

Female C57BL/6J, BALB/c or CD-1 (ICR) of at least 6 weeks of age were given a 1×10$^8$ iu Adenovirus i.m. immunization into the musculus tibialis (50 µl volume, diluted in PBS). Secondary "target" vaccinations were given two weeks later via i.v. administration (100 µl volume, diluted in PBS). Unless, otherwise stated, tissues were harvested three weeks post last vaccination.

In brief, mouse splenocytes were treated with ACK, prior to stimulation at 37° C. for 6 hours with 1 µg/ml of the CD8$^+$ immune-dominant epitope SIINFEKL, and/or the CD4$^+$ epitope ISQAVHAAHAEINEAGR and 1 µg/ml Golgi-Plug (BD). Similarly, liver lymphocytes were extracted through mechanical disruption of the tissue, followed by cell isolation on a 33% isotonic Percoll gradient, and ACK treatment. Cells were then stimulated as described above. Following stimulation, lymphocytes were labeled with a variety of different surface markers (live/dead, CD4, CD8, CXCR6, anti-SIINFEKL Tetramer (Tet+), CD69 and CD103) at 4° C. in the dark. Cells were fixed with neutral buffered formalin solution containing 4% formaldehyde, and then stained for the intracellular markers (IFNγ) diluted into Perm-Wash Buffer. Samples were then acquired on a BD Cantor LSRII flow-cytometer, and antigen specific cells identified by gating cells based on live/dead gating, followed by size, singlets, and expression of CD4$^+$ and CD8$^+$. Tet$^+$ or IFNγ$^+$ cells were then determined and data analyzed using FlowJo (Treestar) and Prism v6.0 (Graphpad).

Intravenous Sporozoite *P. berghei* Challenge

*P. berghei* infected *A. stephensi* mosquitoes were dissected at day 21 post-feed and sporozoites isolated from salivary glands. 1000 spz were administered via i.v. tail vein injection three weeks after the final vaccination unless otherwise stated. Thin blood films were obtained daily from day 3 post-infection, and stained with Giemsa for the presence of blood-stage parasites. Mice were monitored for positive blood-film and sacrificed at a human end-point of 1% or maintained for 15 days and considered sterilely protected if parasite free. The time to reach 1% parasitaemia is calculated using a linear regression model based on three consecutive blood films.

In this work, the following previously described transgenic *P. berghei* spz were used: OVA::Hep17$_{hep17}$, OVA:: mCherry$_{hsp70}$, PfLSA1@UIS4, and PfTRAP@UIS4 (Lin, J. W., et al., *The subcellular location of ovalbumin in Plasmodium berghei blood stages influences the magnitude of T-cell responses*. Infection and immunity, 2014. 82(11): p. 4654-65; Longley, R. J., et al., *Comparative assessment of vaccine vectors encoding ten malaria antigens identifies two protective liver-stage candidates*. Scientific reports, 2015. 5: p. 11820).

Figure 7:
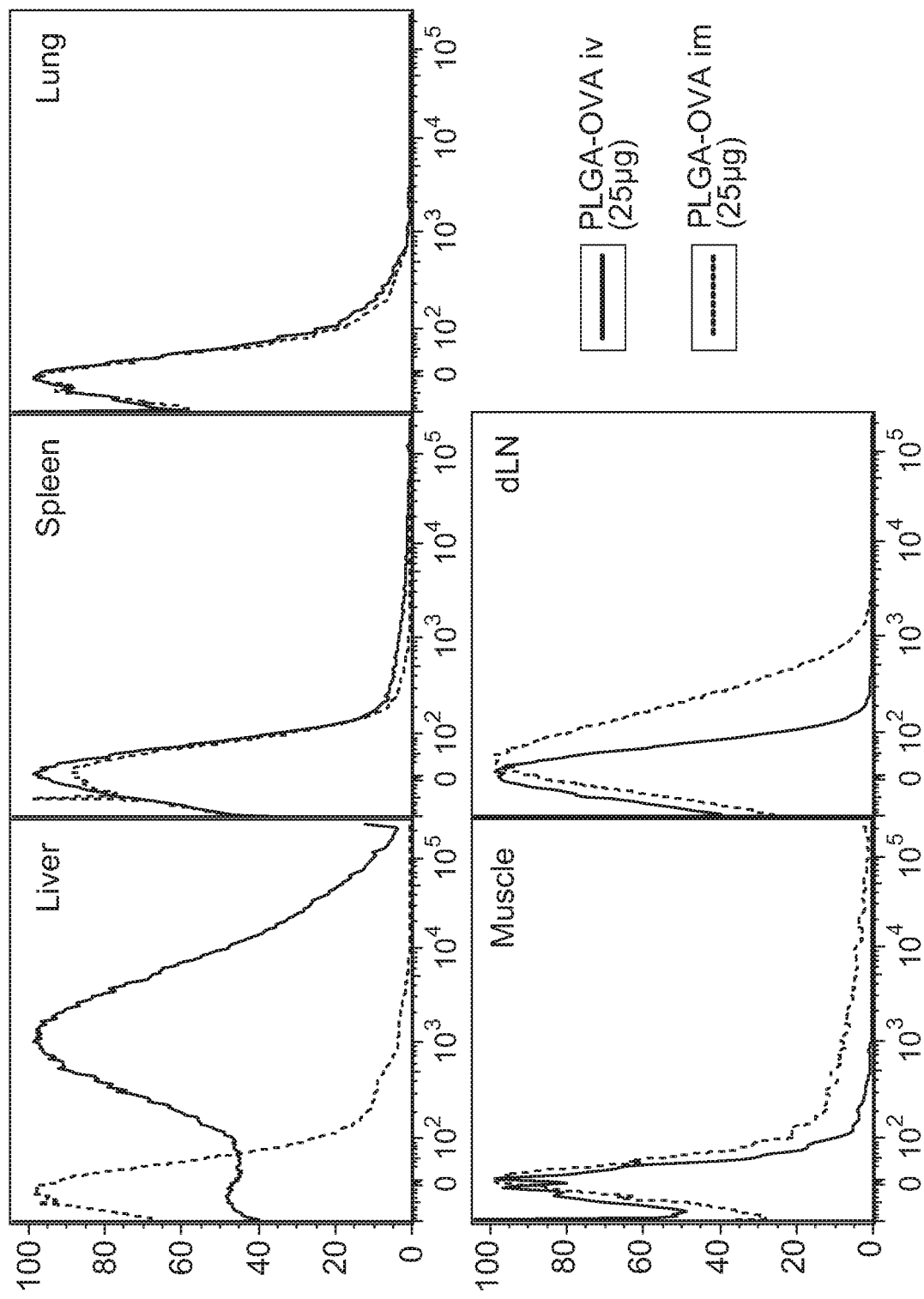
FIG. 7 shows plots
Figure 8:
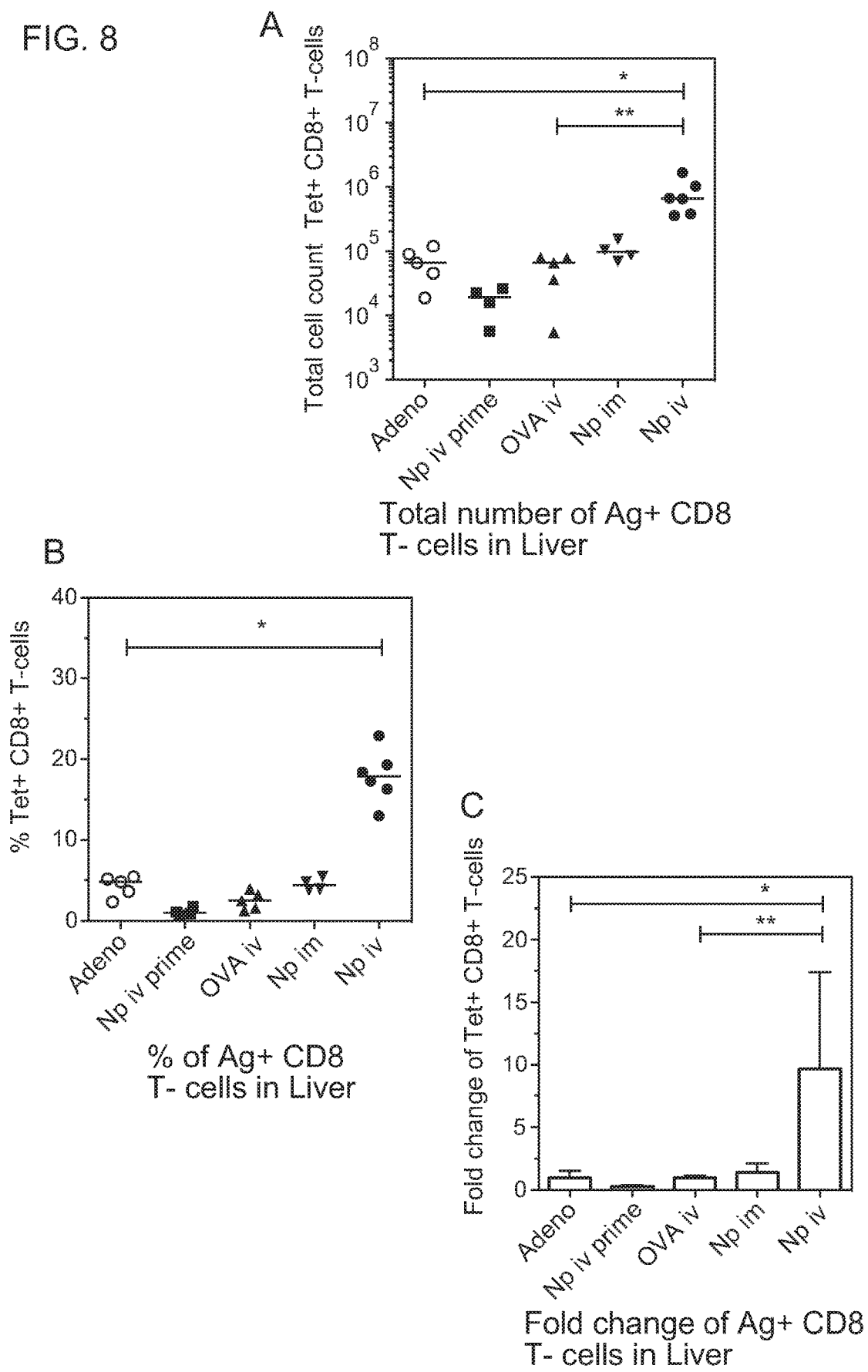
FIG. 8 shows graphs
Figure 9:
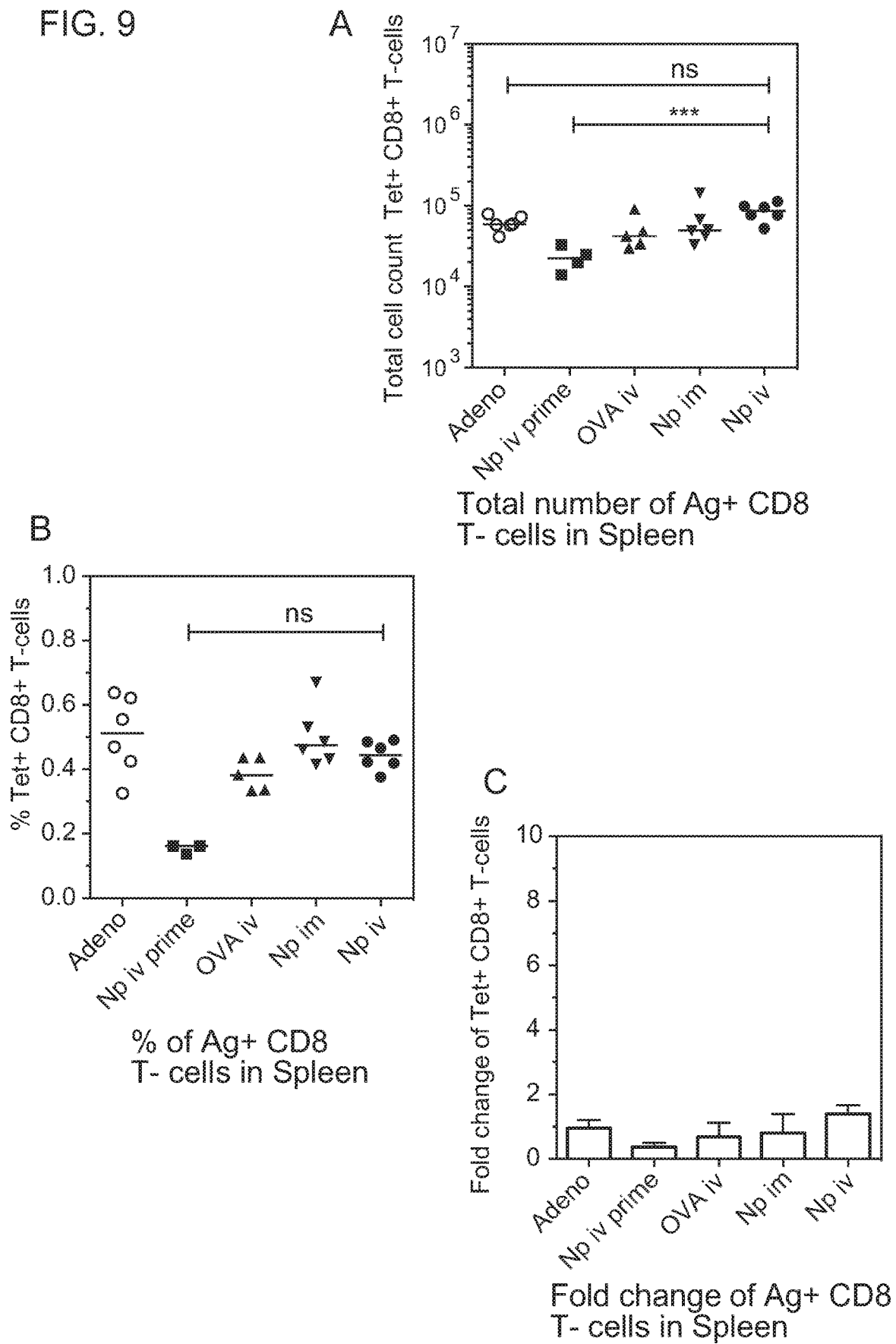
FIG. 9 shows graphs
Figure 10:
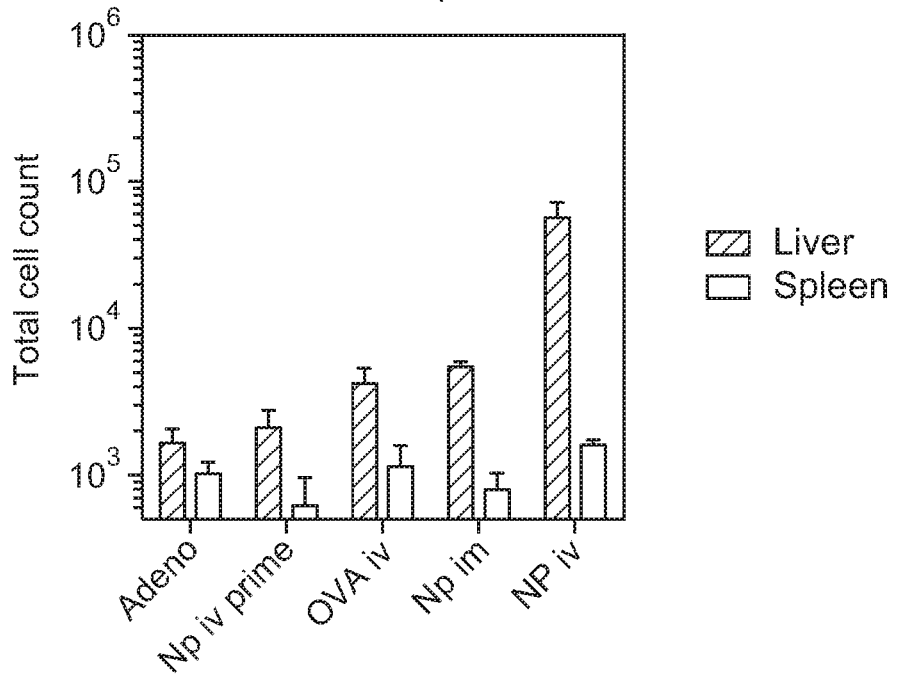
FIG. 10 shows a bar chart
Figure 11:
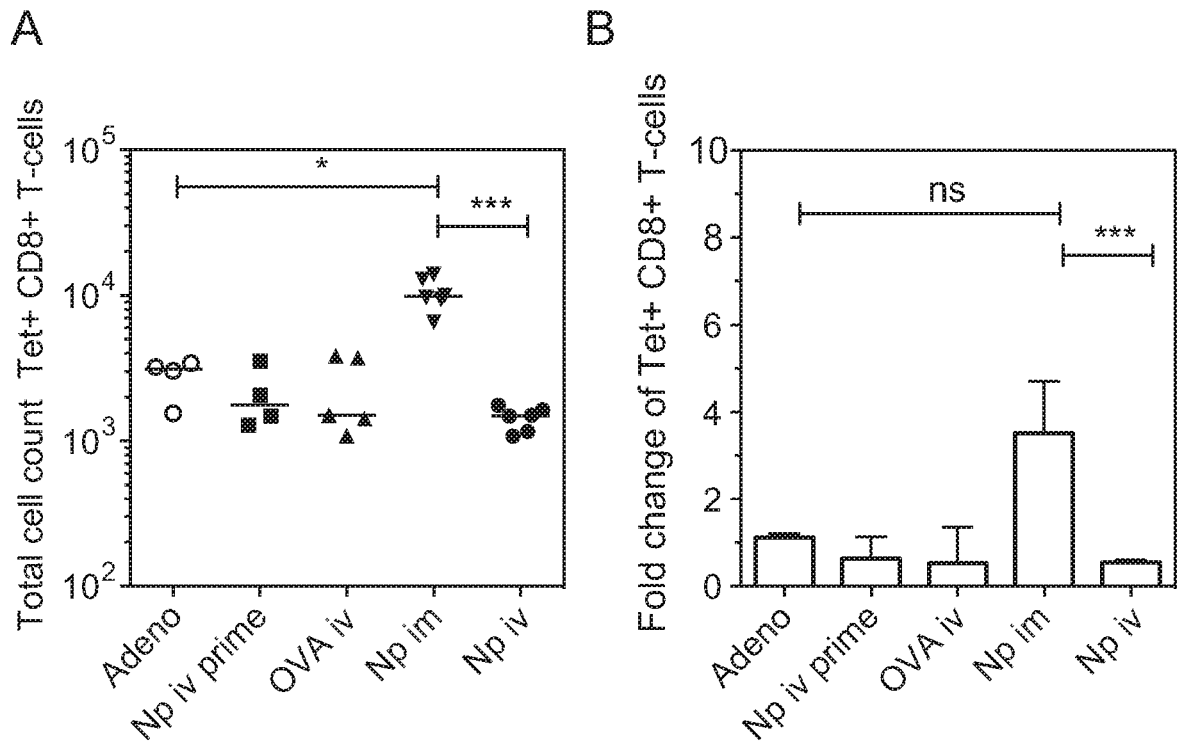
FIG. 11 shows plots. Total number of Tet+ CD8+ T-cells in dLN.

Example 3: Intravenous Administration PLGA-OVA Increases Hepatic Ag-Specific CD8$^+$ T-Cell Responses in a Prime-Target Regime To target Ag-specific CD8$^+$ T-cell responses to the liver following an intramuscular prime, PLGA NPs were first investigated as a targeting agent as they had previously been described to be easily retained in the liver. PLGA-APC-OVA NPs were prepared and following i.v. administration, their bio-distribution was determined 7 days post administration. Fluorescent signal was analyzed using flow cytometry, and it was determined that the majority of PLGA-APC-OVA following i.v. injection was in the liver after one week (FIG. 7). Having determined that PLGA NPs are delivered primarily to the liver, C57BL/6 mice were primed i.m. with HAd5-OVA ($1\times10^8$ iu) in the right limb. Two weeks later, at the peak of the Ad immune response, mice were vaccinated via tail vein i.v. administration of 25 μg of PLGA-OVA, 25 g OVA protein only, or not vaccinated at all. A control group of mice was included receiving 25 μg of PLGA-OVA via i.m. vaccination in the left limb. Furthermore, another control group was included, which received i.v. immunization only. Three weeks post last vaccination, liver, spleen and draining popliteal lymph nodes (dLN) were obtained and flow cytometry was performed. A ten-fold increase in tetramer-binding (Tet$^+$) Ag-specific CD8 T-cells in the liver following i.v. PLGA-OVA administration was observed, with no increase in any other group (FIG. 8A-C) or systemic tissues like the spleen (FIG. 9A-C). Using $CD6^9$ and $CXCR^6$ as markers of liver residency, Tet+ T-cells are shown to express markers for hepatic homing (FIG. 10). Lastly, a similar increase can be observed in the dLN following PLGA-OVA i.m. administration, emphasizing that the prime-target approach can be utilized to target Ag-specific cells to a variety of tissues (FIG. 11A-B).

Figure 12:
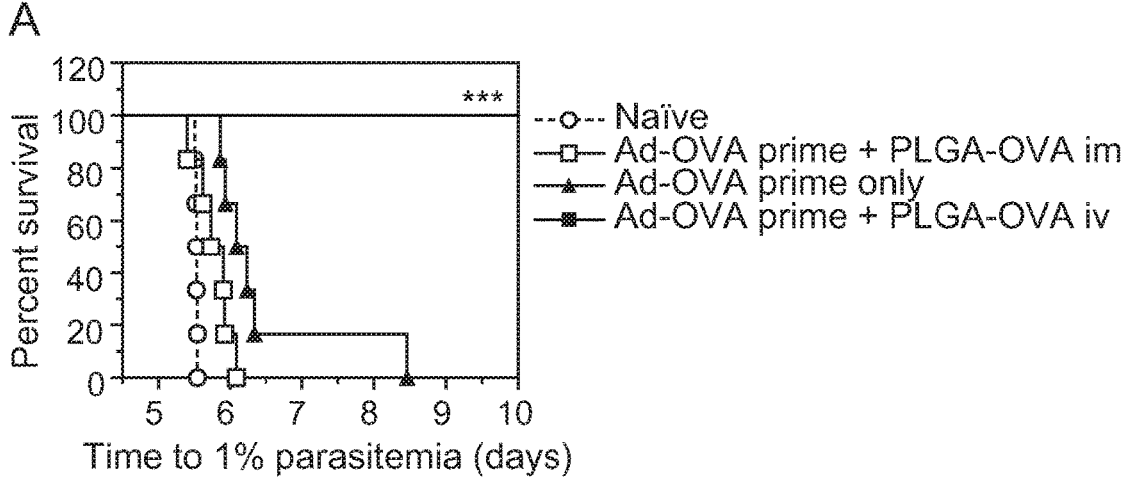
FIG. 12 shows plots

Example 4: Targeted Ag-Specific T-Cells are Protective in Two *P. berghei* Transgenic OVA Expressing Challenge Models As i.v. administration of PLGA-OVA NPs were shown to increase ten-fold the presence of liver localized Ag-specific CD8$^+$ T-cells (FIG. 8C). The level of protection conferred by this strategy was determined using a *P. berghei* transgenic spz challenge model, whereby 1000 spz were injected i.v. three weeks post last vaccination. The transgenic *P. berghei* line OVA::Hep17$_{hep17}$ expresses the model antigen OVA fused to $EXP_1/HEP_{17}$ (exported protein 1, hepatocyte erythrocyte protein 17 kDa) on the PVM membrane, previously suggested to induce particularly strong T-cell responses [18]. Mice were primed with HAd5-OVA i.m. and two weeks later PLGA-OVA NPs were either administered by i.v., i.m., or not administered as control. Administration of PLGA-OVA NPs i.v., resulted in sterile protection of 100% of mice (FIG. 12A). In contrast, only a small delay in time to 1% parasitemia was shown with other vaccinated groups as compared to naive group, with no sterile protection observed (FIG. 12A). To further test this vaccine regimen, mice were challenged with an OVA::mCherry$_{hsp7}$ *P. berghei* OVA transgenic spz line, expressing OVA in the parasite cytoplasm under the strong promoter of heat shock protein 70 (HSP$_{70}$) (Lin, J. W., et al., The subcellular location of ovalbumin in *Plasmodium berghei* blood stages influences the magnitude of T-cell responses. Infection and immunity, 2014. 82(11): p. 4654-65). Because of the intracellular location of OVA this parasite induces lower levels of T-cells responses. Again, only iv administered PLGA-OVA NPs as a targeting dose were able to sterilely protect challenged mice even in this more stringent model (FIG. 12B). Together, these data show that a prime-target strategy to the liver can result in protection from a *P. berghei* liver-stage malaria challenge.

Example 5: Intravenous Administration of Viral Vectors

Figure 13:
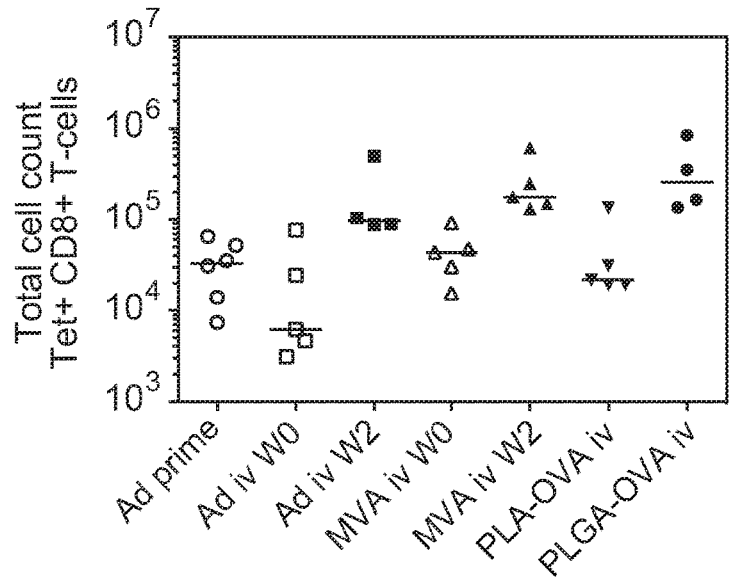
FIG. 13 shows a bar chart

Following the success to target Ag-specific CD8$^+$ T-cell responses to the liver with PLGA NPs, the use of viral vectors as an alternate targeting tools was investigated. C57BL/6 mice were primed i.m. with HAd5-OVA ($1\times10^8$ iu) in the right limb. Two weeks later, mice were vaccinated via tail vein i.v. injection with HAd5-OVA ($1\times10^9$ iu) or MVA-OVA ($1\times10^6$ pfu). Three weeks after the final vaccination, livers and spleens were obtained; and flow cytometry was performed to determine the number of Ag-specific T-cells. Surprisingly, similarly to PLGA-OVA, both Ad and MVA viral vectors were able to substantially increase the number of Tet+Ag-specific CD8 T-cells in the liver following i.v. administration (FIG. 13).

Figure 14:
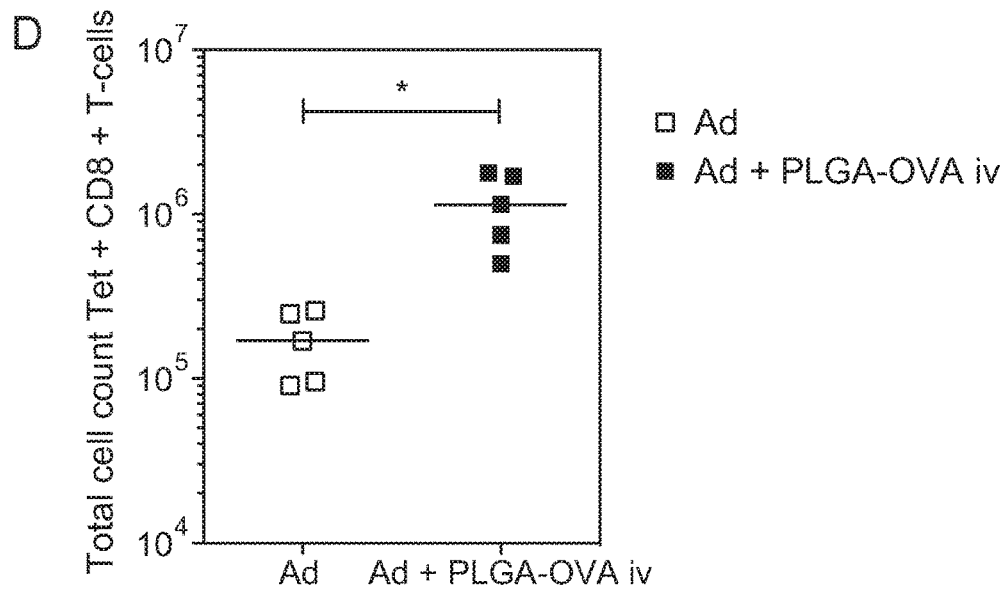
FIG. 14 shows plots and a graph

Example 6: Intravenous Administration of Viral Vectors is Protective in a *P. berghei* Transgenic OVA Challenge Model As i.v. administration of Ad or MVA viral vectors two weeks post prime showed similarly high levels of Ag-specific liver resident CD8$^+$ T-cells to PLGA-OVA NPs, the protective abilities of these viral vectors was assessed using *P. berghei* challenge model OVA::Hep17$_{hep17}$. Mice were all primed with HAd5-OVA i.m. and two weeks later a secondary targeting viral vector vaccination expressing OVA was administered via i.v. or i.m. routes as control. Administration of either vector i.m resulted only in 1.5 days delay to 1% parasitemia, with no sterile protection observed. All mice developed malaria. However, administration of either Ad or MVA viral vectors i.v. induced sterile protection in 83.3% of animals, with no significant difference between the use of i.v. Ad and i.v. MVA (FIG. 14A). Therefore, using viral vectors for T-cell targeting greatly improves overall vaccine efficacy compared to the use of the non-intravenous route.

To determine if protection waned over time, a similar experiment was set up comparing T-cell liver targeting with Ad, MVA or PLGA-OVA NPs regimens. Mice were then challenged two-months post final i.v. vaccination with *P. berghei* OVA::Hep17$_{hep17}$. Levels of protection were maintained two month post vaccination with all three targeting strategies, PLGA-OVA NPs achieving 100% sterile protection, and both viral vectors maintaining 83% sterile protection (FIG. 14B). The longevity of hepatic Ag-specific CD8$^+$ T-cells was further demonstrated in a kinetic study where Ag-specific CD8$^+$ T-cells are maintained at a steady level following PLGA-OVA NP administration (FIG. 14C), with the final time point at D 50 post last vaccination found to be in the same range as previous experiments (FIG. 14D).

Figure 16:
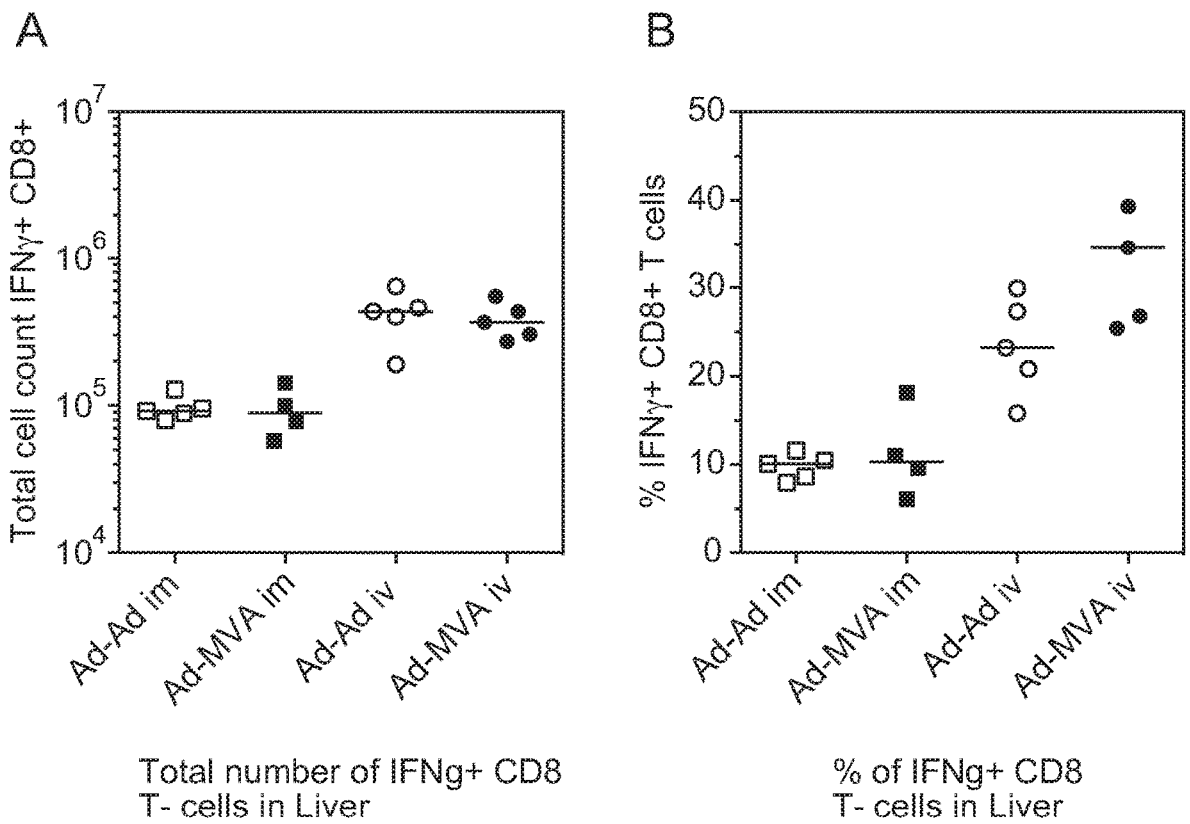
FIG. 16 shows graphs

Example 8: Validation of the System with Other Disease Models, Using HBsAg as a Model As the prime-target strategy was successful in generating high levels of Ag-specific CD8$^+$ T-cells in the liver, the system further tested using HBsAg as a model antigen. As before, BALB/c mice were primed with HAd5-HBsAg ($1\times10^8$ iu) i.m. and two weeks later a target i.v. 55 immunization was given either with HAd5 ($1\times10^8$ iu) viral vector, or MVA ($1\times10^6$ pfu). As previously seen, the prime-target approach substantially increased the presence of Ag-specific CD8$^+$ T-cells in the liver (FIG. 16A-B), validating the model with a non-malaria antigen. This finding shows that T cells against a hepatitis virus antigen can be targeted to the liver providing the opportunity to improve prevention and particularly immunotherapy of hepatitis virus infections.

In the context of this regimen, intra-muscular vaccination is simply a mechanism to induce circulating T cells. Therefore it is highly likely that booster targeting immunization could be used in the presence of a circulating T cell responses induced by a microbial pathogen or by a cancerous cell. It would be possible to target these circulating T cells to the liver or a selected mucosal surface by administration of PLGA particles or a viral vector, exactly as if the circulating T cells had been induced by immunization.

Example 9: Induction of $T_{RM}$ in the Liver

We describe here a novel type of vaccination strategy must be specifically be developed to induce high levels of long lived tissue-resident ($T_{RM}$) T-cells stationed in the liver, at the time of infection, thereby potentially bypassing the need for high numbers of circulating T-cells [17]. When present, $T_{RM}$ have been shown to accelerate protection against reinfections by regulating both the innate and adaptive immune systems [18, 19]. In the context of liver stage malaria, liver $T_{RM}$ have been described to require CXCR6 for their maintenance, and their persistence in the tissue has been proposed to associate with protection against malaria, after whole parasite immunisation [20-22].

We describe a new vaccination strategy aimed at inducing both high levels of circulating T-cells and subsequently increasing liver $CD8^+$ T-cells expressing residency markers. This prime and target approach requires two immunisations: a priming dose consisting of an Ad vector given i.m., known to generate high numbers of circulating T-cells, followed by a secondary vaccination, given intravenously (i.v.) to target $CD8^+$ T-cells to the liver. Targeting $CD8^+$ T-cells to the liver was achieved using either poly(lactic-co-glycolic acid) (PLGA)-protein loaded nanoparticles (Nps) or using viral vectors expressing the antigen of interest. By generating long-lived Ag-specific $CD8^+$ T-cells resident in the liver, this new vaccination approach provides a substantial advance in the observed efficacy of clinically relevant malaria vaccination strategies.

Results

A Prime and Target Regime with Intravenous Administration PLGA-OVA Nps Increases Hepatic Ag-Specific $CD8^+$ T-Cell Responses Resulting in Sterile Protection Particulates, have been described as being retained in the liver, a process that is mostly dependent on Np size [23]. Therefore, protein loaded PLGA Nps were investigated as agents to target Ag-specific $CD8^+$ T-cell to the liver. PLGA-APC-OVA Nps were generated with an approximate size of 350-400 nm (Suppl Table 1), and 7 days following i.v. or i.m. administration, their bio-distribution was determined by flow-cytometry and immunofluorescence. Following tail vein i.v. injection, PLGA-APC-OVA Nps were found to be predominantly concentrated in the liver in contrast to spleen or lung tissue (FIG. 1a), predominantly engulfed and internalized by Kupffer cells (FIG. 1b, Suppl Video 1). This was found to be route dependent as i.m. administration resulted in their localization to the proximal muscle or draining lymph node (dLN).

PLGA-APC-OVA Nps were generated with an approximate size of 350-400 nm Average protein loading was calculated by accurately weighing lyophilized product and hydrolyzing polymer with 0.1M NaOH and 1% SDS. The liberated protein was quantified using BCA assay, average loading of Np is shown. PLGA Np were sized using dynamic light scattering using a zetasizer. (n=15 batches of PLGA Np).

Average particle size was measured using a Zeiter-sizer. (n=15):

| Average PLGA Np loading (µg/ml of pellet) | Average Size (nm) |
|---|---|
| 1.655 ± 0.53 | 380 ± 30 |

7 days following i.v. or i.m. administration, their bio-distribution was determined by flow-cytometry and histology. Following tail vein i.v. injection, PLGA-APC-OVA Nps were found to be predominantly concentrated in the liver in contrast to spleen or lung tissue (FIG. 1A), predominantly engulfed by Kupffer cells (FIG. 1B). This was found to be route dependent as i.m. administration resulted in their localization to the proximal muscle or draining lymph node (dLN).

Figure 1:
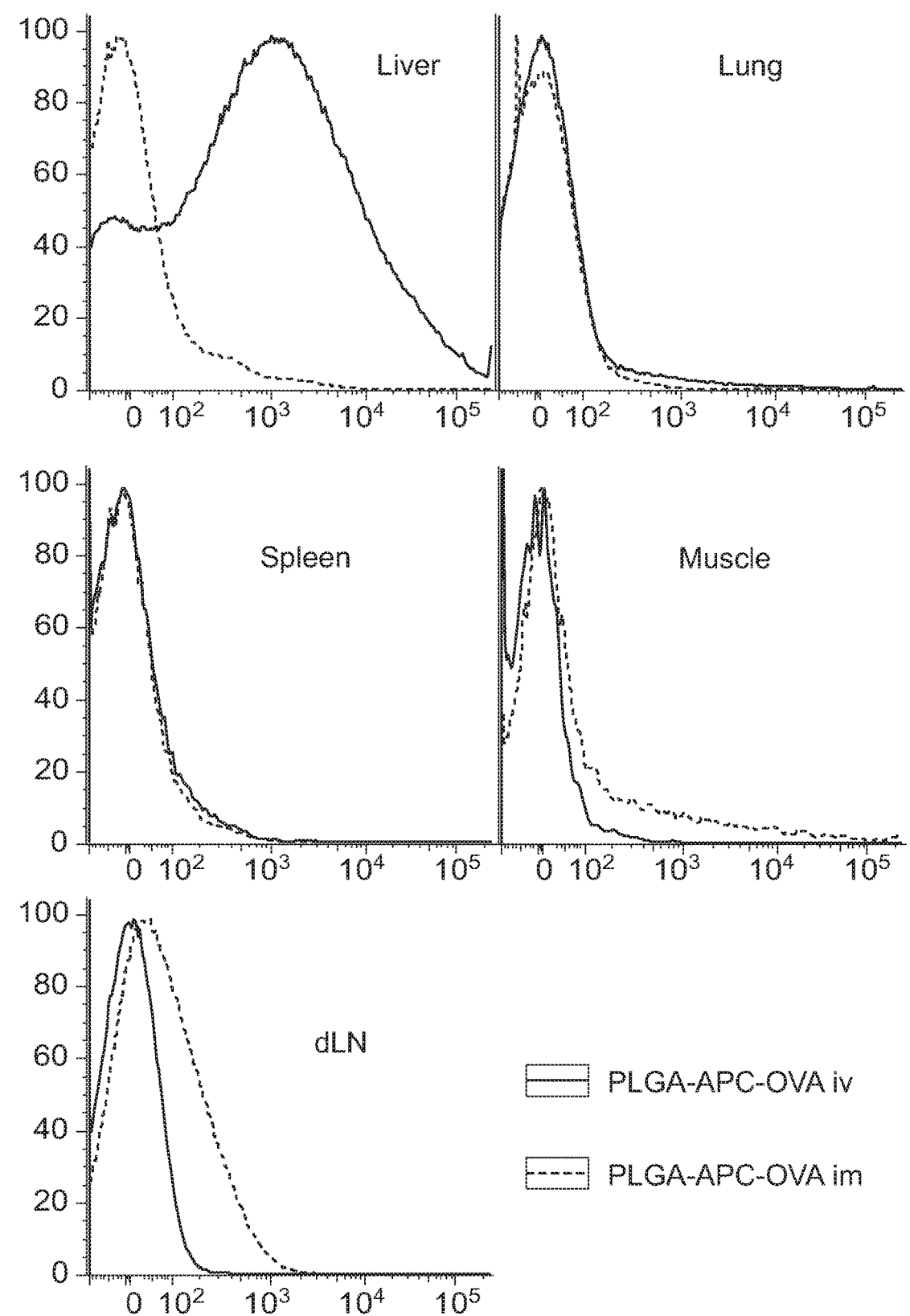
FIG. 1 shows intravenous administration of PLGA nanoparticles target preferentially the liver. (a) C57BL/6 mice (n=3) were vaccinated with i.v. or i.m. (see figure for key) with PLGA-APC-OVA Nps. After one week, liver, spleen, lung, muscle and dLN were harvested and presence of APC-OVA was detected on a flow cytometer. (b) Representative immunofluorescence staining of liver section from C57BL/6 mice vaccinated with PLGA-Rhodamine Nps one week post administration, quantification of total Nps association with Kupffer cell (F4.80$^+$), (n=4). (c) Experimental plan: mice were primed with Ad5-OVA i.m. (right limb) or i.v. 25 µg of PLGA-OVA (Np iv prime). Two weeks later, mice received i.v. administration of 25 µg of PLGA-OVA (Np iv), un-encapsulated OVA protein (OVA iv) or received i.m. administration of 25 µg of PLGA-OVA (Np im, left limb). Three weeks later, tissues were either harvested for cytometric analysis or, alternately, mice were challenged with spz to determine protection.
Figure 2:
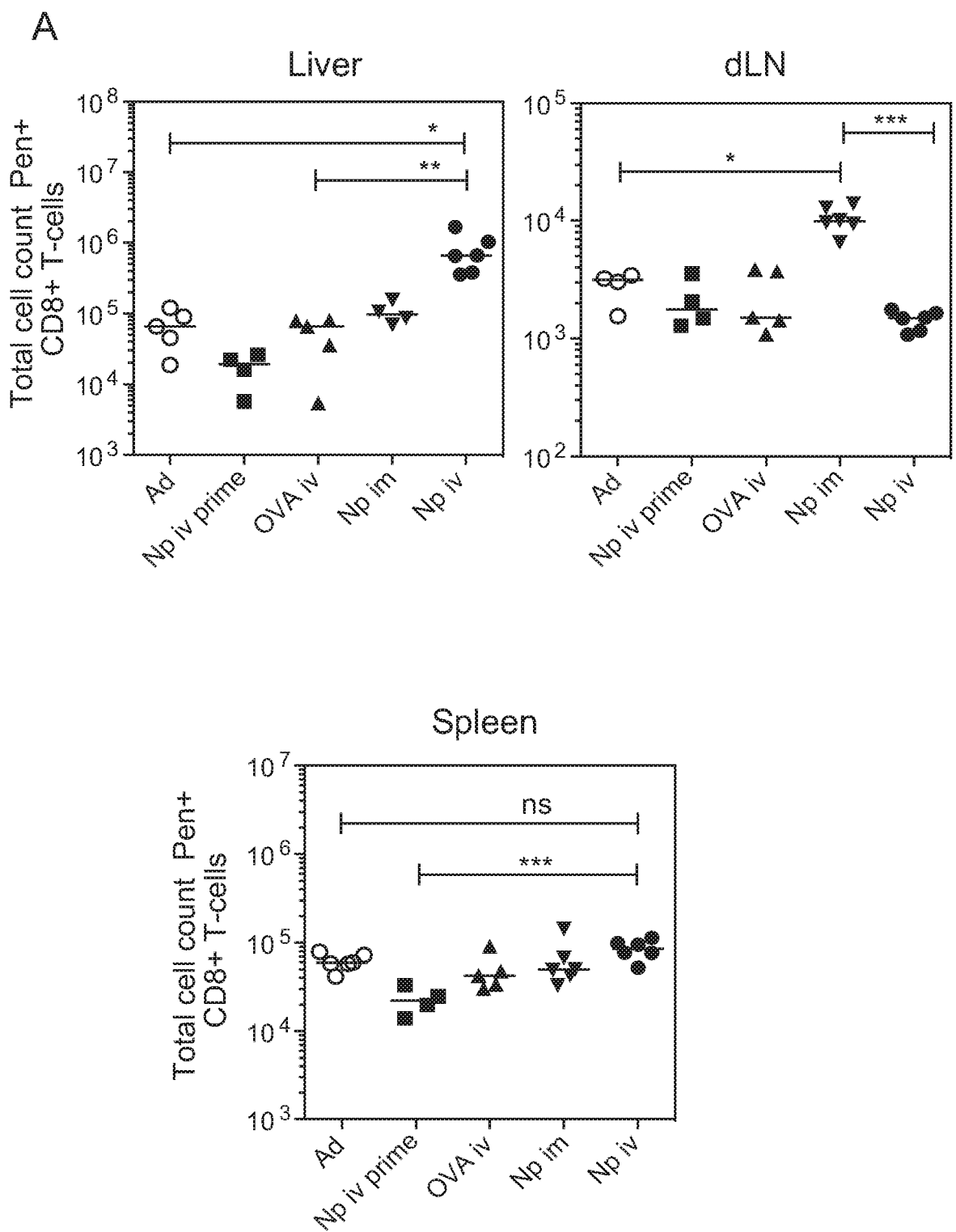
FIG. 2 shows a prime and target approach protects targeted mice in a transgenic $P.$ $berghei$ challenge model. (A) C57BL/6 mice (n=4-6) were primed with HAdV5-OVA ($1\times10^8$ iu) i.m. or with PLGA-OVA (25 µg protein) (Np prime). After two weeks, mice received 25 µg OVA protein (OVA iv), 25 µg PLGA-OVA either i.m. (Np im) or iv (Np iv), or did not receive any subsequent vaccination (Ad). Three weeks post administration, liver, dLN and spleen tissues were harvested and total cell count of Ag-specific CD8$^+$ T-cells determined via Pen$^+$ staining was determined. (B) Pentamer gating strategy: lymphocytes were gated on live, size and singlet population and subsequently gated on CD8$^+$ T-cells. Frequency of Pen$^+$ CD8$^+$ T-cells is shown. (C) Quantification of frequency of Pen$^+$ CD8$^+$ T-cells of total CD8$^+$ cells. (D) Frequency of IFN$\gamma^+$ CD8$^+$ T-cells of total CD8$^+$ cells following ex vivo stimulation with SIINFEKL peptide. (E) C57BL/6 mice (n=6) were primed with HAdV5-OVA ($1\times10^8$ iu) i.m., after two weeks mice received PLGA-OVA (25 µg protein) either i.m. (□) or i.v. (■), or did not receive PLGA-OVA (▲). An additional unvaccinated group served as an infection control (○). Three weeks later all mice were challenged with 1000 transgenic OVA::Hep17 $P.$ $berghei$ spz. Parasitemia was assessed using thin blood smear and time to 1% parasitemia calculated by linear regression. (E) The previously described experiment was performed using OVA::Hsp70 $P.$ $berghei$ spz. Median value are shown. Data was analyzed with a One-Way ANOVA and corrected for multiple comparisons using a Dunn's post-hoc test. $p<0.001$ (*); $p<0.005$ (); $p<0.05$ (*); not statistically significant (ns). Survival curve analysis was performed using log rank Mantel-Cox test. $p<0.001$ (***).
Figure 2:
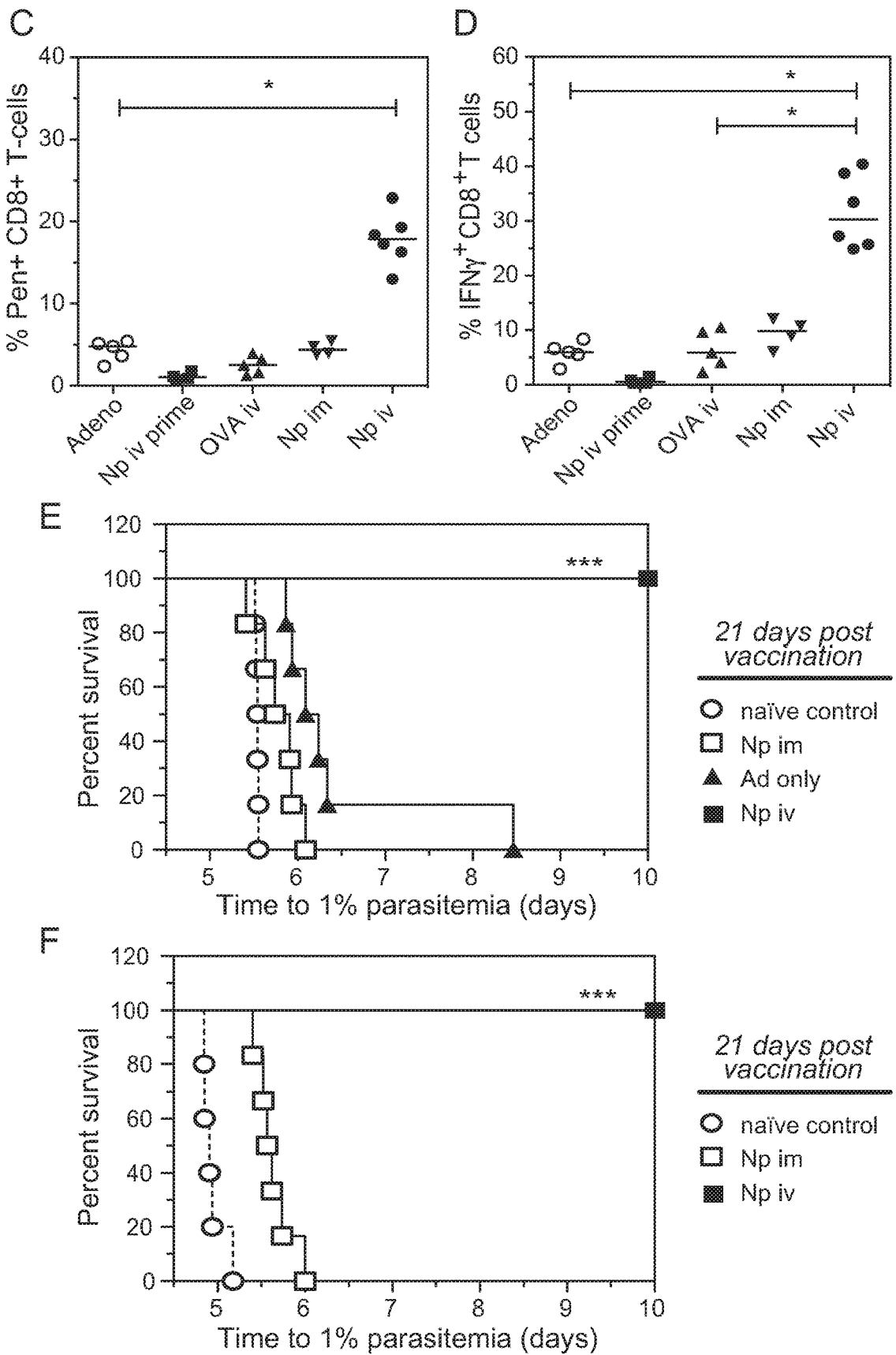
Figure 3:
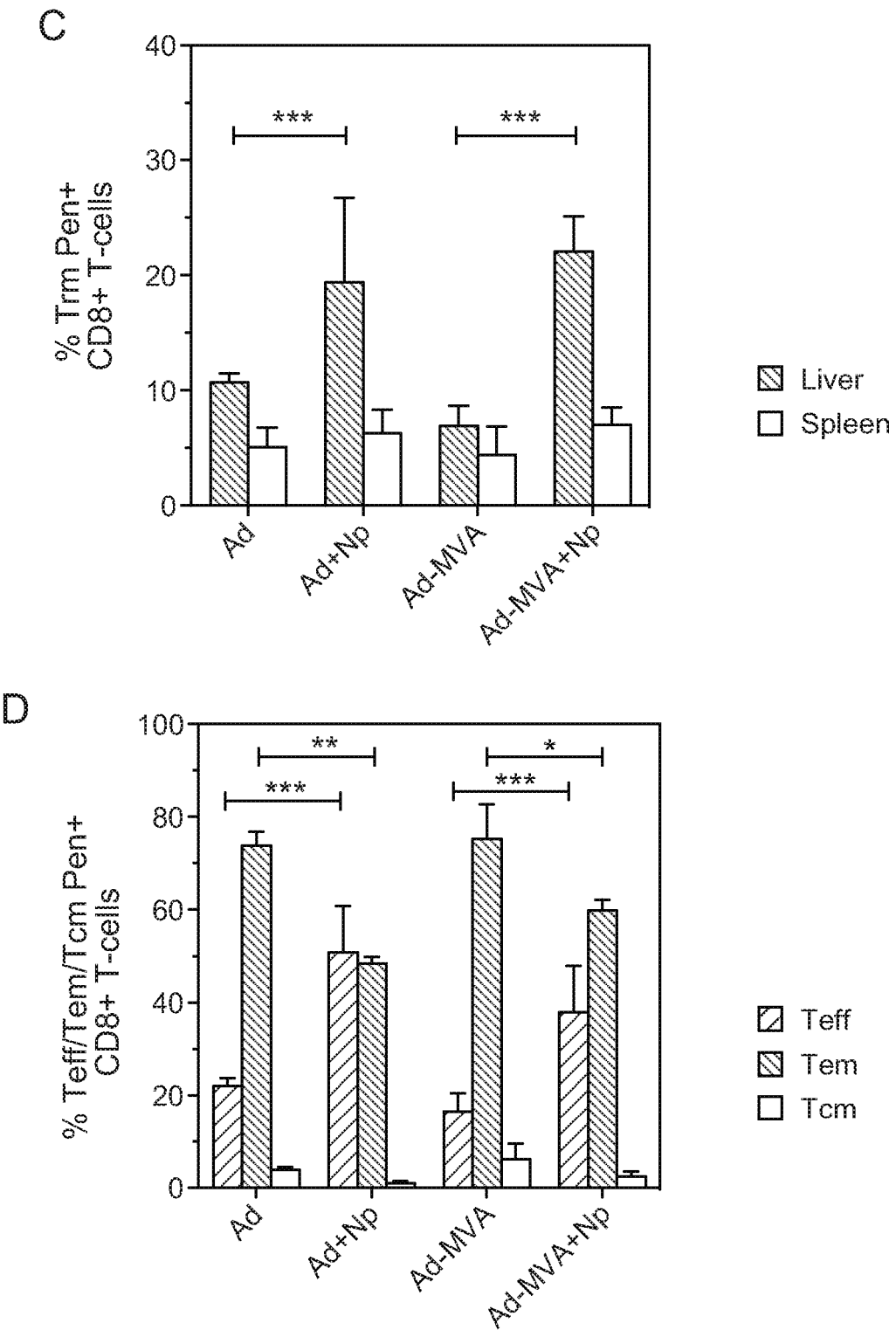
FIG. 3 shows Ag-specific CD8$^+$ T-cells are stably maintained in liver tissue, expressing markers of tissue residency. C57BL/6 mice (n=6) were primed with HAdV5-OVA ($1\times10^8$ iu) i.m. and then received PLGA-OVA Np i.v. two weeks post prime (Ad+Np). Alternatively, C57BL/6 mice (n=6) were primed with HAdV5-OVA ($1\times10^8$ iu) i.m. and subsequently boosted with i.m. MVA-OVA ($1\times10^6$ pfu) following by i.v. administration of PLGA-OVA Np i.v. 10 days later (Ad-MVA+Np). (A) Graphs represent the total number of OVA TCR$^+$ (V$\alpha_2$/V$\beta_5$) CD8$^+$ T-cells isolated from the liver of mice at the relevant time post vaccination. The start of the x-axis corresponds to the final viral vector immunisation, the vertical dashed line represents the time of Nps injection. The data was analyzed with a Two-Way ANOVA and post-hoc Bonferroni's test to compare between groups, $p<0.005$ () denotes the level of significance observed. (B) Total cell count of Pen$^+$ CD8$^+$ T-cells in livers and spleen was determined by flow cytometric at day 50 post vaccination. Data was analyzed with a One-Way ANOVA and corrected for multiple comparisons using a Dunn's post-hoc test. $p<0.005$ (); $p<0.05$ (*); not statistically significant (ns). (C) Frequency of Trm (CXCR6$^+$ CD69$^+$ Pen$^+$ CD8$^+$) T-cells of total Pen$^+$ CD8$^+$ T-cells in liver (grey) and spleen (white) at day 50 following various vaccination strategies. Data was analyzed with a Two-Way ANOVA and corrected for multiple comparisons using a Bonferroni's post-hoc test. $p<0.001$ (*). (D) Frequency of Teff (black, CD62L$^-$ CD127$^-$), Tem (grey, CD62L$^-$ CD127$^+$) and Tcm (white, CD62L$^+$ CD127$^+$) Pen$^+$ CD8$^+$ T-cells, of total Pen$^+$ CD8$^+$ T-cells in liver at day 50 following various vaccination strategies. Data was analyzed with a Two-Way ANOVA and corrected for multiple comparisons using a Bonferroni's post-hoc test. $p<0.001$ (*); $p<0.005$ (**); $p<0.05$ (*). (E) Gating strategy comparing an Ad and Ad+Np vaccination regime in liver at day 50 for CXCR6 and CD69 T-cell expression and CD127 and CD62L for memory phenotype markers of total Pen$^+$ CD8$^+$ T-cells. In quadrants, frequency of each cell population is shown.
Figure 3:
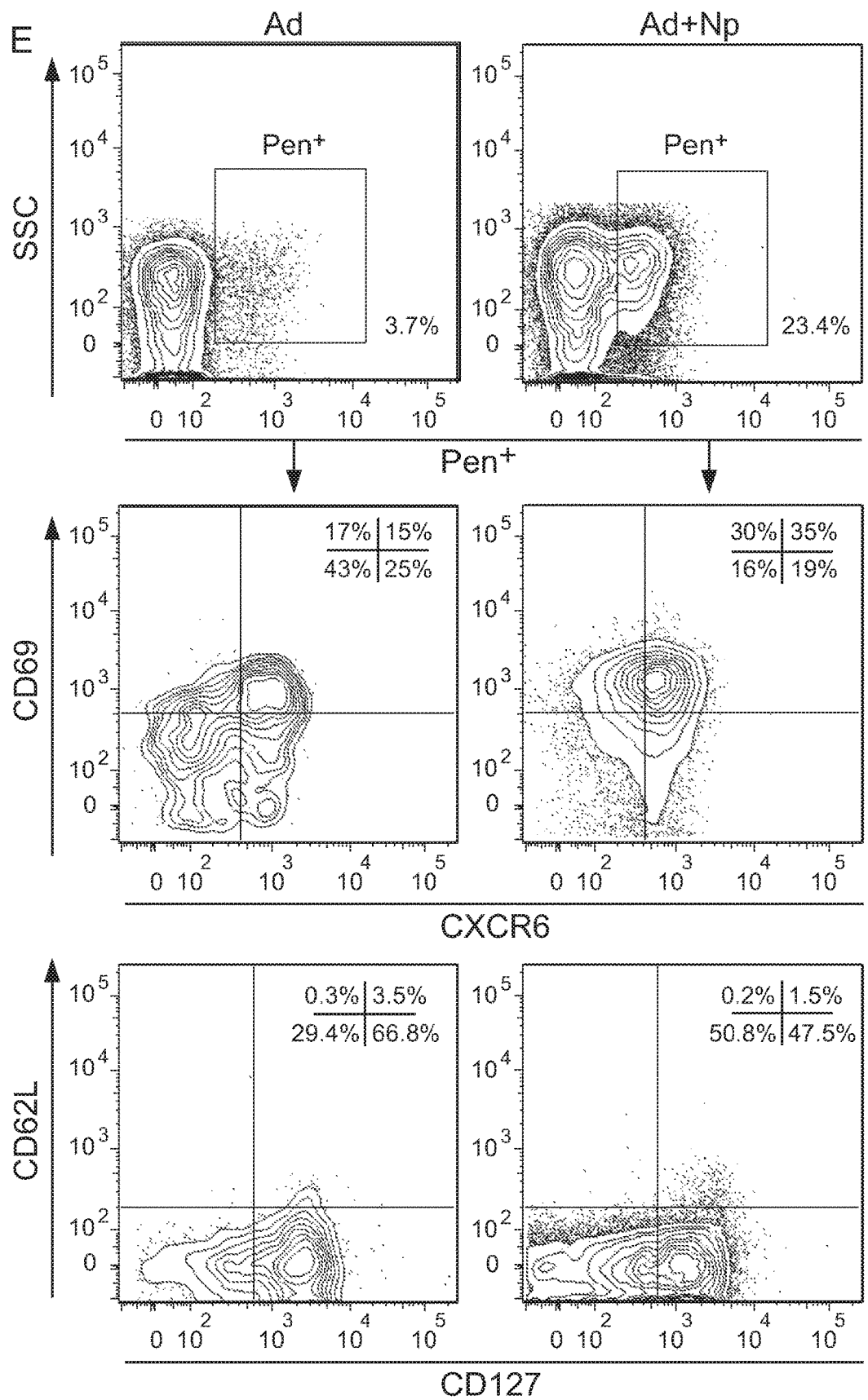

Having confirmed that i.v. administration of Nps results in liver localization, their ability to target circulating Ag-specific effector $CD8^+$ T-cells to the organ was investigated. C57BL/6 mice were primed i.m. with Human Adenovirus 5 expressing ovalbumin (Ad5-OVA) in the right limb. Two weeks later around the peak of the Ad5 immune response (previously determined [24]), mice received i.v. administration of PLGA-OVA Nps or un-encapsulated OVA protein (FIG. 1C). Another group of mice received an i.m. (left limb) administration of Nps. Three weeks post targeting, cells extracted from the liver, spleen, and popliteal dLN, were analyzed by flow cytometry (FIG. 2A). A ten-fold increase both in frequency and total number of SIINFEKL-Pentamer ($Pen^+$) Ag-specific $CD8^+$ T-cell was observed in the liver following i.v. PLGA-OVA administration, with no increase in any other vaccination group observed at this time point (FIG. 2B, C). Consistent with $Pen^+$ staining, a higher percentage of liver IFNγ$^+$ $CD8^+$ T-cells was observed following ex-vivo SIINFEKL peptide stimulation in the PLGA-OVA Nps vaccinated mice compared to all other groups (FIG. 2D). A similar increase in total number of $Pen^+$ $CD8^+$ T-cells can also be observed in the dLN following PLGA-OVA i.m. administration, indicative of local targeting (FIG. 2A). Importantly, Np administration did not systemically boost circulating $CD8^+$ T-cell numbers, as no difference was observed across all groups in circulating spleen Ag-specific $CD8^+$ T-cells (FIG. 2A). Timing of Np administration was optimized, with the highest Ag-specific T-cells recruitment observed at two weeks post i.m. prime, and the magnitude of the response was observed to be dose dependent (Suppl FIG. 1, 2). Adjuvanting PLGA Nps containing MPLA and R837, shown to increase T-cells responses [25], had only minor effects in increasing liver Ag-specific $CD8^+$ T-cells, a trend only observed at lower antigen doses. In accordance with the literature, Ag-specific $CD8^+$ T-cells primed in the liver showed higher frequency of PD-1 expression, a marker for exhaustion (Suppl FIG. 3).

The level of protection conferred by this strategy was determined using a *P. berghei* transgenic spz challenge model, whereby 1000 spz are injected i.v. three weeks post last vaccination. The transgenic parasite line OVA::Hep17$_{hep17}$ expressing the model antigen OVA fused to $EXP_1$/$HEP_{17}$ (exported protein 1, hepatocyte erythrocyte protein 17 kDa) in the Parasitophorous vacuole membrane (PVM) [25]. Administration of Nps i.v., resulted in 100% sterile protection of mice (FIG. 2E), in contrast no sterile protection and only a small non-significant delay in time to 1% parasitaemia was observed in all other groups. In a more stringent model, mice were challenged with an OVA::m-

Cherry$_{hsp70}$ P. berghei transgenic spz, expressing OVA in the parasite cytoplasm under the strong promoter of heat shock protein 70 (HSP$_{70}$) [25]. Because of the intracellular location of OVA, this parasite has previously been shown to induce lower levels of T-cell responses. Again, only i.v. administered Nps were able to sterilely protect 100% of challenged mice (FIG. 2F). Importantly, administration of an irrelevant encapsulated protein (PLGA-BSA Nps) as targeting dose did not confer any protection (Suppl FIG. 3); suggesting that protection from liver-stage malaria conferred by this immunisation regimen is antigen specific.

Ag-Specific CD8$^+$ T-Cells Targeted in the Liver Express Markers of Tissue Residency and are not a Transient Population To determine the longevity of Ag-specific CD8$^+$ T-cells in the liver, mice were vaccinated with the standard prime and target regimen and lymphocytes isolated from tissues were obtained at a number of different time-points and analyzed by flow-cytometry. The number of Ag-specific CD8$^+$ T-cells in the liver was determined by staining with an anti-OVA TCR antibodies (TCR V$\alpha_2$/V$\beta 3_5$) (FIG. 3A, top) [26]. Alternatively, mice vaccinated with a heterologous viral vector prime-boost regimen (Ad-MVA) received a target vaccination with i.v. Np, to determine if numbers of Ag-specific CD8$^+$ T-cells in the liver could be further increased by an initial regimen known to induce higher numbers of CD8$^+$ T-cells than vaccination with Ad alone. For this vaccination regimen, at the peak of the MVA response [27], Nps were administered i.v. (FIG. 3A, bottom). Both vaccination regimens induced a relatively stable population of liver Ag-specific CD8$^+$ T-cells, with a 7-9 fold increase in total number of Pen CD8$^+$ T-cells maintained until at least 50 days post vaccination. The increased number of Ag-specific CD8$^+$ T-cells induced by targeting vaccination with i.v. Nps was shown to be liver specific, as there was no difference observed in the spleen at the same time point (FIG. 3B).

Further phenotypic characterization of liver Ag-specific CD8$^+$ T-cells revealed that Np administration significantly induced a higher frequency of Ag-specific cells expressing CXCR6 and CD69 (FIG. 3C, E), common markers for liver tissue residency and tissue maintenance [17]. Furthermore, CD62L and CD127 staining for differentiation into T-effectors (T$_{EFF}$), T-effector memory (T$_{EM}$), and T-central memory cells (T$_{CM}$) populations, revealed a large fraction of liver Ag-specific cells had down regulated CD127 expression (FIG. 3D, E), a phenotype previously described to be associated with T$_{RM}$ cells [28]. Proliferation of Ag-specific CD8$^+$ T-cells, assessed by intra-peritoneal BrdU administration, was found to be slightly higher than in control mice, albeit not statistically significant (FIG. 4A). To determine if liver T$_{RM}$ were able to home back to their tissue of residence in the absence of antigen, spleen and liver tissues were harvested from Ly5.2$^+$ animals following a prime and target vaccination, cell preparations enriched for CD8$^+$ T-cells prior to intracellular dye labeling with APC (for spleen) or CFSE (for liver). Pen$^+$ CD8$^+$ T-cells from livers or spleens were mixed in a 1:1 ratio and injected in naïve recipient hosts (on a L5.1$^+$ background), with spleens and livers harvested seven days later (FIG. 4B). Although injected in a 1:1 ratio, in the liver a higher frequency of liver derived CD8$^+$ T cells were observed compared to spleen derived cells, conversely in the spleen a higher frequency of spleen derived CD8$^+$ T cells were observed compared to liver derived CD8$^+$ T cells (FIG. 4C). When comparing the frequency of liver derived or spleen derived cells which had relocated back to either organ, liver derived T-cells where shown to preferentially home back to the liver resulting in a higher ratio of liver derived cells in the liver compared to spleen (FIG. 4D right panel), and higher ratio of cells in the liver being of a liver derived origin (FIG. 4D left panel). In contrast, spleen derived cells did not preferentially home as there was an equal distribution of cells between the two organs (FIG. 4D). In summary the data would suggest that the prime-target vaccination regimen induces high frequency of cells liver T$_{RM}$ cells, in terms of both their phenotype (CD69$^+$ CXCR6$^+$ CD127$^-$) and preferential localization in the liver on reinjection.

Viral Vector Intravenous Administration can be Used as an Alternative Targeting Approach Having determined that high liver antigen delivery significantly enhances the frequency of CD8$^+$ T-cells expressing residency markers, the capacity of clinically tested adenoviral and MVA vectors as a liver antigen-delivery method was assessed. These non-replication competent viral vectors are known to stably express proteins, with each vector exhibiting a unique kinetics profile [29]. Importantly, they have shown good safety profiles in humans following both i.m. and i.v. routes of administration [29-31]. Human Ad5, and MVA viral vectors containing a luciferase (Luc) cassette were administered via i.v. in mice, and bioluminescence imaging was performed over time (FIG. 5A). Quantification of region of interest (ROI) photon flux intensity, revealed that both the human and simian Ad viral vectors are highly liver tropic with strong and stable luciferase expression (FIG. 5B). MVA also displays some liver tropism with low luciferase expression very shortly after i.v. administration, while over time briefly residing in the spleen.

Immunogenicity of i.m. Ad5 prime followed by Ad5 or MVA i.v. targeting administration was investigated. Targeting i.v. injection of both Ad5 and MVA were able to generate substantial numbers of Ag-specific CD8$^+$ T-cells in liver, comparable to that achieved by Np i.v. in liver. The increase in Ag-specific cells was not restricted to the liver as higher numbers of Ag-specific CD8$^+$ T-cells was observed in the spleen (FIG. 5C, Suppl FIG. 5A). In accordance, a high frequency of IFNγ+CD8$^+$ T-cells was observed, as well as markers of tissue residency (Suppl FIG. 5A, B). More importantly, the ability of these vectors to enhance Ag-55 specific cells to the liver is not restricted to model antigens, as a high number of Hepatitis B surface Antigen (HBsAg) CD8$^+$ T-cells could be induced in the liver in a similar manner using Ad and MVA viral vectors (Suppl FIG. 6).

To determine if i.v. administration of viral vectors led to enhanced protection, prime-targeted vaccinated mice were challenged with OVA::Hep17$_{hep17}$ P. berghei spz three weeks after the final vaccination (FIG. 5D). While administration of Ad5 or MVA via the i.m. route produced a delay in time to 1% parasitaemia, administration of either viral vector i.v. significantly enhanced protection, resulting in 80% sterile efficacy. Protection was found to be dose dependent, with higher targeting doses resulting in increased delay to 1% parasitaemia and higher sterile protection (Suppl FIG. 5D). Efficacy mediated by the prime-target regimen was shown to be antigen specific, as vaccination with the same regimen expressing a different antigen did not confer any degree of sterile efficacy (Suppl FIG. 5C). Crucially, levels of protection did not decline significantly over time. Mice vaccinated with a prime and target approach using either Ad5, MVA or Nps were challenged 8 weeks after last vaccination (FIG. 5E). Target vaccination with Np i.v. conferred sterile protection in all animals, while both viral vectors exhibited 80% sterile protection, with unprotected animals having a significant delay in time to 1% parasitaemia. In contrast, administration of either Ad5 or MVA viral vectors i.m showed only a small delay in the time to 1% parasitaemia. Importantly, when Ad given i.v. was used to target CD8+ T-cells induced by vaccination with i.v. administered irradiated spz (an alternative clinical vaccination regimen) a significant increase in the number of Ag-specific cells in the liver was induced compared to vaccination with irradiated spz alone. However, the highest frequency of Ag-specific cells was induced by prime-targeting vaccination with Ad5 i.m. and Ad5 i.v. (Suppl FIG. 7). In summary, the data demonstrate that prime-target vaccination with Ad5 or MVA results in a significant increase in Ag-specific liver cells of a $T_{RM}$ phenotype, and enhanced protection from liver-stage malaria.

Conclusion

In an effort to develop a pre-erythrocytic vaccine strategy involving CD8+ T-cells mediated protection, a prime and target approach was developed. Here, we show that high antigen delivery to the liver with PLGA protein loaded Nps, resulted in a high frequency of Ag-specific CD8+ T-cells localized only in the liver. Importantly, i.v. administration of PLGA-OVA Nps following an i.m. vaccination with Ad5 resulted in a ten-fold increase of Ag-specific CD8+ T-cells. Ag-specific CD8+ T-cells were found to be relatively stable over time, and expressed markers of liver tissue residency and maintenance (notably, CXCR6 and CD69) [22]. In addition to PLGA-OVA Nps, i.v. viral vectors were also investigated as targeting agents. Following spz challenge with Tg *P. berghei* OVA parasites, C57BL/6 mice (a mouse strain difficult to protect by pre-erythrocytic vaccines), revealed 100% sterile protection up to two months post vaccination. Similarly, i.v. administration of either Ad5 or MVA vectors sterilely protected 80% of C57BL/6 mice two months post vaccination.

Liver stage malaria poses several challenges to vaccine development. Firstly, there is a requirement for particularly high numbers of patrolling effector CD8+ T-cells needed to recognize and kill very few infected hepatocytes in the liver, a particularly large and vascularized organ [24, 35, 36]. This requirement is due to limited Ag presentation as a result of Ag sequestration by the parasite and the establishment of an intracellular parasitophorous vacuole (PVM), in which the parasite hides and replicates [37-40]. As such the levels of Ag-specific T-cells necessary to confer protection are seldom induced and maintained by current vaccinations in the short window of sporozoite (spz) infection (approximately two days in mice, and seven days in humans) [41]. In addition, this is further complicated by the liver being an especially difficult organ in which to mount a robust immune response, due to suboptimal CD8+ T-cell priming (often by liver sinusoidal endothelial cells (LSECs)), resulting in the generation of T-cells with dysfunctional or exhausted phenotypes [42-44].

This prime and target approach circumvents some of these challenges firstly by priming CD8+ T-cells in peripheral tissue and subsequently targeting them to liver tissue with agents (Nps or viral vectors) able to successfully deliver substantial amounts of antigen. In the past, conventional viral vectors vaccine strategies aimed at inducing high levels of systemic immunity as measured through blood or splenic responses, failed to generate protective responses that were maintained in the liver over time [11]. The importance of a high frequency of hepatic Ag-specific CD8+ T-cells has been described in several works [22, 45], so far being induced only by whole parasite vaccination (such as irradiated sporozoites) [20, 46]. However, we show here that Nps and viral vectors are excellent targeting agents, and clinically tested simian adenoviruses offer a particularly translatable option for malaria. With only one viral vector requiring manufacturing and no change in immunogen for the booster dose, an i.m. followed by i.v. vaccination regimen not only significantly improves vaccine efficacy, but also greatly simplifies vaccine production.

By utilizing various viral vectors and Nps, this prime and target approach should provide a particularly flexible vaccine platform for use in multiple disease settings. Firstly, administration of viral vectors or protein loaded Nps could be used to generate localized cellular immune responses in selected tissues for example mucosal (e.g. aerosol), intradermal or intra-tumoral administration. Secondly, through viral vector engineering, different antigens can be selected and strongly expressed in a variety of different tissues, providing a potential vaccine and immunotherapy platform against diseases such as Hepatitis B and C, CMV and EBV. Although mucosal genital homing approaches has been described using non-antigen specific chemokine recruitments or UV-inactivated bacteria, prime-target immunization provides a strategy based on antigen delivery that leads to marked T-cell localization in an internal organ [47, 48]. In conclusion, a prime and target approach is able to significantly improve current antigen-based liver-stage malaria immunization strategies, and provides a new highly flexible vaccination strategy.

Example 10 Subcutaneous Administration Route for Liver Targeting

Figure 17:
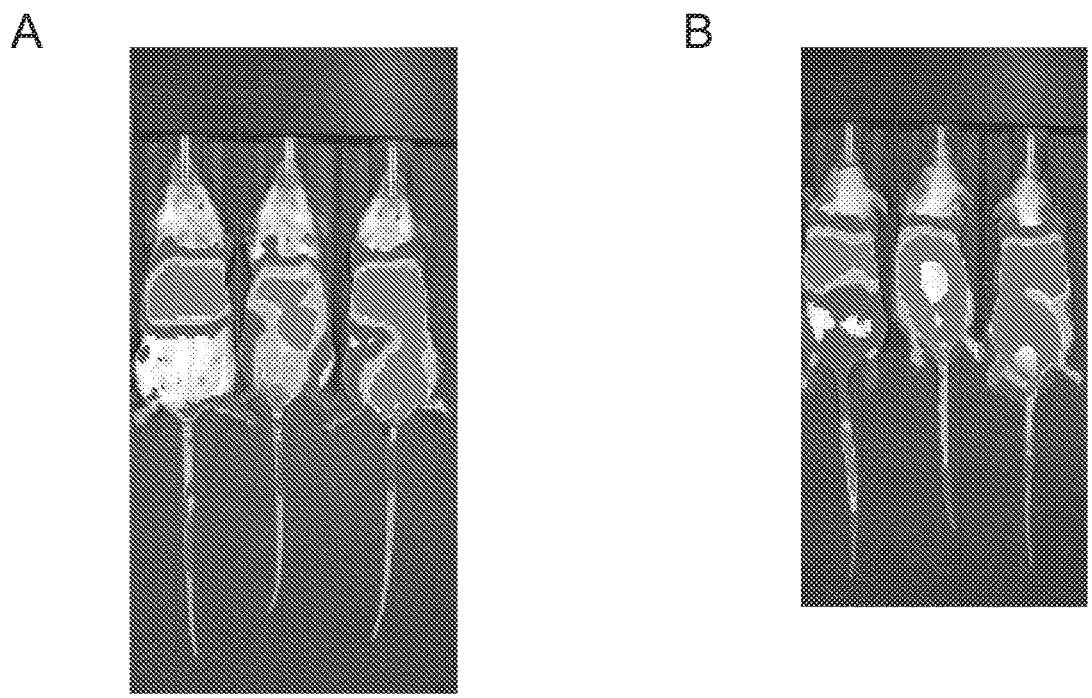
FIG. 17 shows photographs a (top), b (bottom). The mice in panels a and b had received 1: $10^8$ iu AdHu5 iv; 2: $10^9$ iu AdHu5 s.c.; 3: $5 \times 10^9$ iu AdHu5 s.c. In all panels the mice were imaged at 1 day post dosing.

To investigate whether routes other than intravenous administration could be used for the later or targeting immunisation. Mice were immunised with Ad5 expressing luciferase and the level of transgene expression in the liver was evaluated by bioluminescent imaging. As expected, (FIG. 17) at 1 day post administration intravenous administration of Ad5 showed liver targeting (FIG. 17a, 17b). Surprisingly, substantial liver targeting was observed with subcutaneous Ad5 administration, suggesting that this route could be used for the targeting immunisation in prime-target immunisation strategies.

To assess this possibility further mice were immunised with Ad5 encoding Ova with a range of routes: the C57/BL6 mouse groups studied were with an interval between doses of two weeks.

| 1) Ad im | Ad iv |
| 2) Ad im | Ad im |
| 3) Ad im | Ad sc |
| 4) Ad iv | Ad iv |
| 5) Ad sc | Ad sc |

Figure 18:
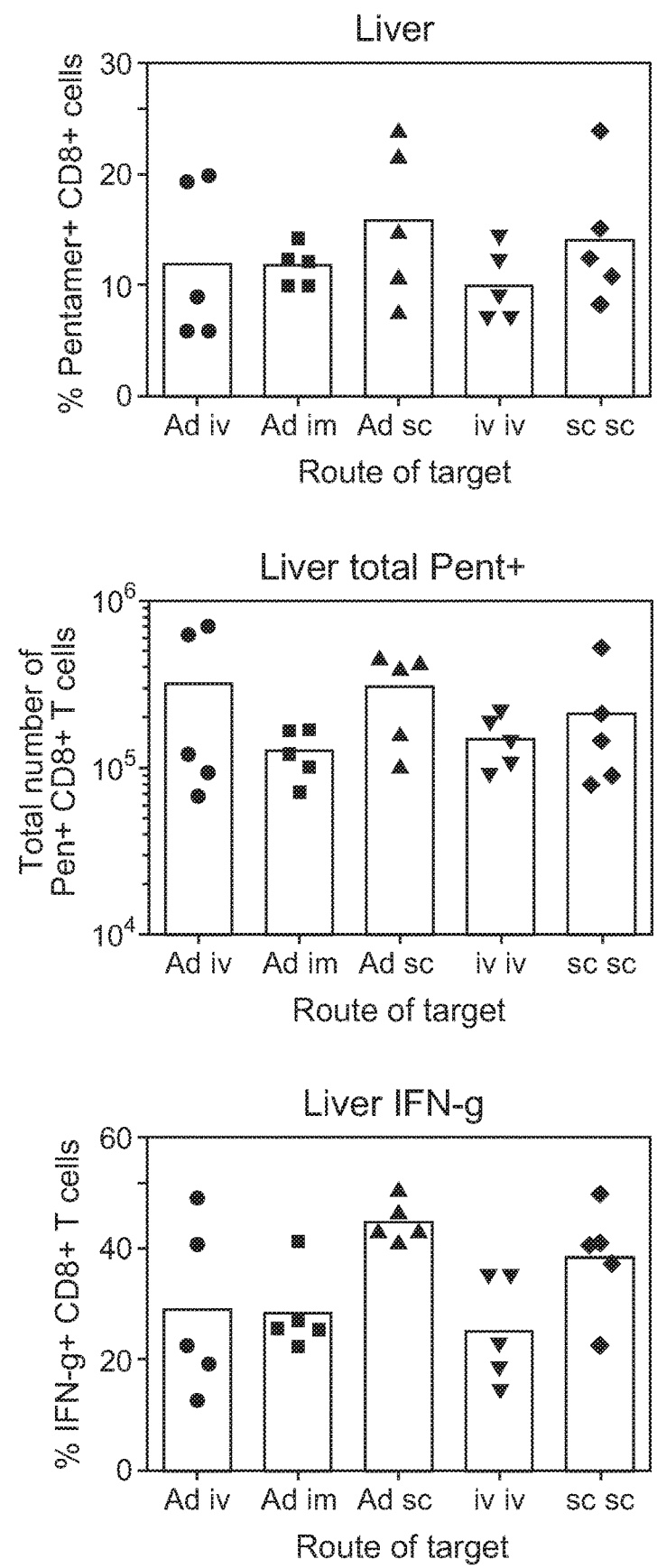
FIG. 18 shows bar charts Liver T cell responses measured after various two dose immunisation regimes, each with a 2 week interval between doses: left to right, as follows: 1) Ad im-Ad iv; 2) Ad im-Ad im; 3) Ad im-Ad sc; 4) Ad iv-Ad iv; 5) Ad sc-Ad sc. The first dose was in all groups $10^8$ iu of Ad5-Ova; the second dose in all groups was $10^9$ iu of Ad5-Ova. Flow cytometry and pentamer (Pent+) analysis of liver cells and splenocytes in C57/BL/6 mice are shown 3 weeks after the second dose.
Figure 18:
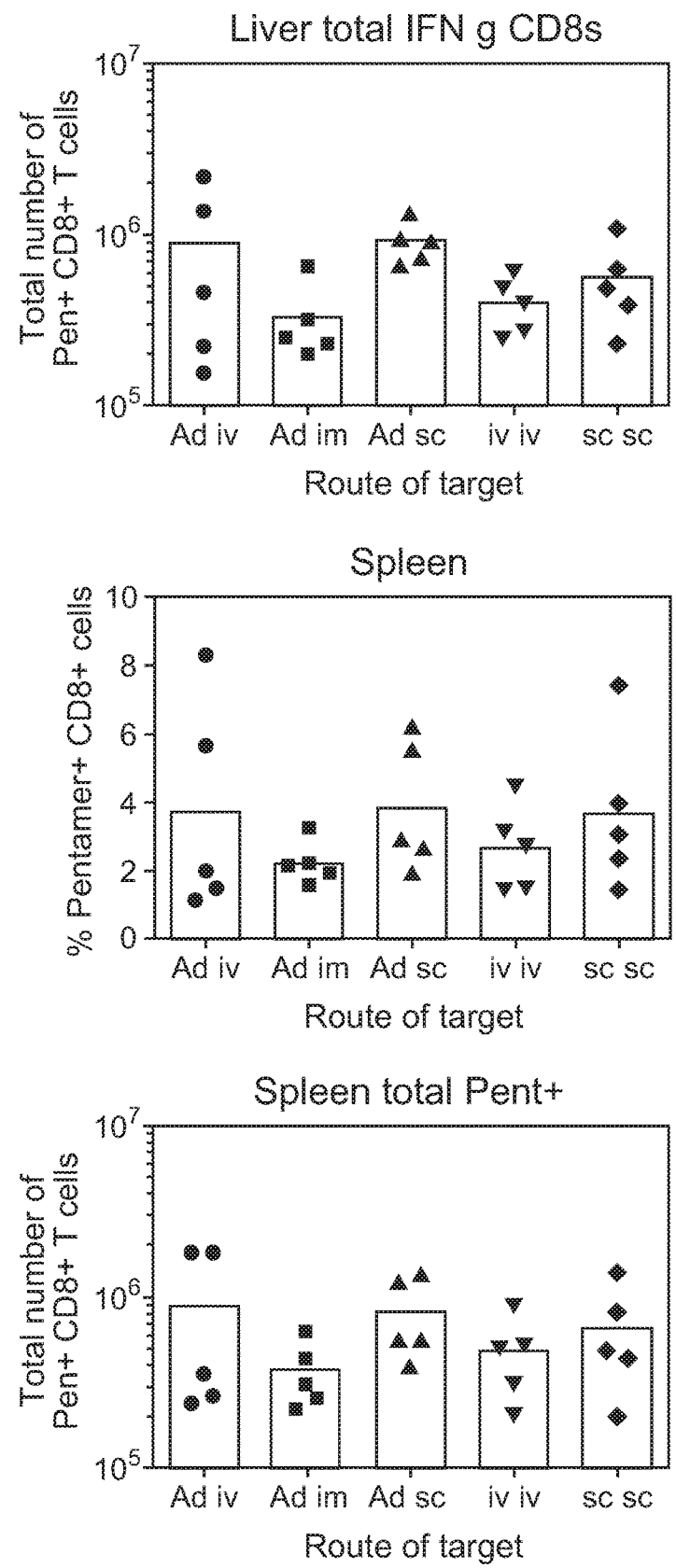

It was found (FIG. 18) that liver interferon gamma positive CD8 T cells were strikingly high in group 3) where sc administration of the Ad5 vector followed an i.m. priming dose. Indeed the response was as strong in this experiment as is group 1) which used an i.v. targeting immunisation. Hence these data strongly support the view that the targeting immunisation with an s.c. administration may be used as an alternative to the i.v. route.

Example 11: Subcutaneous as Well as Intraperitoneal Routes are Effective

We show that sub-cut is better than im. In particular we show that subcutaneous as well as intraperitoneal routes have value in terms of improved efficacy over i.m. boosting i.e. when used as the second composition (the targeting composition).

FIG. 26 indicates statistical significance between groups. This is good supporting evidence.

It will be noted that i.p. immunisation is a standard route in mice but not used generally in humans.

FIG. 26 shows targeting with Adenovirus administered sub-cutaneously or intra-peritoneally confers greater protection than intra-muscular targeting. C57BL/6 mice were primed with $10^8$ iu of Ad5-OVA and two weeks later were targeted with either $10^9$ iu of Ad5-OVA administered intravenously (black circle), intra-peritoneally (open square), sub-cutaneously (black triangle) or intra-muscularly (filled square). Three weeks after the targeting vaccination, mice were challenged with 1000 *P. berghei* OVA (hep17) sporozoites and monitored for the development of blood-stage malaria, unvaccinated mice served as infection controls (grey squares). Data was analysed with a log rank Mantel-Cox test and asterisk denote significant differences between groups after Bonferroni correction, demonstrating targeting with Ad intramuscularly achieves a small delay in development of malaria compared to control m ice. Targeting with sub-cutaneous Adenovirus significantly improves protection compared to the intra-muscular targeted group, while adenovirus administered intra-peritoneally further improves protection over the Adenovirus sub-cutaneous group.

Further Examples

With reference to example 1, this "prime-target" immunisation regime was initially demonstrated to induce 80% sterile protection with vectors encoding ovalbumin followed by challenge with transgenic *P. berghei* sporozoites expressing ovalbumin.

Then we showed that the ChAd and MVA vectored vaccines expressing the *P. falciparum* ME-TRAP insert, which have been assessed extensively clinically, also provide 100% efficacy with an intravenous boost whereas only 30% efficacy or less (depending on mouse strain) could be achieved with the booster administered by other routes.

We then extended this approach to show 100% efficacy with two other pre-erythrocytic malaria antigens against transgenic parasite challenge. Very interestingly, 100% efficacy could also be observed with an intramuscular adenovirus prime—intravenous adenovirus boost vaccine regime in mice, so that a heterologous vector (i.e. MVA) was not required.

Example 7: Sterile Protection can Also be Achieved with Other Clinically Relevant Malaria Antigens Clinically relevant liver-stage malaria antigens were then investigated. Importantly, PfLSA1 and PfTRAP were both investigated in BALB/c and CD1 mice respectively. BALB/c mice were immunized with $1\times10^8$ iu of ChAd63-PfLSA1 i.m. and two weeks later the same vector was given i.v. at a $1\times10^9$ iu dose. Ad was chosen as the targeting vaccine as it would simplify the vaccination regimen in the field if only one vector (i.e. Ad alone) and not two (Ad plus MVA) needed to be manufactured and used. Similarly, CD1 mice were immunized with the same regimen containing the antigen cassette, PfTRAP.

Figure 15:
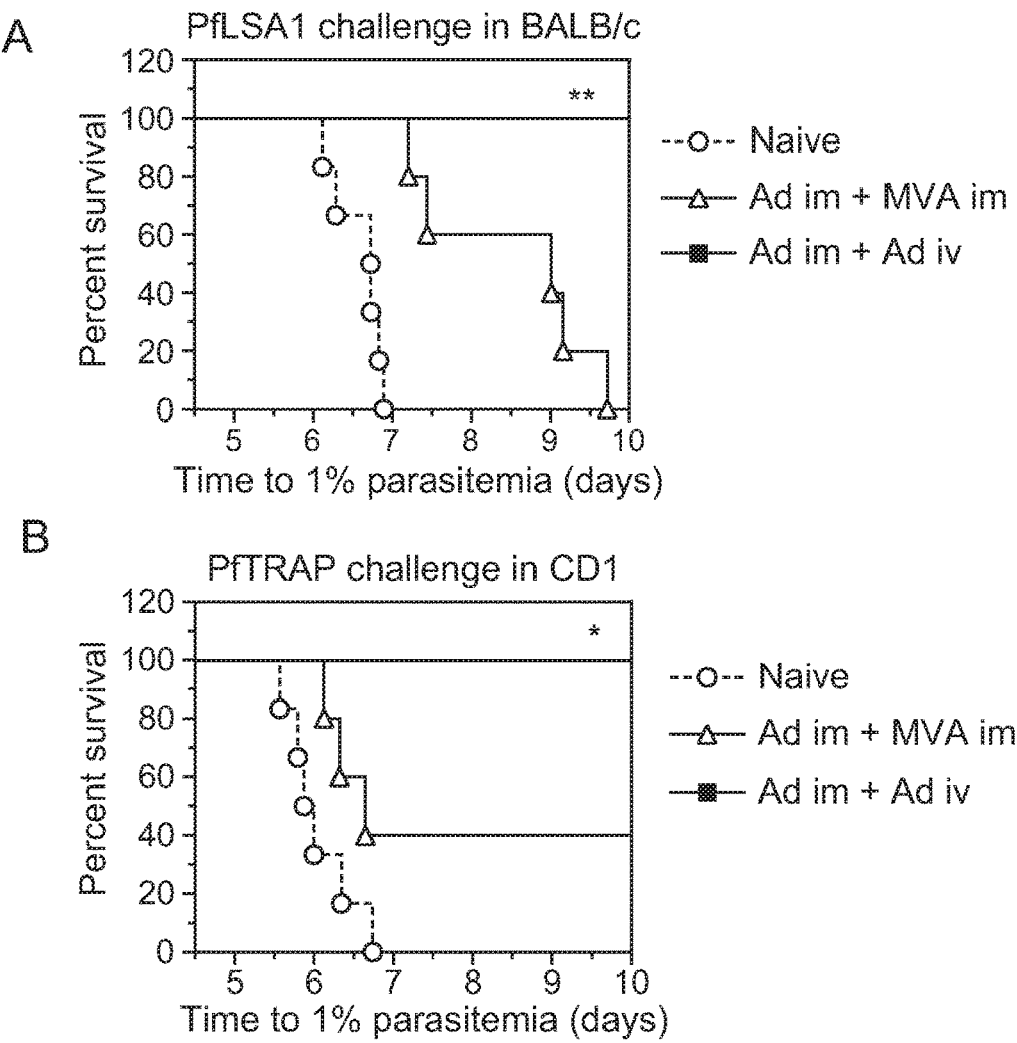
FIG. 15 shows (see examples)

As before, 100% of mice receiving a prime-target strategy were protected (FIGS. 15A and 15B). FIG. 15 shows two graphs. A classic heterologous intramuscular prime-boost strategy Ad-MVA, showed no sterile protection in PfLSA1 vaccinated mice when challenged 3 weeks post MVA boost. A significant delay to 1% parasitemia was however observed. PfTRAP vaccinated CD1 mice with heterologous prime-boost strategy showed 40% sterile protection, much less than the 100% observed with the prime-target regimen.

Together, these experiments show a substantial advance in clinically relevant malaria vaccine development, greatly improving the current prime-boost viral vector vaccine strategies.

Viral Vector Intravenous Administration can be Used as an Alternative Targeting Approach Having determined that high liver antigen delivery significantly enhances the frequency of CD8$^+$ T-cells expressing residency markers, the capacity of clinically tested adenoviral and MVA vectors as a liver antigen-delivery method was assessed. These non-replication competent viral vectors are known to stably express proteins, with each vector exhibiting a unique kinetics profile [9]. Importantly, they have shown good safety profiles in humans following both i.m. and i.v. routes of administration [29-31]. Human Ad5, Chimpanzee adenovirus (ChAd63), and MVA viral vectors containing a luciferase (Luc) cassette were administered via i.v. in mice, and bioluminescence imaging was performed over time (FIG. 5F). Quantification of region of interest (ROI) photon flux intensity, revealed that both the human and simian Ad viral vectors are highly liver tropic with strong and stable luciferase expression (FIG. 5G). MVA also displays some liver tropism with low luciferase expression very shortly after i.v. administration, while over time briefly residing in the spleen.

Figure 5:
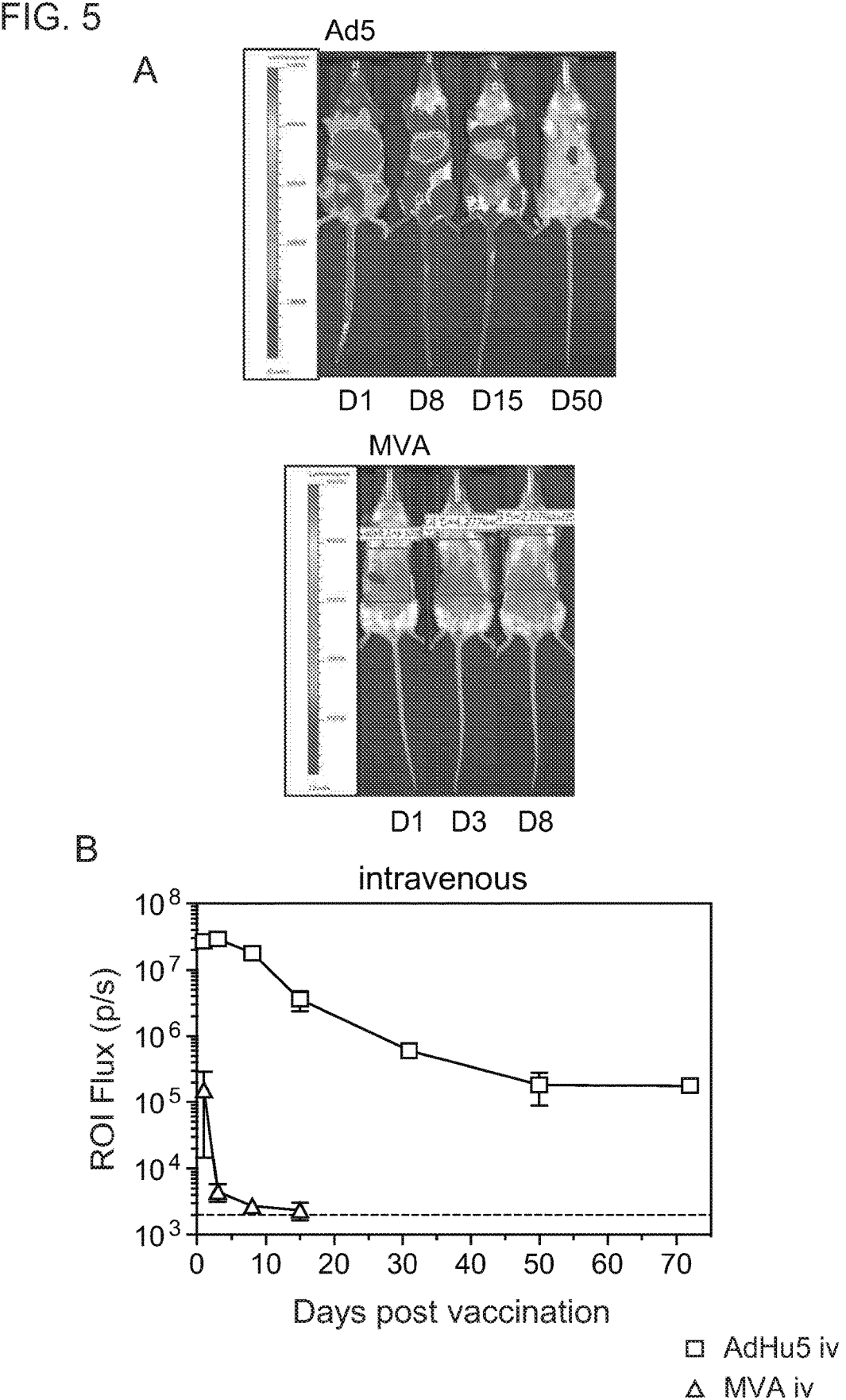
FIG. 5 shows viral vectors as targeting agents protect mice in a transgenic *P. berghei* challenge model
(A) BALB/c mice (n=5) were vaccinated i.v. with Ad5 (1×109 iu), and MVA (1×106 pfu) viral vectors expressing Firefly luciferase. Subsequently at days 1, 3, 8, 15, 30, 50 and 73 bioluminescence imaging was obtained. Overlay image indicating the location of bioluminescence signal in different groups. (B) Quantification of Region of Interest (ROI) Total flux (p/s) of different vaccination regimes over time. Dashed line shows limit of detection. Median with interquartile range shown. (C) C57BL/6 mice (n=5-6) were primed with Ad5-OVA (1×108 iu) i.m. as previously described. Two weeks later mice received either Ad5-OVA i.v. (1×109 iu; Ad), MVA-OVA i.v. (1×106 pfu; MVA), or PLGA-OVA i.v. (1×109 iu; Np iv). Three weeks later, liver and spleen tissues were harvested for cytometry analysis and total cell count of Pen+CD8+ T-cells was determined. Median values shown. Data was analyzed with a One-Way ANOVA and corrected for multiple comparisons using a Dunn's post-hoc test. p<0.05 (**). (D) C57BL/6 mice (n=6) were primed with Ad5-OVA (1×108 iu; □) i.m. as previously described. Two weeks later mice received either Ad5-OVA i.m. (1×109 iu; D), MVA-OVA i.m. (1×106 pfu; ▲), Ad5-OVA i.v. (1×109 iu;) or MVA-OVA i.v. (1×106 pfu; ▲). An unvaccinated group served as the infection control (○). Mice were challenged with 1000 transgenic *P. berghei* spz expressing OVA under the Hep17 promoter 3 weeks post vaccination. (E) Similar experimental set up including an additional group of mice which had received PLGA-OVA i.v. in place of a second dose of vector ( ). Mice were challenged 8 weeks post vaccination with parasitemia assessed using thin blood smear and time to 1% parasitemia calculated by linear regression. Survival curve analysis was performed using log rank Mantel-Cox test. p<0.001 (*); p<0.005 (). (see examples)
Figure 5:
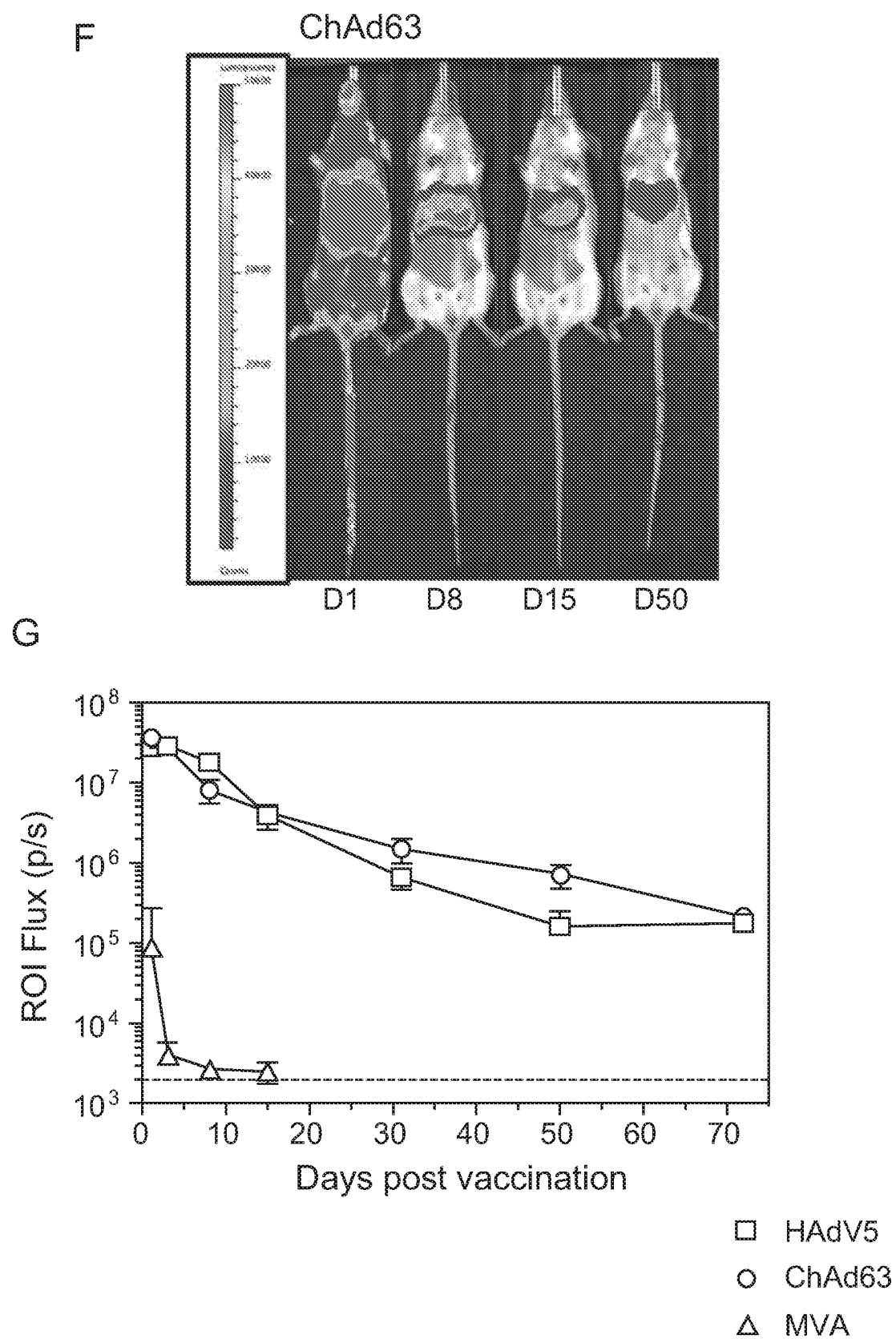

FIGS. 5 F and G show photographs and a graph: viral vectors as targeting agents protect mice in a transgenic *P. berghei* challenge model. (FIG. 5F) BALB/c mice (n=5) were vaccinated i.v. ChAd36 (1×109 iu) viral vectors expressing Firefly luciferase. Subsequently at days 1, 3, 8, 15, 30, 50 and 73 bioluminescence imaging was obtained. Overlay image indicating the location of bioluminescence signal in different groups. (FIG. 5G) Quantification of Region of Interest (ROI) Total flux (p/s) of different vaccination regimes over time. Dashed line shows limit of detection. Median with interquartile range shown.

Sterile Protection can be Achieved with the Clinically Relevant Malaria Antigens To investigate the protective ability of the prime and target strategy with clinically relevant antigens and viral vectors, mice were vaccinated with *P. falciparum* liver-stage malaria antigens expressed in Chimpanzee Adenovirus serotype 63 (ChAd63) viral vectors and challenged with wild-type (WT) *P. berghei* or transgenic (Tg) *P. berghei* expressing the relevant *P. falciparum* proteins [32, 33]. ME-TRAP contains the immunodominant H-2K$^d$ restricted *P. berghei* epitope from circumsporozoite (CS) protein, Pb9, in which protection afforded by vaccination with vectors expressing Pb9 or transfer of Pb9 specific cells is CD8$^+$ T cell number dependent [34]. Liver Stage Antigen 1 (PfLSA1), Liver-stage Associated Protein 2 (PfLSAP2), and TRAP (PfTRAP) have recently been shown to mediate protection predominantly via the induction CD8$^+$ T-cell responses [32]. Mice were immunized with ChAd63 constructs i.m. and two weeks later the same vector was i.v. administered. Three weeks after the final vaccination, mice were challenged with 1000 WT or Tg *P. berghei* spz and monitored for the development of blood-stage malaria. Consistent with previous data, vaccination with a prime and target regimen conferred 100% sterile protection against all antigens tested (FIG. 6A-D), while vaccination with the standard prime-boost strategy induced only a small delay in time to 1% parasitaemia (FIG. 6A-D). Importantly, targeting with PGLA-Pb9 or ChAd.ME-TRAP displayed equivalent levels of protection. The ability to improve upon levels of protection observed with the classical heterologous prime-boost regimen administered intramuscularly, suggests that this markedly improved vectored vaccination approach merits clinical evaluation.

Figure 6:
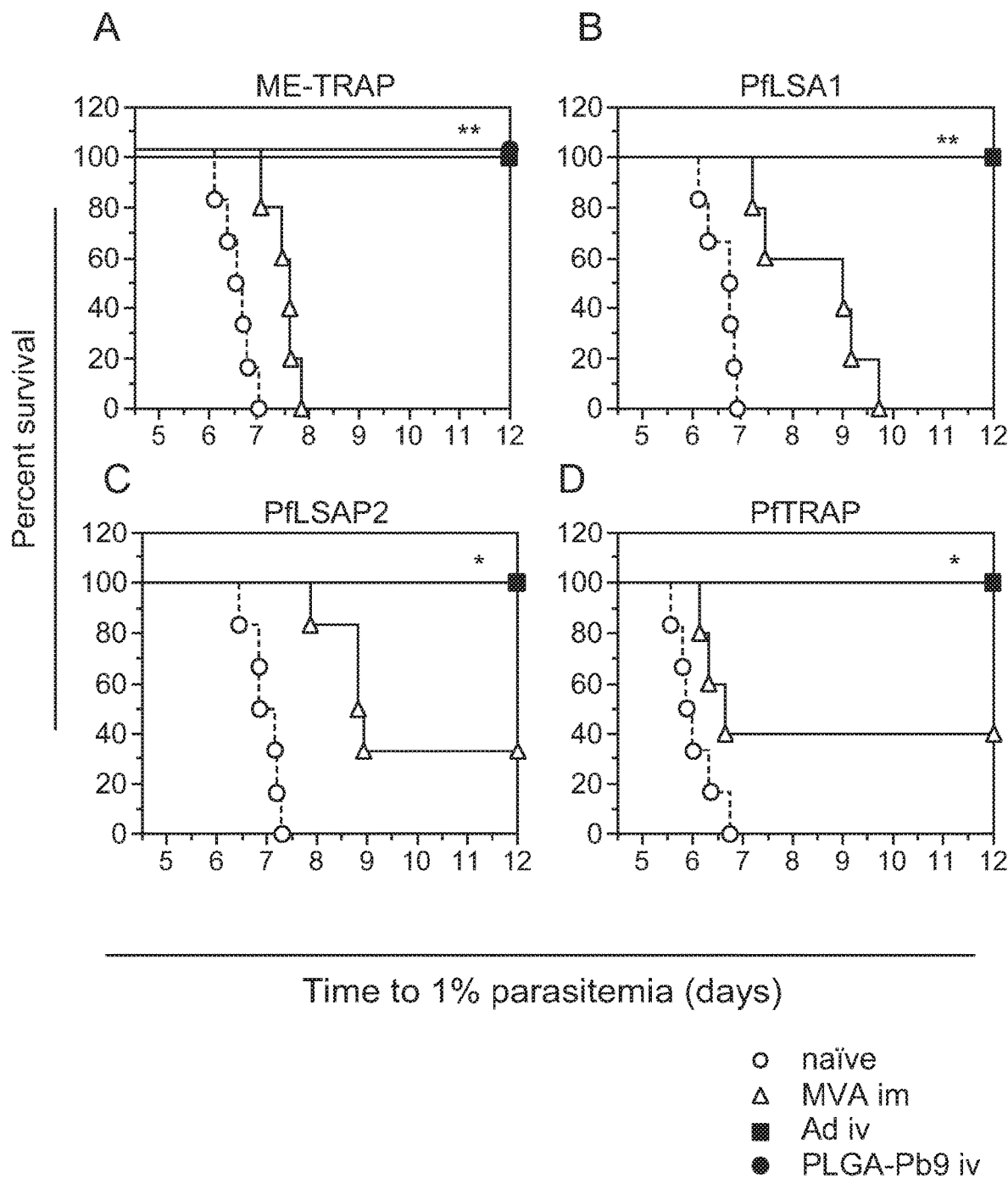
FIG. 6 shows (see examples)

FIG. 6 shows four graphs. In more detail, prime and target approach protects mice against $P.$ $berghei$ expressing clinically relevant antigens:
(A-C) Balb/c mice and (D) CD1 (n=5-6), were primed im with ChAd63 ($1\times10^8$ iu) expressing either (A) ME-TRAP, (B) PfLSA1, (C) PfLSAP2, or (D) PfTRAP. Two weeks later, MVA i.m. ($1\times10^6$ pfu) ($\Delta$), as a conventional boost, or ChAd63 iv. ($1\times10^9$ iu) expressing homologous antigen (■) were administered. In the case of ME-TRAP (A), a further group of mice received PLGA particles containing the immunodominant epitope Pb9 (●). An additional unvaccinated group served as the infection control in ah groups (○). Mice were then challenged 3 weeks later with 1000 $P.$ $berghei$ spz transgenic for the corresponding antigen. Parasitemia was assessed using thin blood smear and time to 1% parasitemia calculated by linear regression. Survival curve analysis was performed using log rank Mantel-Cox test. $p<0.05$ (*); $p<0.005$ (**)

Example 8: Protective Efficacy of ChAdOx1 LS2 and MVA LS2 Administered Intravenously See FIG. 27.
A) BALB/c mice were immunised with $10^8$ iu ChAdOx1 LS2 im followed 2 weeks later with $10^6$ pfu with MVA LS2 im and a further 2 weeks later mice received 107 pfu MVA LS2 either intravenously (iv) or intramuscularly (im). Mice were challenged with 1000 double chimeric $P.$ $berghei$ parasites expressing PfLSA1 and PfLSAP2 3 weeks after the final vaccination and monitored for blood-stage parasitaemia. Unvaccinated mice served as infection control. Graphs represent the time to 1% parasitaemia calculated by linear regression from daily parasite growth.
B) Outbred CD-1 mice were immunised with $10^8$ iu ChAdOx1 LS2 im followed 2 weeks later with $10^6$ pfu with MVA LS2 im and a further 2 weeks later mice received $10^9$ iu ChAdOx1 LS2 either intravenously (iv) or intramuscularly (im). Mice were challenged with 1000 double chimeric $P.$ $berghei$ parasites expressing PfLSA1 and PfLSAP2 3 weeks after the final vaccination and monitored for blood-stage parasitaemia. Unvaccinated mice served as infection control. Graphs represent the time to 1% parasitaemia calculated by linear regression from daily parasite growth.

These data are related to FIG. 6, where mice were challenged with $P.$ $berghei$ and clinically relevant antigens.

LS2 is our clinical construct containing 2 liver stage antigens (LSA-1 and LSAP-2), together with a molecular adjuvant, which in this example is the transmembrane domain of shark invariant chain.

The sequence for LSA-1 and LSAP2 are as in the table under the heading 'Antigens' in the description section above.

Shark invariant chain has an accession number AEX34752.1 and/or is as described in PCT/GB2014/053596 (e.g. as published as WO2015/082922).

REFERENCES

1. Murray, C. J., et al., $Global,$ $regional,$ $and$ $national$ $incidence$ $and$ $mortality$ $for$ $HIV,$ $tuberculosis,$ $and$ $malaria$ $during$ $1990$-$2013$: $a$ $systematic$ $analysis$ $for$ $the$ $Global$ $Burden$ $of$ $Disease$ $Study$ 2013. Lancet, 2014. 384(9947): p. 1005-70.
2. $Global.$ $WHO$ $declares$ $emergency$ $against$ $AIDS,$ $TB,$ $malaria.$ AIDS policy & law, 2006. 21(9): p. 5.
3. Agnandji, S. T., et al., $A$ $phase$ 3 $trial$ $of$ $RTS,S/ASO1$ $malaria$ $vaccine$ $in$ $African$ $infants.$ The New England journal of medicine, 2012. 367(24): p. 2284-95.
4. Neafsey, D. E., et al., $Genetic$ $Diversity$ $and$ $Protective$ $Efficacy$ $of$ $the$ $RTS,S/ASO1$ $Malaria$ $Vaccine.$ The New England journal of medicine, 2015.
5. Agnandji, S. T., et al., $First$ $results$ $of$ $phase$ 3 $trial$ $of$ $RTS,S/ASO1$ $malaria$ $vaccine$ $in$ $African$ $children.$ The New England journal of medicine, 2011. 365(20): p. 1863-75.
6. Schofield, L., et al., $Gamma$ $interferon,$ $CD8^+T$ $cells$ $and$ $antibodies$ $required$ $for$ $immunity$ $to$ $malaria$ $sporozoites.$ Nature, 1987. 330(6149): p. 664-6.
7. Weiss, W. R., et al., $CD8^+T$ $cells$ ($cytotoxic/suppressors$) $are$ $required$ $for$ $protection$ $in$ $mice$ $immunized$ $with$ $malaria$ $sporozoites.$ Proceedings of the National Academy of Sciences of the United States of America, 1988. 85(2): p. 573-6.
8. Hill, A. V., et al., $Prime$-$boost$ $vectored$ $malaria$ $vaccines$: $progress$ $and$ $prospects.$ Human vaccines, 2010. 6(1): p. 78-83.
9. Li, S., et al., $Priming$ $with$ $recombinant$ $influenza$ $virus$ $followed$ $by$ $administration$ $of$ $recombinant$ $vaccinia$ $virus$ $induces$ $CD8^+T$-$cell$-$mediated$ $protective$ $immunity$ $against$ $malaria.$ Proceedings of the National Academy of Sciences of the United States of America, 1993. 90(11): p. 5214-8.
10. Ewer, K. J., et al., $Protective$ $CD8^+T$-$cell$ $immunity$ $to$ $human$ $malaria$ $induced$ $by$ $chimpanzee$ $adenovirus$-$MVA$ $immunisation.$ Nature communications, 2013. 4: p. 2836.
11. Reyes-Sandoval, A., et al., $Prime$-$boost$ $immunization$ $with$ $adenoviral$ $and$ $modified$ $vaccinia$ $virus$ $Ankara$ $vectors$ $enhances$ $the$ $durability$ $and$ $polyfunctionality$ $of$ $protective$ $malaria$ $CD8^+T$-$cell$ $responses.$ Infection and immunity, 2010. 78(1): p. 145-53.
12. Capone, S., et al., $Immune$ $responses$ $against$ $a$ $liver$-$stage$ $malaria$ $antigen$ $induced$ $by$ $simian$ $adenoviral$ $vector$ $AdCh63$ $and$ $MVA$ $prime$-$boost$ $immunisation$ $in$ $non$-$human$ $primates.$ Vaccine, 2010. 29(2): p. 256-65.
13. Rampling, T., et al., $A$ $Monovalent$ $Chimpanzee$ $Adenovirus$ $Ebola$ $Vaccine$—$Preliminary$ $Report.$ N Engl J Med, 2015.
14. McShane, H., et al., $Recombinant$ $modified$ $vaccinia$ $virus$ $Ankara$ $expressing$ $antigen$ $85A$ $boosts$ $BCG$-$primed$ $and$ $naturally$ $acquired$ $antimycobacterial$ $immunity$ $in$ $humans.$ Nat Med, 2004. 10(11): p. 1240-4.
15. Seder, R. A. and A. V. Hill, $Vaccines$ $against$ $intracellular$ $infections$ $requiring$ $cellular$ $immunity.$ Nature, 2000. 406(6797): p. 793-8.
16. Ogwang, C., et al., $Prime$-$boost$ $vaccination$ $with$ $chimpanzee$ $adenovirus$ $and$ $modified$ $vaccinia$ $Ankara$ $encoding$ $TRAP$ $provides$ $partial$ $protection$ $against$ $Plasmodium$ $falciparum$ $infection$ $in$ $Kenyan$ $adults.$ Sci Transl Med, 2015. 7(286): p. 286re5.
17. Radtke, A. J., S. W. Tse, and F. Zavala, $From$ $the$ $draining$ $lymph$ $node$ $to$ $the$ $liver$: $the$ $induction$ $and$ $effector$ $mechanisms$ $of$ $malaria$-$specific$ $CD8$+ $T$ $cells.$ Semin Immunopathol, 2015. 37(3): p. 211-20.
18. Lim, K., et al., $Neutrophil$ $trails$ $guide$ $influenza$-$specific$ $CD8$(+) $T$ $cells$ $in$ $the$ $airways.$ Science, 2015. 349(6252): p. aaa4352.

19. Schenkel, J. M., et al., *T cell memory. Resident memory CD8 T cells trigger protective innate and adaptive immune responses*. Science, 2014. 346(6205): p. 98-101.
20. Epstein, J. E., et al., *Live attenuated malaria vaccine designed to protect through hepatic CD8(+) T cell immunity*. Science, 2011. 334(6055): p. 475-80.
21. Guebre-Xabier, M., R. Schwenk, and U. Krzych, *Memory phenotype CD8(+) T cells persist in livers of mice protected against malaria by immunization with attenuated Plasmodium berghei sporozoites*. Eur J Immunol, 1999. 29(12): p. 3978-86.
22. Tse, S. W., et al., *The chemokine receptor CXCR6 is required for the maintenance of liver memory CD8(+) T cells specific for infectious pathogens*. J Infect Dis, 2014. 210(9): p. 1508-16.
23. Mohammad, A. K. and J. J. Reineke, *Quantitative detection of PLGA nanoparticle degradation in tissues following intravenous administration*. Molecular pharmaceutics, 2013. 10(6): p. 2183-9.
24. Reyes-Sandoval, A., et al., *CD8$^+$T effector memory cells protect against liver-stage malaria*. Journal of immunology, 2011. 187(3): p. 1347-57.
25. Kasturi, S. P., et al., *Programming the magnitude and persistence of antibody responses with innate immunity*. Nature, 2011. 470(7335): p. 543-7.
26. Clarke, S. R., et al., *Characterization of the ovalbumin-specific TCR transgenic line OT-I: MHC elements for positive and negative selection*. Immunol Cell Biol, 2000. 78(2): p. 110-7.
27. Reyes-Sandoval, A., et al., *Single-dose immunogenicity and protective efficacy of simian adenoviral vectors against Plasmodium berghei*. Eur J Immunol, 2008. 38(3): p. 732-41.
28. Mueller, S. N., et al., *Memory T cell subsets, migration patterns, and tissue residence*. Annu Rev Immunol, 2013. 31: p. 137-61.
29. Rollier, C. S., et al., *Viral vectors as vaccine platforms: deployment in sight*. Curr Opin Immunol, 2011. 23(3): p. 377-82.
30. Small, E. J., et al., *A phase I trial of intravenous CG7870, a replication-selective, prostate-specific antigen-targeted oncolytic adenovirus, for the treatment of hormone-refractory, metastatic prostate cancer*. Mol Ther, 2006. 14(1): p. 107-17.
31. Park, S. H., et al., *Phase 1b Trial of Biweekly Intravenous Pexa-Vec (JX-594), an Oncolytic and Immunotherapeutic Vaccinia Virus in Colorectal Cancer*. Mol Ther, 2015. 23(9): p. 1532-40.
32. Longley, R. J., et al., *Comparative assessment of vaccine vectors encoding ten malaria antigens identifies two protective liver-stage candidates*. Sci Rep, 2015. 5: p. 11820.
33. Longley, R. J., et al., *Identification of Immunodominant Responses to the Plasmodium falciparum: Antigens PfUIS3, PfLSA1 and PfLSAP2 in Multiple Strains of Mice*. PLoS One, 2015. 10(12): p. e0144515.
34. Romero, P., et al., *Cloned cytotoxic T cells recognize an epitope in the circumsporozoite protein and protect against malaria*. Nature, 1989. 341(6240): p. 323-6.
35. Schmidt, N. W., et al., *Memory CD8 T cell responses exceeding a large but definable threshold provide long-term immunity to malaria*. Proceedings of the National Academy of Sciences of the United States of America, 2008. 105(37): p. 14017-22.
36. Schmidt, N. W., et al., *Extreme CD8 T cell requirements for anti-malarial liver-stage immunity following immunization with radiation attenuated sporozoites*. PLoS pathogens, 2010. 6(7): p. e1000998.
37. Cockburn, I. A., et al., *Dendritic cells and hepatocytes use distinct pathways to process protective antigen from plasmodium in vivo*. PLoS pathogens, 2011. 7(3): p. e1001318.
38. Crompton, P. D., et al., *Malaria immunity in man and mosquito: insights into unsolved mysteries of a deadly infectious disease*. Annual review of immunology, 2014. 32: p. 157-87.
39. Jung, S., et al., *In vivo depletion of CD11c+ dendritic cells abrogates priming of CD8+ T cells by exogenous cell-associated antigens*. Immunity, 2002. 17(2): p. 211-20.
40. Marsh, K. and S. Kinyanjui, *Immune effector mechanisms in malaria*. Parasite immunology, 2006. 28(1-2): p. 51-60.
41. Murphy, S. C., et al., *A T-cell response to a liver-stage Plasmodium antigen is not boosted by repeated sporozoite immunizations*. Proceedings of the National Academy of Sciences of the United States of America, 2013. 110(15): p. 6055-60.
42. Cockburn, I. A., et al., *Prolonged antigen presentation is required for optimal CD8+ T cell responses against malaria liver stage parasites*. PLoS pathogens, 2010. 6(5): p. e1000877.
43. Crispe, I. N., et al., *Cellular and molecular mechanisms of liver tolerance*. Immunological reviews, 2006. 213: p. 101-18.
44. Protzer, U., M. K. Maini, and P. A. Knolle, *Living in the liver: hepatic infections*. Nat Rev Immunol, 2012. 12(3): p. 201-13.
45. Schmidt, N. W., et al., *Memory CD8 T cell responses exceeding a large but definable threshold provide long-term immunity to malaria*. Proc Natl Acad Sci US A, 2008. 105(37): p. 14017-22.
46. Clyde, D. F., et al., *Immunization of man against sporozite-induced falciparum malaria*. Am J Med Sci, 1973. 266(3): p. 169-77.
47. Stary, G., et al., *A mucosal vaccine against Chlamydia trachomatis generates two waves of protective memory T cells*. Science, 2015. 348(6241): p. aaa8205.
48. Shin, H. and A. Iwasaki, *A vaccine strategy that protects against genital herpes by establishing local memory T cells*. Nature, 2012. 491(7424): p. 463-7.
49. Schenkel, J. M. and D. Masopust, *Tissue-resident memory T cells*. Immunity, 2014. 41(6): p. 886-97.
50. Cauley, L. S. and L. Lefrancois, *Guarding the perimeter: protection of the mucosa by tissue-resident memory T cells*. Mucosal Immunol, 2013. 6(1): p. 14-23.

All publications mentioned in the above specification are herein incorporated by reference.

The invention claimed is:

1. A kit comprising (a) a first composition comprising a viral vector encoding an epitope of a first liver disease antigen, wherein the epitope is a CD8+ T cell epitope, said viral vector being selected from the group consisting of: adenoviral vector, adeno-associated viral vector and poxviral vector; and (b) a second composition comprising a viral vector encoding an epitope of a second liver disease antigen, wherein the epitope is a CD8+T cell epitope, the viral vector being selected from the group consisting of: adenoviral vector, adeno-associated viral vector and poxviral vector; wherein (i) the second composition is formulated for i.v. or i.p. administration, and (ii) the kit comprises a device for i.v. or i.p. administration;
   wherein the epitope of a first liver disease antigen and the epitope of a second liver disease antigen may be the same or different epitope or antigen; and wherein said first and second compositions are formulated differently for administration by different routes and the kit comprises devices for administration of said first and said second compositions by different routes.

2. The kit of claim 1, wherein the second composition is formulated for i.v. administration.

3. The kit of claim 2, wherein the viral vector in the first composition and the viral vector in the second composition are non-replication competent.

4. The kit of claim 2, wherein the viral vector in the first composition is selected from the group consisting of: ChAd3, ChAd5, ChAd63, and ChAdOx1, and the viral vector in the second composition is MVA.

5. The kit of claim 4, wherein the first liver disease antigen and the second liver disease antigen are each selected from the group consisting of: a P. falciparum TRAP antigen, a P. falciparum LSA1 antigen, a P. falciparum LSAP2 antigen, Pb9, OVA, LS2, and a-fetoprotein.

6. The kit of claim 1, wherein the first composition comprises ChAd ME-TRAP or Ad-OVA and is formulated for i.m. or s.c. administration, and the second composition comprises MVA ME-TRAP or MVA-OVA and is formulated for i.v. administration.

7. The kit of claim 6, wherein the first composition comprises about $5 \times 10^8$ vp to about $5 \times 10^{10}$ vp ChAd ME-TRAP or Ad-OVA, and the second composition comprises about $2 \times 10^6$ pfu to about $2 \times 10^8$ pfu MVA ME-TRAP or MVA-OVA.

8. The kit of claim 2, wherein the first composition is formulated for s.c. administration.

9. A method of inducing an immune response in the liver of a mammalian subject, said method comprising (a) administering to the subject a first composition comprising a viral vector encoding an epitope of a first liver disease antigen, wherein the epitope is a CD8+ T cell epitope, the viral vector being selected from the group consisting of: adenoviral vector, adeno-associated viral vector and poxviral vector; and (b) about 2 days to about 12 weeks after administration of the first composition administering to the subject by i.v. or i.p. route a second composition comprising a viral vector encoding an epitope of a second liver disease antigen, wherein the epitope is a CD8+T cell epitope, the viral vector being selected from the group consisting of: adenoviral vector, adeno-associated viral vector and poxviral vector; wherein the epitope of a first liver disease antigen and the epitope of a second liver disease antigen may be the same or different epitope or antigen; and wherein said first and second compositions are administered by different routes.

10. The method of claim 9, wherein said second composition is administered about 2 weeks after administration of said first composition.

11. The method of claim 9, wherein said epitope of a first liver disease antigen and said epitope of a second liver disease antigen is a CD8+ T cell epitope restricted by a human HLA class I molecule from a liver tumour antigen of humans or a liver cancer neoantigen epitope.

12. The method of claim 9, wherein each said epitope is flanked on each side by nucleic acids encoding at least seven amino acids of the epitope's native flanking sequence.

13. The method of claim 9, wherein said method results in a CD8+ cytotoxic T cell (CTL) immune response.

14. The method of claim 9, wherein the second composition is administered i.v.

15. The method of claim 14, wherein the viral vector in the first composition and the viral vector in the second composition are non-replication competent.

16. The method of claim 14, wherein the viral vector in the first composition is selected from the group consisting of: ChAd3, ChAd5, ChAd63, and ChAdOx1, and the viral vector in the second composition is MVA.

17. The method of claim 9, wherein the first liver disease antigen and the second liver disease antigen are each selected from the group consisting of: a P. falciparum TRAP antigen, a P. falciparum LSA1 antigen, a P. falciparum LSAP2 antigen, Pb9, OVA, LS2, and a-fetoprotein.

18. The method of claim 9, wherein the first composition comprises ChAd ME-TRAP or Ad-OVA and is administered i.m. or s.c., and the second composition comprises MVA ME-TRAP or MVA-OVA and is administered i.v.

19. The method of claim 18, wherein the first composition comprises about $5 \times 10^8$ vp to about $5 \times 10^{10}$ vp ChAd ME-TRAP or Ad-OVA, and the second composition comprises about $2 \times 10^6$ pfu to about $2 \times 10^8$ pfu MVA ME-TRAP or MVA-OVA.

20. The method of claim 14, wherein the first composition is administered s.c.

21. A method of inducing an immune response in the liver of a mammalian subject, the method comprising administering to the subject (a) a first composition comprising (i) a viral vector encoding an epitope of a first liver disease antigen, wherein the epitope is a CD8+ T cell epitope, the viral vector being selected from the group consisting of: adenoviral vector, adeno-associated viral vector and poxviral vector, or (ii) protein loaded polymer nanoparticles, wherein the protein comprises an epitope of a first liver disease antigen and the epitope is a CD8+ T cell epitope; and administering to the subject about 2 days to about 12 weeks later (b) a second composition comprising protein loaded polymer nanoparticles, wherein the protein comprises an epitope of a second liver disease antigen and the epitope is a CD8+ T cell epitope; and wherein the epitope of a first liver disease antigen and the epitope of a second liver disease antigen may be the same or different epitope or antigen.

22. The method of claim 21, wherein the second composition is administered by i.v., i.p., or s.c. route.

23. The method of claim 21, wherein the viral vector in the first composition is non-replication competent.

24. The method of claim 21, wherein the second composition is administered about 2 weeks after administration of the first composition.

25. The method of claim 21, wherein the second composition comprises protein loaded poly(lactic-co-glycolic acid) nanoparticles.

26. The method of claim 21, wherein the first composition comprises a viral vector encoding the epitope of a first liver disease antigen, wherein the viral vector is selected from the group consisting of a simian adenoviral vector, a human adenoviral vector, and MVA.

27. The method of claim 21, wherein the first composition comprises a viral vector encoding the epitope of a first liver disease antigen, the viral vector selected from the group consisting of: ChAd3, ChAd5, ChAd63, ChAdOx1, and MVA.

28. The method of claim 21, wherein the first liver disease antigen and the second liver disease antigen are each selected from the group consisting of: a P. falciparum TRAP antigen, a P. falciparum LSA1 antigen, a P. falciparum LSAP2 antigen, Pb9, OVA, LS2, and a-fetoprotein.

29. The method of claim 21, wherein the epitope of a first liver disease antigen and the epitope of a second liver disease antigen is a CD8+ T cell epitope restricted by a human HLA class I molecule from a liver tumour antigen of humans or a liver cancer neoantigen epitope.

30. The method of claim 21, wherein the nanoparticles in the second composition are selected from the group consisting of: PLGA-ME-TRAP Np, PLGA-Pb9 Np, PLGA-OVA Np, and PLGA-APC-OVA Np.

31. The method of claim 21, wherein the first composition comprises Ad-OVA, and the second composition comprises PLGA-OVA Np.

32. The method of claim 21, wherein said method results in a CD8+ cytotoxic T cell (CTL) immune response.

* * * * *

UNITED STATES PATENT AND TRADEMARK OFFICE
CERTIFICATE OF CORRECTION

PATENT NO. : 11,065,320 B2
APPLICATION NO. : 16/093095
DATED : July 20, 2021
INVENTOR(S) : Adrian V. S. Hill et al.

Page 1 of 1

It is certified that error appears in the above-identified patent and that said Letters Patent is hereby corrected as shown below:

In the Claims

Column 51, Line 14 (Claim 5): the phrase "claim 4" should read --claim 1--.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*